(12) United States Patent
Kim et al.

(10) Patent No.: US 12,109,242 B2
(45) Date of Patent: Oct. 8, 2024

(54) USE OF ALVEOLAR OR AIRWAY ORGANOIDS FOR THE TREATMENT OF LUNG DISEASES AND DISORDERS

(71) Applicant: THE CHILDREN'S MEDICAL CENTER CORPORATION, Boston, MA (US)

(72) Inventors: Carla F. Kim, Boston Charlestown, MA (US); Sharon M. Louie, Boston, MA (US); Erhan Ararat, Boston, MA (US); David Raiser, Boston, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 1025 days.

(21) Appl. No.: 17/074,118

(22) Filed: Oct. 19, 2020

(65) Prior Publication Data
US 2021/0030811 A1 Feb. 4, 2021

Related U.S. Application Data

(63) Continuation-in-part of application No. PCT/US2020/042961, filed on Jul. 22, 2020.
(Continued)

(51) Int. Cl.
| | |
|---|---|
| C12N 5/071 | (2010.01) |
| A01K 67/0271 | (2024.01) |
| A61K 9/00 | (2006.01) |
| A61K 35/42 | (2015.01) |
| A61K 45/06 | (2006.01) |

(Continued)

(52) U.S. Cl.
CPC .......... A61K 35/42 (2013.01); A01K 67/0271 (2013.01); A61K 9/007 (2013.01); A61K 9/0073 (2013.01); A61K 45/06 (2013.01); A61K 49/0008 (2013.01); C12N 5/0062 (2013.01); C12N 5/0688 (2013.01); C12N 5/0697 (2013.01); A01K 2207/12 (2013.01); A01K 2227/105 (2013.01); A01K 2267/0337 (2013.01); C12N 2506/02 (2013.01);
(Continued)

(58) Field of Classification Search
CPC ..................................................... C12N 5/0688
See application file for complete search history.

(56) References Cited

U.S. PATENT DOCUMENTS

| | | |
|---|---|---|
| 2013/0274215 A1 | 10/2013 | Thies et al. |
| 2016/0312190 A1 | 10/2016 | Ghaedi et al. |
| 2019/0091266 A1 | 3/2019 | Reisner et al. |

FOREIGN PATENT DOCUMENTS

WO     2018213421 A1     11/2018

OTHER PUBLICATIONS

Korogi et al., "In vitro disease modeling of Hermansky-Pudlak Sydrome Type 2 using human induced pluripotent stem cell-derived alveolar organoids," Stem Cell Reports 12:431-440, Mar. 2019.*
(Continued)

*Primary Examiner* — Rosanne Kosson
(74) *Attorney, Agent, or Firm* — NIXON PEABODY LLP; David S. Resnick; Jeanne N. Jodoin

(57) ABSTRACT

Various aspects described herein provide methods of generating alveolar or alveolar/airway organoids from a population of lung cells to differentiate into alveolar or alveolar/airway organoids. Also provided herein are methods and compositions for treating lung disease comprising transplantation of the alveolar or alveolar/airway organoids, or a cell isolated therefrom to a subject.

17 Claims, 56 Drawing Sheets

Related U.S. Application Data

(60) Provisional application No. 62/878,999, filed on Jul. 26, 2019.

(51) Int. Cl.
    *A61K 49/00* (2006.01)
    *C12N 5/00* (2006.01)

(52) U.S. Cl.
    CPC ...... *C12N 2506/27* (2013.01); *C12N 2506/45* (2013.01); *C12N 2513/00* (2013.01)

(56) References Cited

OTHER PUBLICATIONS

Yamamoto et al., "Long-term expansion of alveolar stem cells derived from human iPS cells in organoids," Nature Methods 14(11):1097-1115, 2017.*

Chen et al., "Long-term engraftment promotes differentiation of alveolar epithelial cells from human embryonic stem cell derived lung organoids," Stem Cells and Development 27(19):1339-1349, 2018.*

\* cited by examiner

Types of Cells and Mouse Strains

1. C57BL/6 Mice: derived from a mixture of alveolar, bronchiolar, and bronchioalveolar type organoids
   i. Sca1+ organoid cells: from a mixture of alveolar, bronchiolar, and bronchioalveolar type organoids
   ii. Sca1- organoid cells: from alveolar organoids
   iii. 3D Basal cells: from tracheospheres
2. Nude (Envigo 6905F): derived from alveolar organoids
   i. Sca1+ organoid cells: from a mixture of alveolar, bronchiolar, and bronchioalveolar type organoids
   ii. Sca1- organoid cells: from alveolar organoids
   iii. 3D Basal cells: from tracheospheres
3. Rag1 knockout (Jax 002216): freshly sorted Sca1- cells (alveolar type 2 cells)
   i. Sca1+ organoid cells: from a mixture of alveolar, bronchiolar, and bronchioalveolar type organoids
   ii. Sca1- organoid cells: from alveolar organoids
4. Nod-*scid*-gamma (Jax 005557): derived from mouse tracheospheres
   i. Sca1+ organoid cells: from a mixture of alveolar, bronchiolar, and bronchioalveolar type organoids
   ii. Sca1- organoid cells: from alveolar organoids
   iii. 3D Basal cells: from tracheospheres

*FIG. 2*

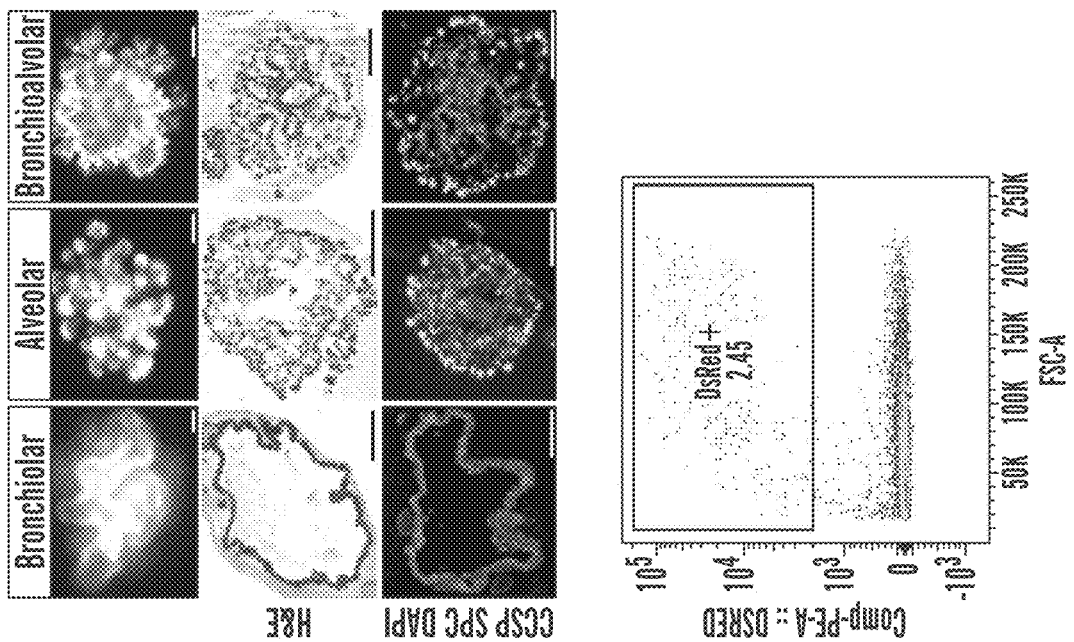
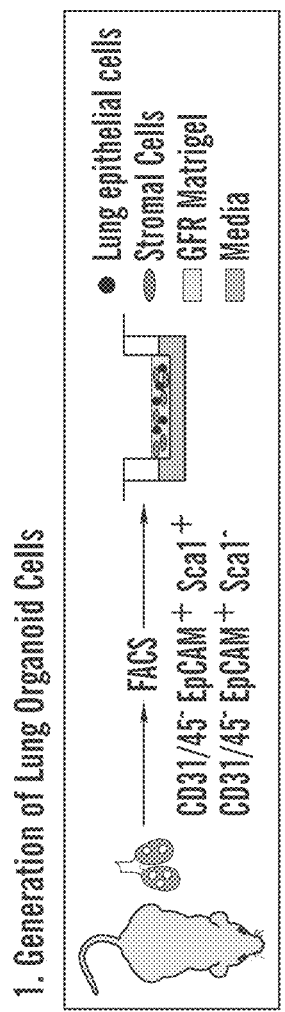
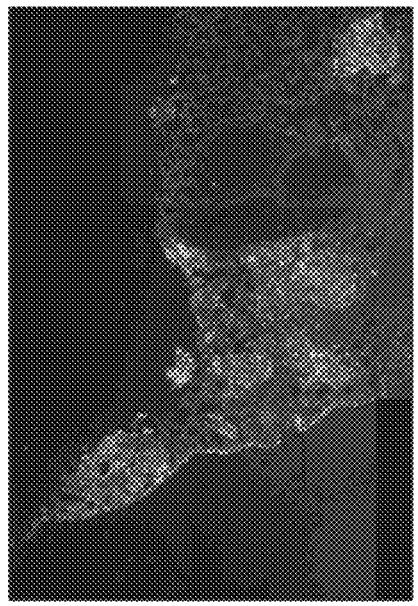
FIG. 3

|  | Nude | B6.Rag1 KO | NSG |
|---|---|---|---|
| Mature B Cells | Present | Absent | Absent |
| Mature T Cells | Absent | Absent | Absent |
| Dendritic Cells | Present | Present | Defective |
| Macrophages | Present | Present | Defective |
| NK Cells | Present | Present | Absent |
| Complement | Present | Present | Absent |
| Leakiness | Present | Absent | Very Low |

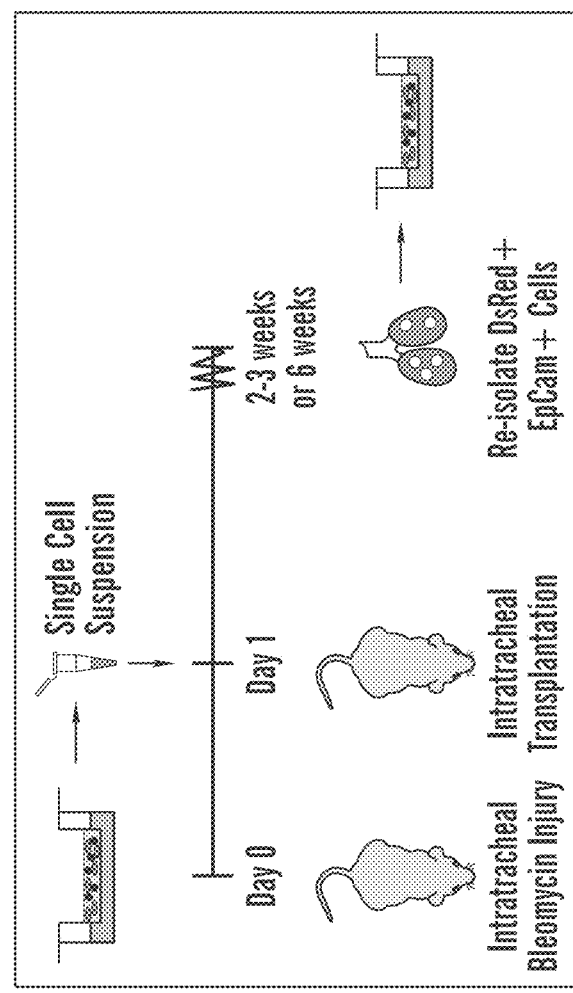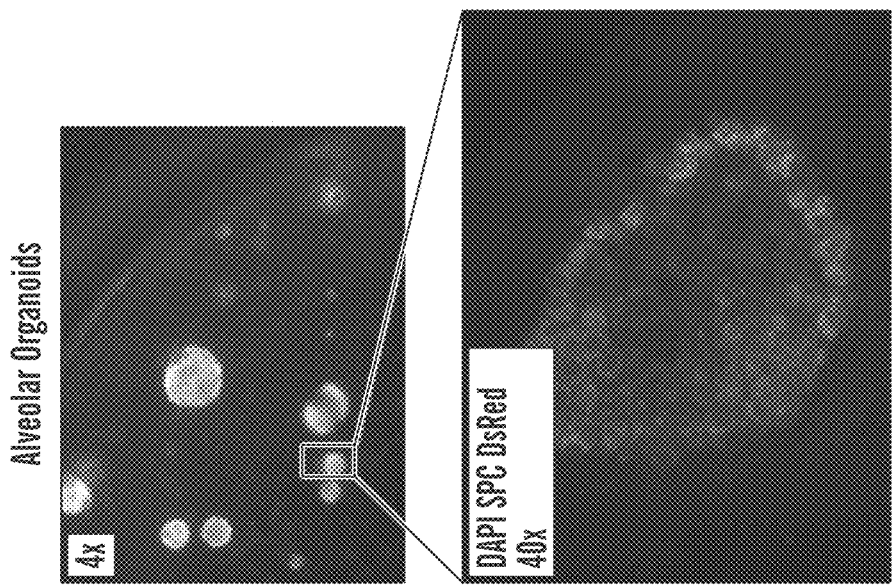
FIG. 13

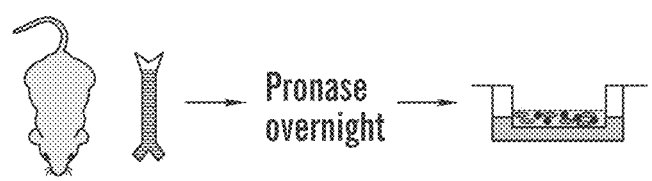
Seed in 1:1 MTEC+ media and Matrigel
No supporting cells
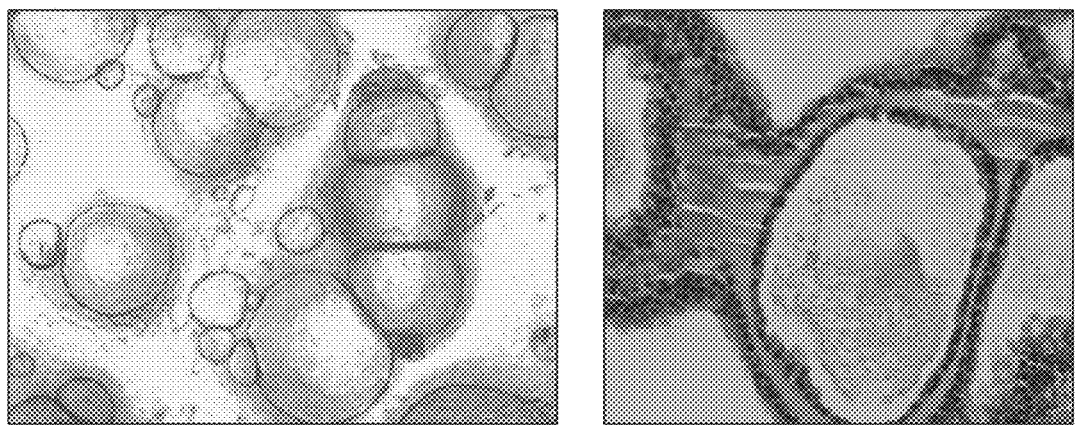
FIG. 15

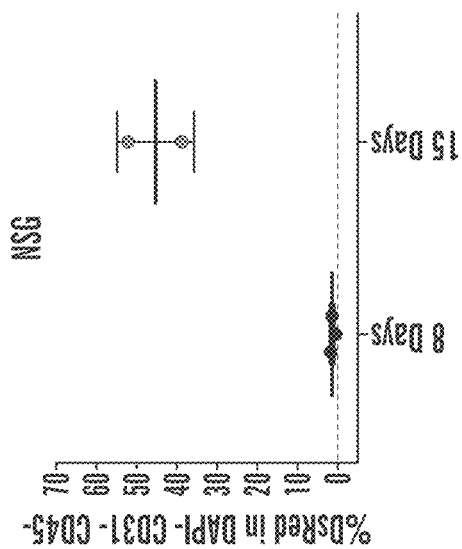
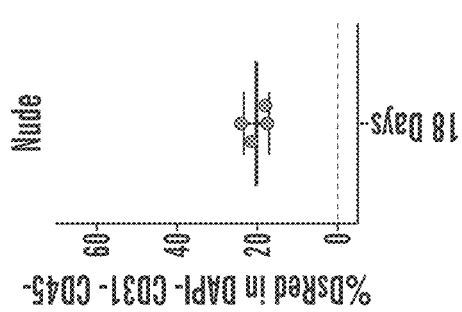
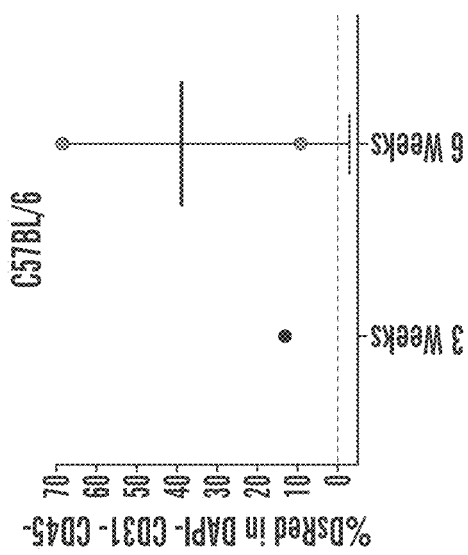
FIG. 16
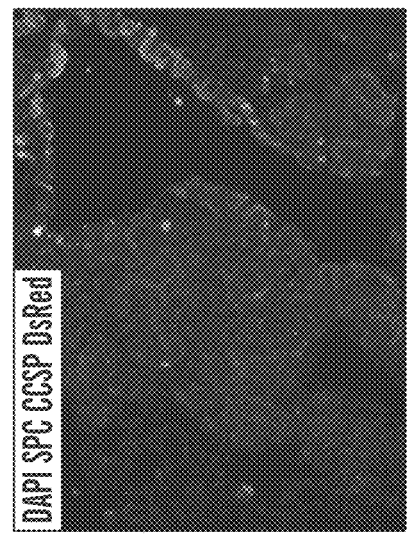
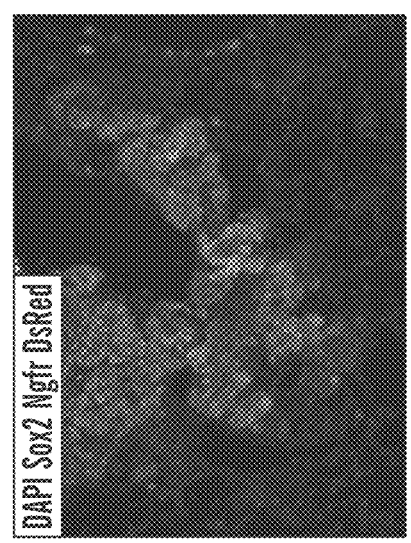
FIG. 17

2. KP Organoid Cell Orthotopic Transplantation

Both KP Sca1+ and Sca1- sorted cells can form tumor organoids.
The serial transplantation assay is the "gold standard" for studying tumor-propagating cells.
Tumor organoids are dissociated into single cell suspensions and cells are delivered orthotopically to recipient nude mice intracheally.

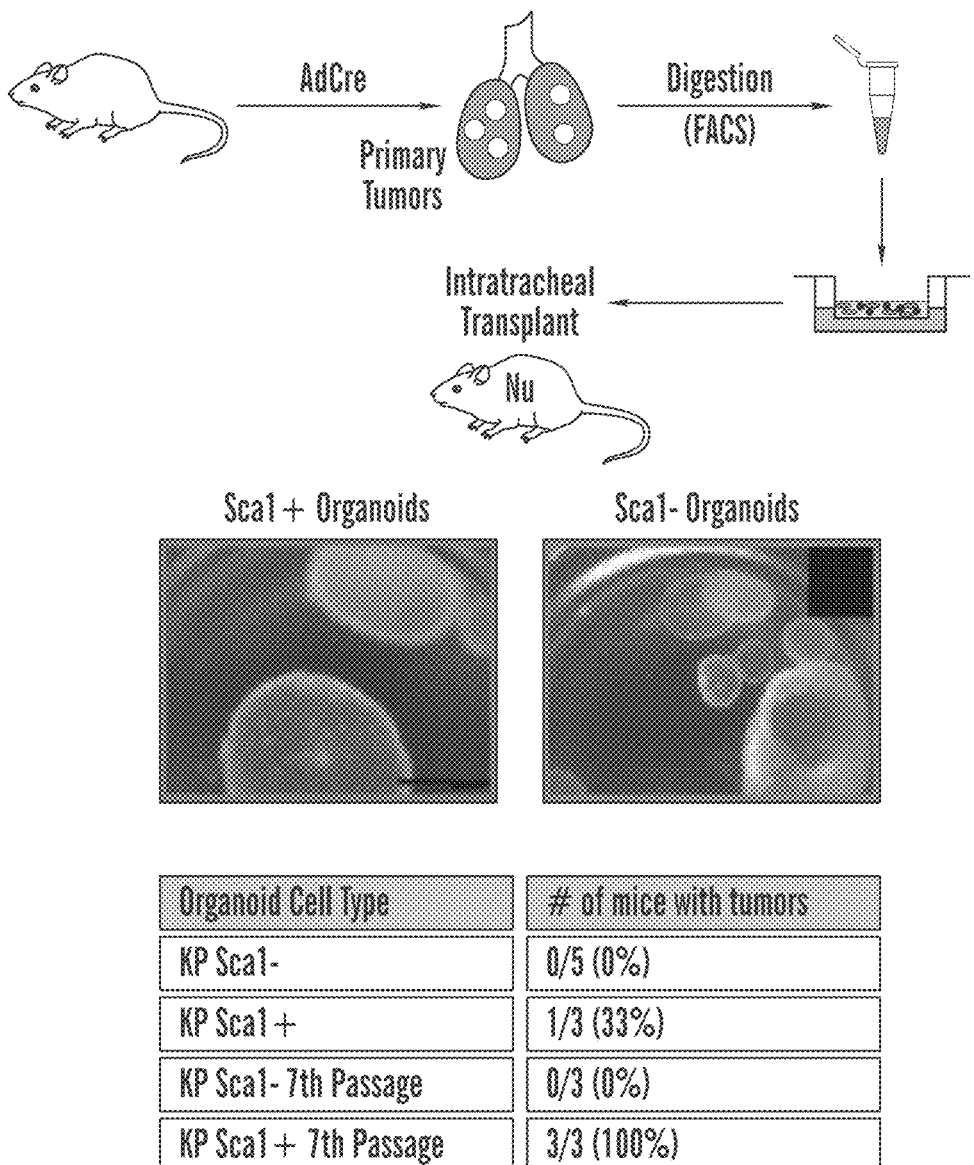

| Organoid Cell Type | # of mice with tumors |
|---|---|
| KP Sca1- | 0/5 (0%) |
| KP Sca1+ | 1/3 (33%) |
| KP Sca1- 7th Passage | 0/3 (0%) |
| KP Sca1+ 7th Passage | 3/3 (100%) |

KP Sca1+ organoid cells are more likely to initiate lung tumors in nude mice compared to Sca1- organoid cells. Upon passaging the organoids seven times, Sca1+ organoid cells were even more likely to initiate tumors in nude mice. Sca1+ organoid cells are likely enriched for TPCs compared to Sca1- organoid cells in KP mice.

*FIG. 18 (cont.)*

2. Types of Organoids
Sca-1- cell co-cultures yield alveolar-type organoids
Sca-1+ cell co-cultures yield bronchiolar, bronchioalveolar, and alveolar-type organoids

3. Lung Injury

Prior to transplanting organoid cells, 8-12 weeks old recipient mice received a single dose of Bleomycin (1.5U/Kg in PBS) intratracheally.

4. Organoid Cell Orthotopic Transplantation

One day after bleomycin-induced injury, lung organoid cells were delivered to recipient mice intratracheally. Endpoint analysis was performed 2-3 weeks or 6 weeks post-cell transplantation.

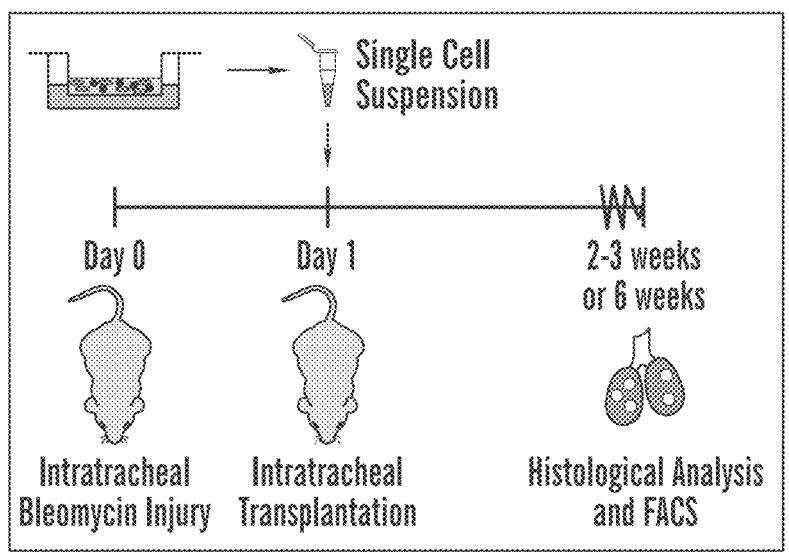

Donor cells can be detected by histological analysis and flow cytometry.

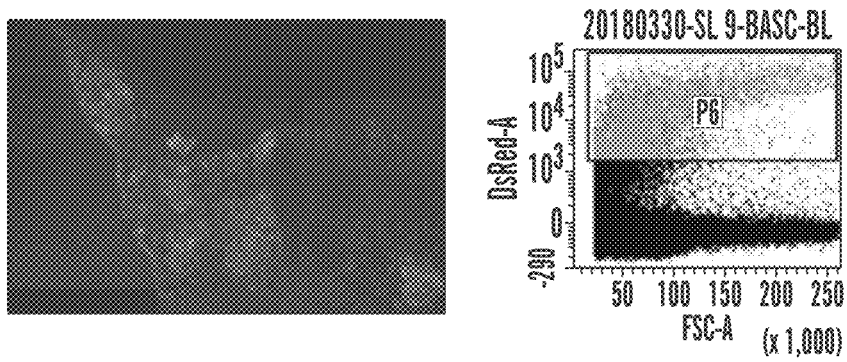

Left, Representative image of recipient mouse lung 6 weeks post-transplantation by fluorescence imaging for DsRed. Right, Representative FACS plot of recipient mouse lung. %DsRed+ cells are gated from DAPI- CD31- CD45- cells.

*FIG. 19 (cont.)*

Representative images of recipient mouse lungs by fluorescence imaging co-stained for indicated markers. Mouse received 1 million Sca1+ organoid cells and lungs were analyzed 2.5 weeks post-transplant.

Representative H&E images of recipient mouse lungs. Mouse received 1 million Sca1+ organoid cells and lungs were analyzed 2.5 weeks post-transplant. Left, 4x image. Right, 20x images.

1. Subcutaneous
Sca1+ organoid cells grow as well-differentiated structures when delivered subcutaneously.

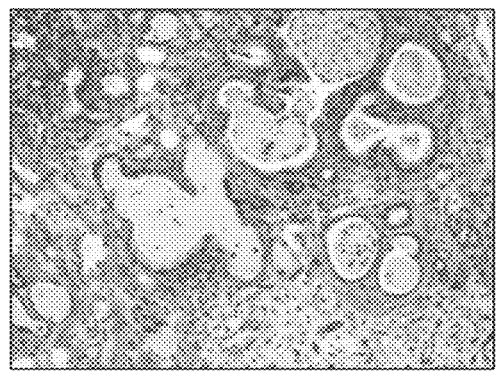

2. Re-isolation of Transplanted Cells and Re-culturing in 3D
Transplanted cells were re-isolated by FACS. When grown in standard 3D co-culture conditions, the engrafted cells yielded well-differentiated organoids with typical nuclei.

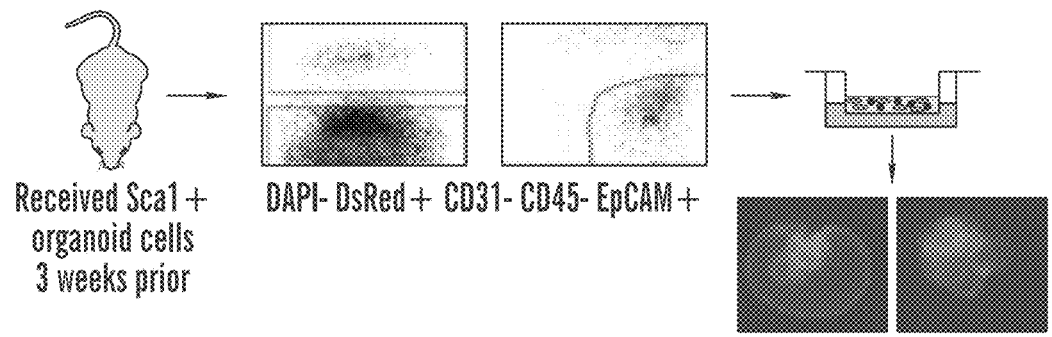

Received Sca1+ organoid cells 3 weeks prior     DAPI- DsRed+ CD31- CD45- EpCAM+

*FIG. 23*

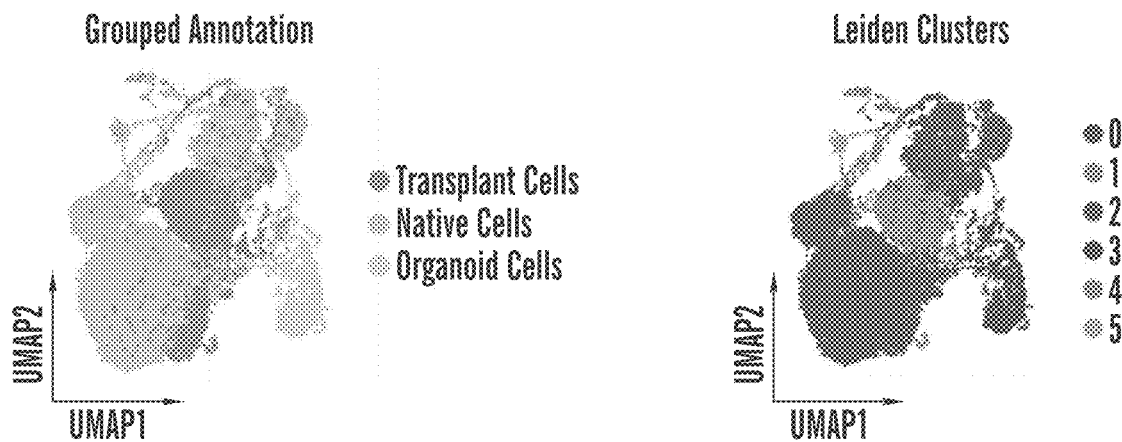
FIG. 27A
FIG. 27B
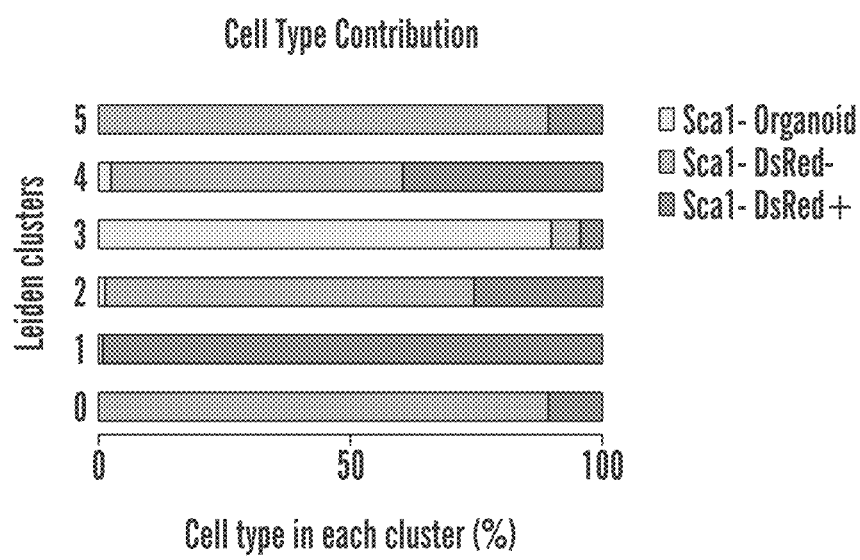
FIG. 27C

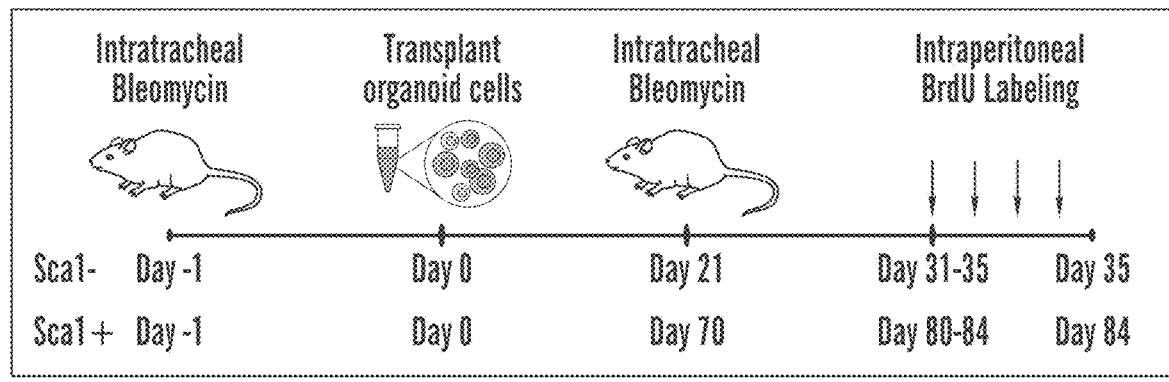
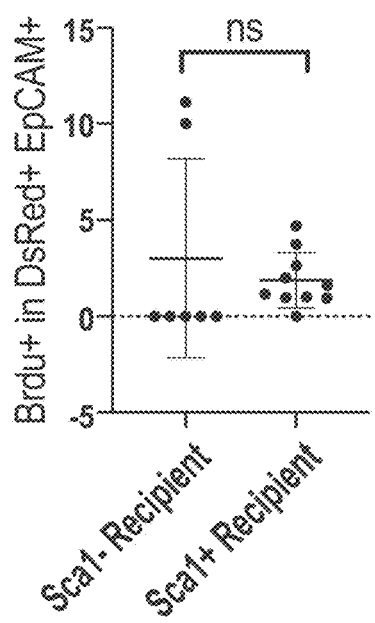
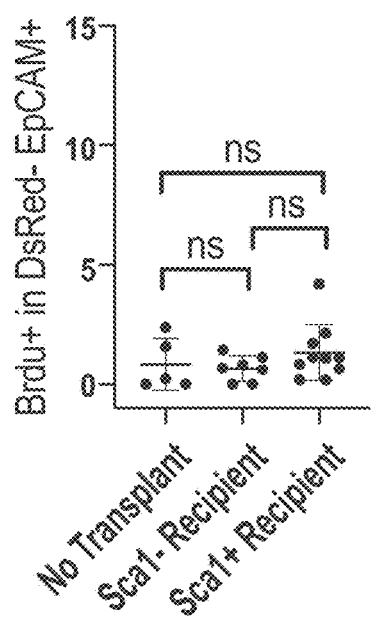
*FIG. 31*

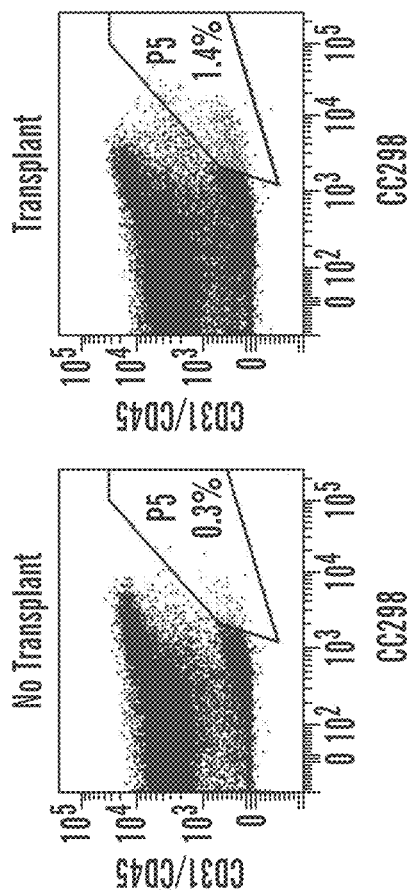
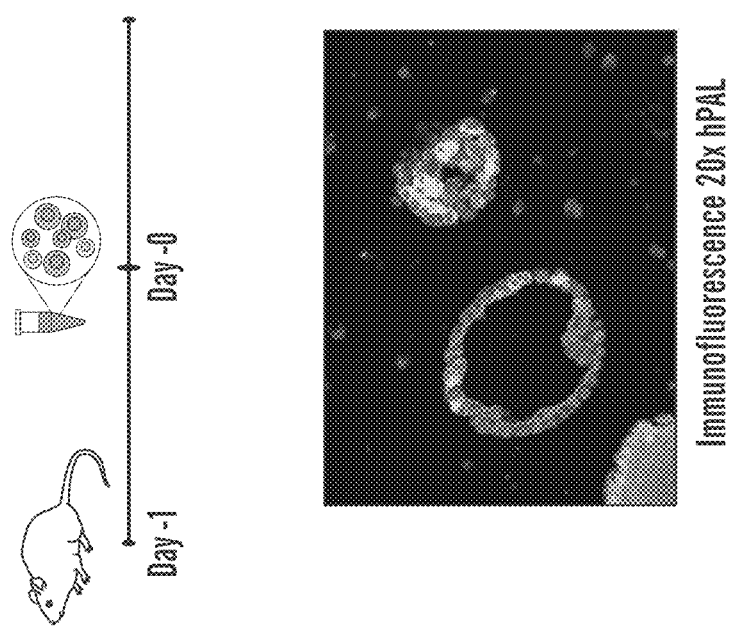
FIG. 35

USE OF ALVEOLAR OR AIRWAY ORGANOIDS FOR THE TREATMENT OF LUNG DISEASES AND DISORDERS

CROSS-REFERENCE TO RELATED APPLICATIONS

This Application is a continuation-in-part application of PCT Application No: PCT/US2020/042961 filed Jul. 22, 2020, which claims benefit under 35 U.S.C. § 119(e) of U.S. Provisional Application No. 62/878,999, filed Jul. 26, 2019, the contents of which are incorporated herein by reference in its entirety.

GOVERNMENT SUPPORT

This invention was made with government support under Grant Numbers HL125821 and HL150876, awarded by the National Institutes of Health. The Government has certain rights in this invention.

FIELD OF THE INVENTION

The technology described herein relates to personalized medicine for the treatment of lung disease or disorders.

SUMMARY OF THE DISCLOSURE

Provided herein are methods and compositions relating to the treatment of lung disease or disorders. In particular, the methods provided herein relate, in part, to the discovery of a particular set of conditions for differentiating lung cells, such as autologous lung cells, into alveolar organoids or airways in vitro. The resulting compositions can be transplanted to the same individual (e.g., autologous transplantation) or to a different individual (e.g., allogeneic transplantation) for the treatment of a given lung disease or disorder. Compositions comprising these alveolar organoids or airway organoids can successfully engraft into lung tissue.

One aspect provided herein relates to a method for treating a lung disease or disorder, or a lung injury in a subject, the method comprising administering to (or transplanting in) a subject, intratracheally, a composition comprising an alveolar organoid, airway organoid, or an isolated cell thereof, wherein the alveolar organoid or airway organoid are produced in vitro or ex vivo from a lung cell by culturing the lung cell in a 3-dimensional culture for a time and under conditions sufficient to produce an alveolar organoid or airway organoid, and wherein the alveolar organoid, airway organoid or cell thereof functionally engrafts into the lung, thereby treating the lung disease or disorder or lung injury in the subject.

Also provided herein, in another aspect is a method for treating a lung disease or disorder, or a lung injury, the method comprising administering to a subject, intratracheally, a composition comprising an alveolar organoid, airway organoid, or an isolated cell thereof, wherein the alveolar organoid or cell thereof is CD31/CD45−, Epcam+ and Sca1−, wherein the airway organoid or cell thereof is CD31/CD45−, Epcam+ and Sca1+, and wherein the alveolar organoid, airway organoid or cell thereof functionally engrafts into the lung, thereby treating the lung disease or disorder or lung injury in the subject.

In one embodiment of any aspect, the alveolar organoid, airway organoid or cell thereof are autologous to the subject to be treated.

In another embodiment of any aspect, the alveolar organoid, airway organoid or cell thereof are heterologous to the subject to be treated.

In another embodiment of any aspect, the alveolar organoid or airway organoid further comprises a lung epithelial cell, or a stromal cell.

In another embodiment of any aspect, the lung cell is isolated from a donor or is derived in vitro from a stem cell.

In another embodiment of any aspect, the stem cell is an induced pluripotent stem cell (iPSC), an embryonic stem cell, or a lung progenitor cell.

In another embodiment of any aspect, the lung cell is isolated from the donor using fluorescence-activated cell sorting (FACS).

In another embodiment of any aspect, the alveolar organoid or airway organoid is a human primary alveolar (hPAL) cell-derived organoid, a human iPSC-derived organoid or a human primary airway (hPAR) cell-derived organoid.

In another embodiment of any aspect, the lung cell is CD31/CD45− and Epcam+.

In another embodiment of any aspect, the lung cell is Sca1+ and wherein the airway organoid derived from the lung cell is Sca1+.

In another embodiment of any aspect, the lung cell is Sca1− and wherein the alveolar organoid derived from the lung cell is Sca1−.

In another embodiment of any aspect, the Sca1+ organoids engraft and populate in the alveolar space.

In another embodiment of any aspect, the Sca1− organoids engraft into regions of the lung having damaged alveolar cells.

In another embodiment of any aspect, the cells of the Sca1− organoids upon engraftment are transcriptionally similar to the corresponding endogenous cells. In another embodiment, the engrafted cells are Keratin 8+.

In another embodiment of any aspect, the engrafted cells are Keratin 8+ and/or Keratin 17+.

In another embodiment of any aspect, the transplanted or engrafted cells retain progenitor function as assessed by (i) their ability to give rise to organoids when returned to in vitro culture and/or (ii) their ability to respond to a second lung injury.

In another embodiment of any aspect, the subject is immunocompromised.

In another embodiment of any aspect, the method further comprises, prior to administering/transplanting, the step of diagnosing a subject as having a lung disease or disorder.

In another embodiment of any aspect, the method further comprises, prior to administering/transplanting, receiving the results of an assay that diagnoses a subject as having a lung disease or disorder.

In another embodiment of any aspect, the method further comprises, prior to administering/transplanting, the step of diagnosing a subject as being immunocompromised.

In another embodiment of any aspect, the method further comprises, prior to administering/transplanting, receiving the results of an assay that diagnoses a subject as being immunocompromised.

Another aspect provided herein relates to a mouse useful for modelling COVID-19 induced lung injury, comprising a recipient mouse having engrafted human primary lung cells or iPS-derived lung cells, wherein the mouse model is made by the process of administering, intratracheally, organoid cells, or an isolated cell thereof, wherein the airway organoid or the alveolar organoid or cell thereof is CD31/CD45−, Epcam+, (+HTII-280+ for alveolar, and +Ngfr+ for airway) and wherein the organoid or cell thereof functionally engrafts into the lung.

In one embodiment of any aspect, the engrafted cells express CD298.

In another embodiment of any aspect, the transplanted or engrafted cells retain progenitor function as assessed by (i) their ability to give rise to organoids when returned to in vitro culture and/or (ii) their ability to respond to a second lung injury.

In another embodiment of any aspect, the mouse (i) is immune compromised (e.g., a nude mouse or a Rag KO mouse), and/or (ii) comprises at least two different human lung cells.

Also provided herein is a method of screening an agent for treatment of COVID-19, the method comprising: (i) contacting the mouse having engrafted human primary lung cells or iPS-derived lung cells as described herein with an effective amount of SARS-CoV-2 to induce a lung injury, (ii) administering a candidate agent to the infected mouse of step (i), and (iii) identifying an agent capable of treating COVID-19 when the degree of lung injury is reduced in the presence of the agent as compared to a reference control.

In one embodiment of any aspect, the reference control is the degree of lung injury prior to administration of the candidate agent.

In another embodiment of any aspect, the reference control is the degree of lung injury in a substantially similar mouse with engrafted human cells that is not contacted with the SARS-CoV-2. In another embodiment, the SARS-CoV-2 is administered by inhalation.

Also provided herein is a transplant composition comprising a human alveolar organoid, wherein the cells of the alveolar organoid are CD31/CD45−, Epcam+ and HTII-280+.

Another aspect provided herein relates to a transplant composition comprising a human airway organoid, wherein the cells of the airway organoid are CD31/CD45−, Epcam+, +/−NGFR+.

In one embodiment of any aspect, the human organoid is an alveolar organoid, a bronchiolar organoid or a bronchoalveolar organoid.

Another aspect described herein provides a method of promoting a population of lung cells to differentiate into alveolar organoids (e.g., CD31/CD45−, Epcam+, Sca1−), comprising culturing the population of lung cells in a Basic 3D medium for a sufficient amount of time to allow the lung cells to differentiate into alveolar organoids. Alternatively, the medium can be CK-DCI medium for promoting iPSC-alveolar organoids.

Another aspect described herein provides a method of promoting a population of lung cells to differentiate into airway organoids (e.g., CD31/CD45−, Epcam+, and Sca1+), comprising culturing the population of lung cells in a Basic 3D medium for a sufficient amount of time to allow the lung cells to differentiate into alveolar organoids. Alternatively, the medium can be CK-DCI medium for promoting iPSC-alveolar organoids.

In one embodiment of any aspect, the lung cell is a type I alveolar cell, or a type II alveolar cell. In one embodiment of any aspect, the lung cell is differentiated from induced pluripotent stem cells (iPSC) or embryonic stem cells.

In one embodiment of any aspect, the population of lung cells are co-cultured with a second population of lung cells. In one embodiment of any aspect, the second population of lung cells comprise a cell type selected from the group consisting of: stromal cell, epithelial cell, endothelial cell, mesenchymal cell, fibroblast cell, smooth muscle cell, ciliated cell, and goblet cell.

In one embodiment of any aspect, the second population of cells is a substantially pure population.

In one embodiment of any aspect, the population of lung cells and second population of cells are co-cultured on an air/liquid interface. In one embodiment of any aspect, the lung cells and the second population of cells are co-cultured in a gelatinous protein mixture. In one embodiment, the gelatinous protein mixture is a gelatinous protein mixture secreted by Engelbreth-Holm-Swarm mouse sarcoma cells, also known by the trade name Matrigel™.

In one embodiment, the organoids express at least one airway marker, such as acetylated alpha-tubulin.

In one embodiment of any aspect, the Basic 3D medium comprises one or more of: DMEM, insulin-transferrin-selenium (ITS), fetal bovine serum (FBS), at least one antibiotic, HEPES, and/or L-glutamine. In one embodiment of any aspect, the at least one antibiotic is penicillin or streptomycin.

In one embodiment of any aspect, the iPSC cell or population thereof is/are derived from a subject with a pulmonary disease or disorder. In one embodiment, the iPSC cell or population thereof is autologous to the subject in which the alveolar organoids are intended for transplantation. In another embodiment, the iPSC cell or population thereof is allogeneic with respect to the subject for which the alveolar organoids are intended for transplantation.

In one embodiment of any aspect, the lung disease or disorder can be any of: Surfactant protein deficiency, Hermansky-Pudlak syndrome, Idiopathic Pulmonary fibrosis, Pulmonary fibrosis, Chronic obstructive pulmonary disease (COPD), Emphysema, Chronic bronchitis, Pneumonia, Asthma, Sarcoidosis, Pleural effusion, Pleurisy; Bronchiectasis, Lymphangioleiomyomatosis (LAM), Cystic fibrosis, Interstitial lung disease, Lung cancer, Tuberculosis, Acute respiratory distress syndrome (ARDS), Infant respiratory distress syndrome (IRDS), Coccidioidomycosis, Histoplasmosis, Hypersensitivity pneumonitis (allergic alveolitis), Influenza (flu), Mesothelioma, Pertussis (whooping cough), Pulmonary hypertension, Pulmonary embolism, Pulmonary edema, Pulmonary alveolar proteinosis, Pulmonary contusion, Pulmonary alveolar microlithiasis, Severe acute respiratory syndrome (SARS), and Pneumothorax, bronchopulmonary dysplasia, pneumoconiosis, alpha-1 antitrypsin deficiency, asbestosis, bronchiolitis, byssinosis, cryptogenic organizing pneumonia, or primary ciliary dyskinesia.

In another embodiment, the methods and composition described herein are used to treat at least one symptom or outcome of a lung disease or disorder, such as shortness of breath, fibrosis of lung tissue, reliance on oxygen supplementation, number of hospitalizations, length of hospital stay, length of stay in intensive care unit, need for ventilator, exercise tolerance, pain, coughing frequency or intensity etc.

In one embodiment of any aspect, the population of lung cells is differentiated from an iPSC or ESC or a primary adult lung progenitor cell, and is genetically modified. For example, in one embodiment, the iPSC or ESC or a primary adult lung progenitor cell is genetically modified prior to differentiation into the lung cells to be used in the methods of preparing alveolar organoids as described herein.

In one embodiment of any aspect, the lung cell is differentiated from an iPSC or ESC or a primary adult lung progenitor cell derived from a subject having a lung disease or disorder, and is genetically modified.

In one embodiment, the methods provided herein are performed in vitro.

In one embodiment, it is specifically contemplated herein that the methods and compositions provided herein are not performed using any human embryonic source of cells.

Another aspect described herein provides a method of isolating an alveolar cell from an alveolar organoid as described herein, the method comprising: (a) contacting an alveolar organoid produced by the methods described herein with dispase for a sufficient amount of time to allow for the gelatinous protein mixture to dissolve; (b) centrifuging the material of step (a) to isolate the alveolar organoid from supernatant; (c) contacting the isolated alveolar organoid or step (b) with trypsin for a sufficient amount of time to isolate the alveolar cells from the second population of lung cells; and (d) resuspending the alveolar cells of step (c) in a suitable buffer. As will be readily appreciated by those of skill in the art, the amount of time for the treatment with dispase or trypsin should not be so long as to adversely affect viability of the cells to be isolated. Thus, in some embodiments, the method does not result in the death of more than 50% of the cells to be isolated, for example, less than 40% cell death, less than 30%, less than 25%, less than 20%, less than 10%, less than 5%, less than 2%, less than 1% or more (i.e., no substantial cell death or no discernable loss of cell viability using standard methods).

Another aspect described herein provides a composition comprising any of the organoids (e.g., alveolar organoids) or populations of isolated alveolar cells described herein.

In one embodiment of any aspect, the compositions provided herein further comprise a pharmaceutically acceptable carrier.

In one embodiment of any aspect, the lung cell population or isolated alveolar cells are a substantially pure population.

Another aspect described herein provides a method of treating a lung disease or disorder, the method comprising transplanting any of the alveolar organoids, isolated alveolar cells or population thereof, or the compositions described herein to a subject in need thereof.

In one embodiment of any aspect, the step of transplanting is performed via intratracheal delivery.

In one embodiment of any aspect, the step of transplanting results in engraftment of the alveolar organoid, the isolated alveolar cell or population thereof, or the composition.

In one embodiment of any aspect, engraftment of the cells in the administered composition occurs in the trachea, lung parenchyma, bronchioles, respiratory bronchioles, alveolar ducts, alveolar sacs, alveoli, pulmonary acinus, pulmonary lobule, lower respiratory tract, upper respiratory tract, left lung, and/or right lung.

In one embodiment of any aspect, the subject to be treated is immunocompromised.

In one embodiment of any aspect, the method further comprises, prior to transplanting, the step of diagnosing a subject as having a lung disease or disorder.

In one embodiment of any aspect, the method further comprises, prior to transplanting, receiving the results of an assay that diagnoses a subject as having a lung disease or disorder.

In one embodiment of any aspect, the method further comprises, prior to transplanting, a step of diagnosing a subject as being immunocompromised.

Another aspect described herein provides a method of treating a lung disease or disorder in a subject, the method comprising: (a) obtaining a iPSC and differentiating the iPSC to a lung cell and optionally expanding the lung cells; (b) culturing the lung cell of step (a) in a Basic 3D medium, or CK-DCI medium for iPSC-derived organoids, for a sufficient amount of time to allow the lung cell to differentiate into alveolar organoids; and (c) transplanting the alveolar organoid or an isolated cell population thereof of step (b) via intratracheal delivery in a subject in need thereof, wherein transplanting results in engraftment.

Another aspect described herein provides a method of treating a lung disease or disorder in a subject, the method comprising: (a) obtaining a iPSC and differentiating the iPSC to an alveolar cell; and (b) transplanting the alveolar cell or population thereof of step (a) via intratracheal delivery in a subject in need thereof, wherein transplanting results in engraftment of the alveolar cell.

In one embodiment of any aspect, the method further comprises, prior to step (b), the step of genetically modifying the lung cell or the iPSC or ESC cell from which it is derived.

In one embodiment of any aspect, the method further comprises, prior to step (b), the step of genetically modifying the alveolar cell.

In one embodiment of any aspect, the method further comprises, administering an immunosuppressive agent prior to, or substantially at the same time as the transplantation.

In one embodiment of any aspect, the subject is immunocompromised.

Another aspect described herein provides a method of promoting a population of lung cells to differentiate into alveolar/airway organoids, comprising culturing the population of lung cells in a Basic 3D medium for a sufficient amount of time to allow the lung cells to differentiate into organoids comprising alveolar and airway cells.

In one embodiment of any aspect, wherein the population of lung cells comprise alveolar cells and bronchiolar cells.

Another aspect described herein provides a method of isolating alveolar and airways cells from an alveolar/airway organoid described herein, the method comprising: (a) contacting an alveolar/airway organoid as described herein with dispase for a sufficient amount of time to allow for the gelatinous protein mixture to dissolve; (b) centrifuging the material of step (a) to isolate the alveolar/airway organoid from supernatant; (c) contacting the isolated alveolar/airway organoid from step (b) with trypsin for a sufficient amount of time to isolate the alveolar and airway cells from the second population of lung cells; and (d) resuspending the alveolar and airway cells of step (c) in a suitable buffer.

Another aspect described herein provides a composition comprising any alveolar/airway organoid or a population of isolated alveolar and airway cells described herein.

Another aspect described herein provides a method of treating a lung disease or disorder, the method comprising transplanting any of the alveolar/airway organoids, any isolated alveolar and airway cell or population thereof, or any composition described herein to a subject in need thereof.

In one embodiment of any aspect, transplanting results in engraftment of the airway cells of the alveolar/airway organoid, the isolated alveolar and airway cells population, or the composition.

In one embodiment of any aspect, engraftment of airway cells occurs in the trachea, lung parenchyma, bronchioles, respiratory bronchioles, alveolar ducts, alveolar sacs, alveoli, pulmonary acinus, pulmonary lobule, lower respiratory tract, upper respiratory tract, left lung, and/or right lung.

Another aspect described herein provides a method of treating a lung disease or disorder in a subject, the method comprising: (a) obtaining a iPSC and differentiating the iPSC to a lung cell; (b) culturing the lung cell of step (a) in CK-DCI for a sufficient amount of time to allow the lung cells to differentiate into alveolar/airway organoids comprising alveolar and airway cells; and (c) transplanting the alveolar and airway organoid or an isolated cell population thereof of step (b) via intratracheal delivery in a subject in need thereof, wherein transplanting results in engraftment of the airway cells.

In one embodiment of any aspect, the method further comprises, prior to step (b), the step of genetically modifying the lung cell or the iPSC or ESC from which the lung cell is derived.

In one embodiment of any aspect, the method further comprises administering at least one immunosuppressive therapeutic. Exemplary immunosuppressive therapeutics can include, but are not limited to, prednisone, budesonide, prednisolone, tofacitinib, cyclosporine, tacrolimus, sirolimus, everolimus, azathioprine, leflunomide, mycophenolate, abatacept, adalimumab, anakinra, certolizumab, etanercept, golimumab, infliximab, ixekizumab, natalizumab, rituximab, secukinumab, tocilizumab, ustekinumab, vedolizumab, basiliximab, or daclizumab. In certain embodiments, the immunosuppressive therapeutic is selected from a class of therapeutics including, but not limited to, corticosteroids (e.g., prednisone), Janus kinase inhibitors (e.g., tofacitinib), calcineurin inhibitors (e.g., cyclosporine), mTOR inhibitors (e.g., sirolimus), IMDH inhibitors (e.g., azathioprine), biologic immunosuppressives (e.g., abatacept), or immunosuppressive monoclonal antibodies (e.g., basiliximab).

In one embodiment of any aspect, the method further comprises administering at least one additional therapeutic for the lung disease or disorder.

Another aspect described herein provides a method of increasing the efficiency of engraftment of an alveolar cell following an alveolar cell transplant, the method comprising co-administering an immunosuppressant agent with the transplantation.

In one embodiment of any aspect, the immunosuppressant agent inhibits T cells.

In one embodiment of any aspect, the immunosuppressant agent is administered prior to, during, or after the transplant.

In one embodiment of any aspect, the genetic modification is a nucleotide modification in a disease gene. In one embodiment of any aspect, the nucleotide modification is a nucleotide deletion, insertion, or base substitution. In one embodiment of any aspect, the disease gene is CFTR or HPS1. In one embodiment, the genetic modification comprises modifying or correcting a nucleotide associated with disease to the same nucleotide as in a non-diseased individual or population of individuals.

BRIEF DESCRIPTION OF THE FIGURES

FIG. 2 shows characteristics of known cell types and mouse models (mouse strains) used for studying pulmonary disease.

FIG. 3 shows an exemplary experimental design for lung organoid cell transplantation. The exemplary experimental design includes (1) growing lung organoid cells from B-actin DsRed mice, sorting for two types of lung epithelial cells based on the presence or absence of marker Sca1, and mixing them with lung stromal cells in a mixture of growth factor reduced Matrigel™ and media in a transwell dish; (2) pre-conditioning of recipient mice by administering a single dose of bleomycin intratracheally one day before transplantation of the organoid cells intratracheally—the organoid cells are delivered as single-cell suspension into the lungs; and (3) analyze the recipient's lungs after 2+ weeks later.

FIG. 8A shows data indicating that Sca1+ organoid cells engraft in all immune deficient mouse models tested and that organoid cell engraftment may be dependent on immune cells. FIG. 8B shows data indicating that Sca1+ derived organoid cells engraft in both wildtype (C57BL6 mice) and immune compromised mice (Nude mice and Rag KO mice), however Sca1− derived organoid cells engraft only in immune compromised mice and not in WT C57BL6 mice. Both Nude and Rag knockout (KO) mice lack mature T cells, thus indicating that T cells can be involved in this phenotype. FIG. 8C shows experimental data from a study designed to assess the relevance of T cells in engraftment of organoid cells in wildtype mice. C57BL6 mice were depleted of CD-4 and CD-8 T cells. Flow cytometry was inconclusive whether T cell depletion is enough to permit engraftment of Sca1− organoid cells in wildtype mice. The histology results confirm that some SPC expressing donor cells engraft into the lungs of T cell depleted mice.

FIG. 10A shows data indicating that engraftment of Sca1− organoid cells is better in immune deficient mouse models as compared to the engraftment in C56BL/6. FIG. 10B shows data relating to Sca1+ derived organoid cells and their ability to engraft and populate the airway and alveolar space. When Sca1+ derived organoid cells were delivered to nude of Rag KO mice (both immune compromised), 66.6% of the recipient mice show donor cell engraftment into the alveolar space only. 33.3% of the recipients show engraftment of organoid cells in both the airway and alveolar spaces. The donor cells are DsRed+. The other markers visualized include SPC (an alveolar type 2 marker), Sox2, CCSP, p63 (airway markers), Nkx2.1 (lung lineage marker), and Ac-Tub (ciliated cell marker). Donor cells that engrafted into the airway express various airway markers and ciliated cell markers, consistent with endogenous cells. Donor cells that engraft into the alveolar space also express airway markers, which is inconsistent with endogenous cells.

FIG. 12A shows representative immunofluorescence images of Sca1− organoid cells engrafted in immune deficient mouse models. FIG. 12B shows data indicating that Sca1− derived organoid cells engraft and populate the alveolar space. When Sca1− derived organoid cells are delivered to nude or Rag KO mice (both immune compromised), 100% of the recipient mice show donor cell engraftment into the alveolar space. None of the recipients show any engraftment of Sca1− organoid cells in the airway space. Donor cells are DsRed+; surfactant protein C (SPC)

is a marker of alveolar type 2 (AT2) cells. Some donor cells co-express SPC and the donor cells engraft in the same punctate pattern of SPC cells as AT2 cells in a normal lung, indicating that the donor cells are likely functional. H&E staining for engrafted cells and endogenous lung cells are indistinguishable.

FIG. 13 shows data indicating that transplanted DsRed+ EpCAM+ cells from nude mice can generate alveolar organoids when re-isolated.

Figure 1:
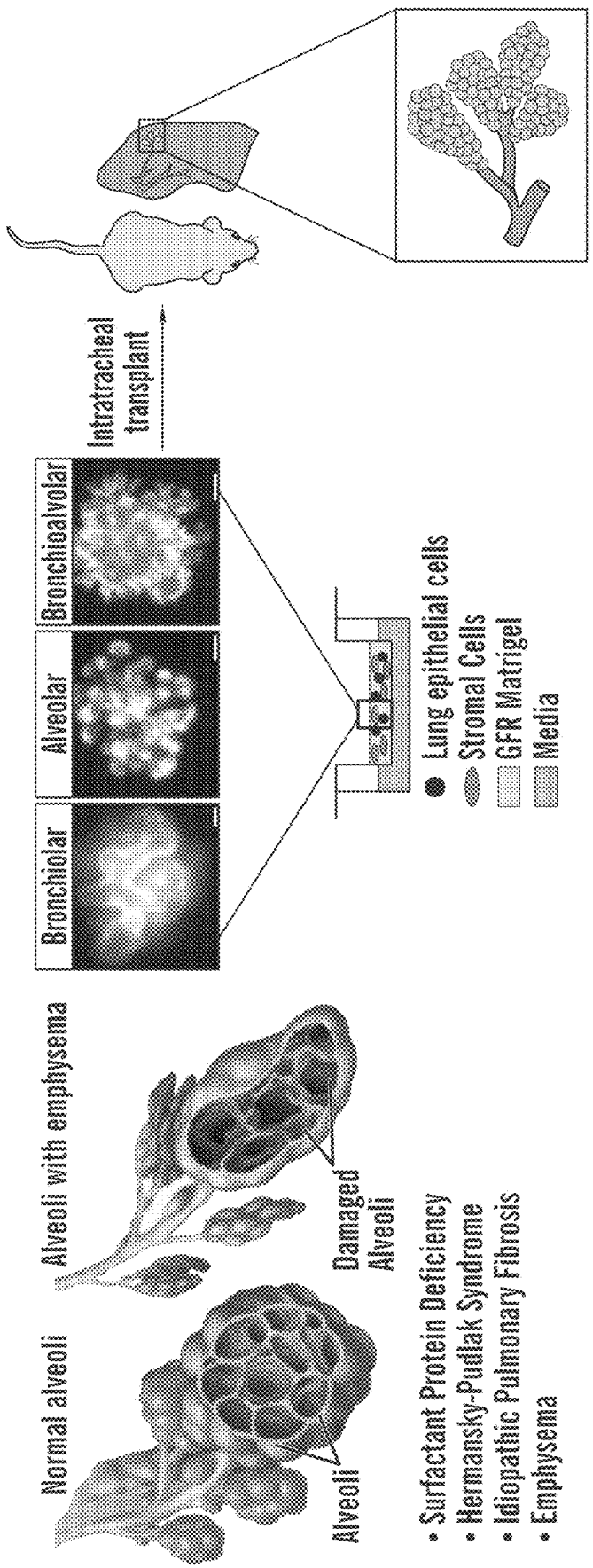
FIG. 1 shows an exemplary approach of developing a transplantation protocol for treatment of pulmonary disease or disorders.
Figure 4:
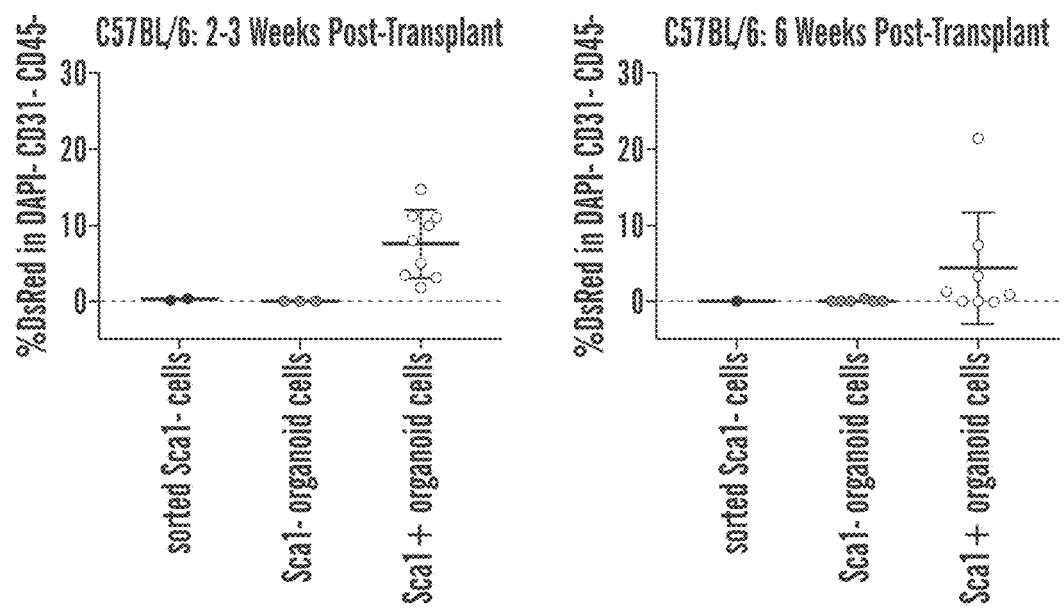
FIG. 4 shows data indicating that Sca1+ organoid cells have higher engraftment rates compared to Sca1− organoid cells and sorted Sca1− cells in C57BL/6 mice.
Figure 5:
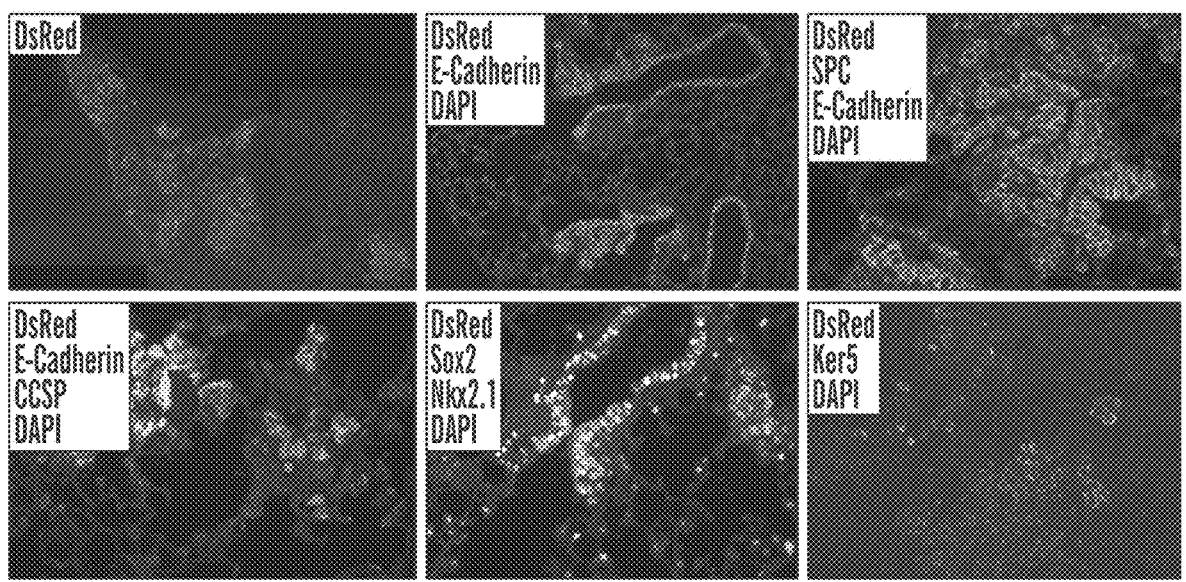
FIG. 5 shows representative immunofluorescence images of Sca1+ organoid cell transplant lungs in C57BL/6.
Figure 6:
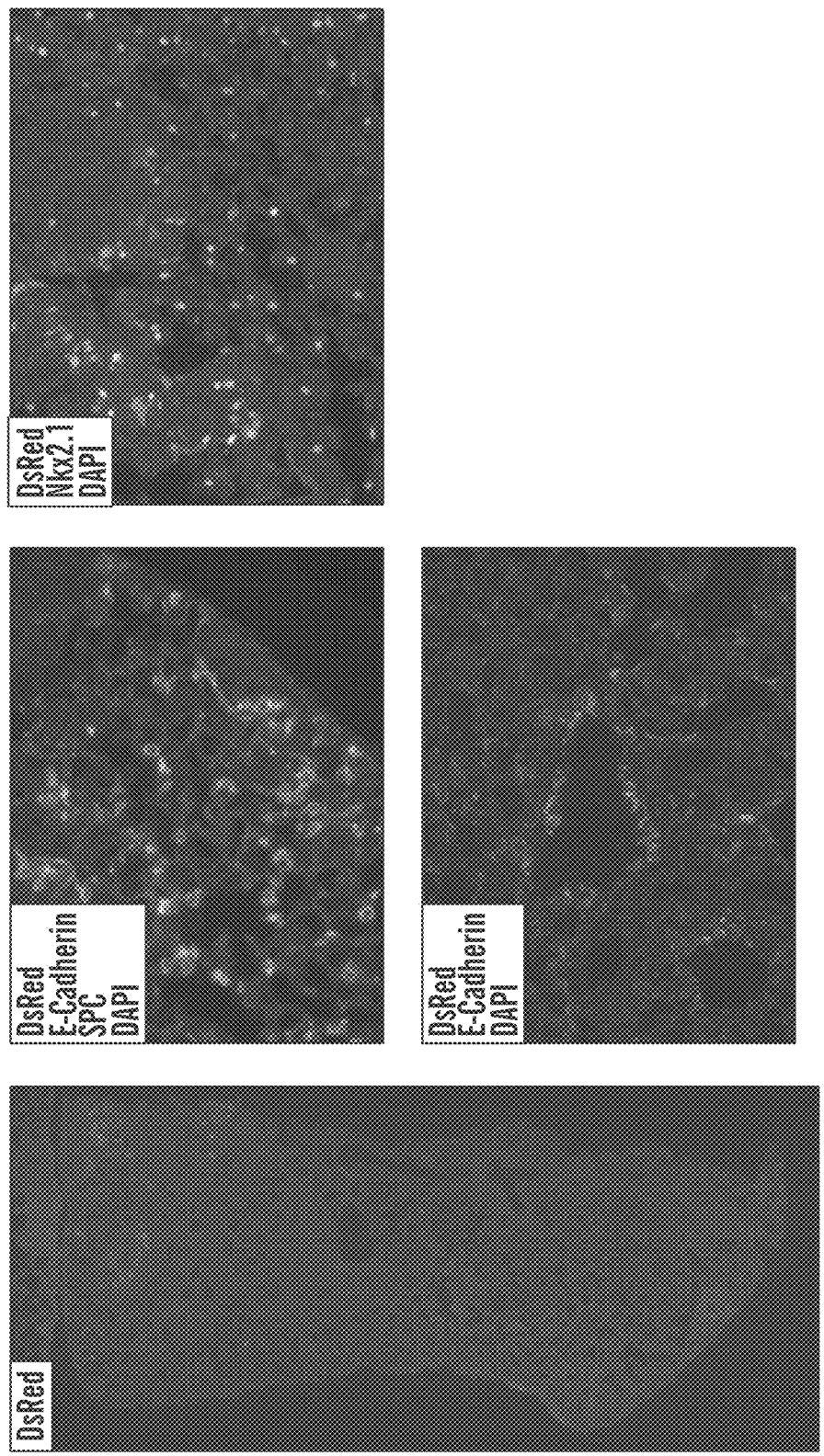
FIG. 6 shows representative immunofluorescence images of Sca1− organoid cell transplant lungs in C57BL/6.
Figures 7, 8A:
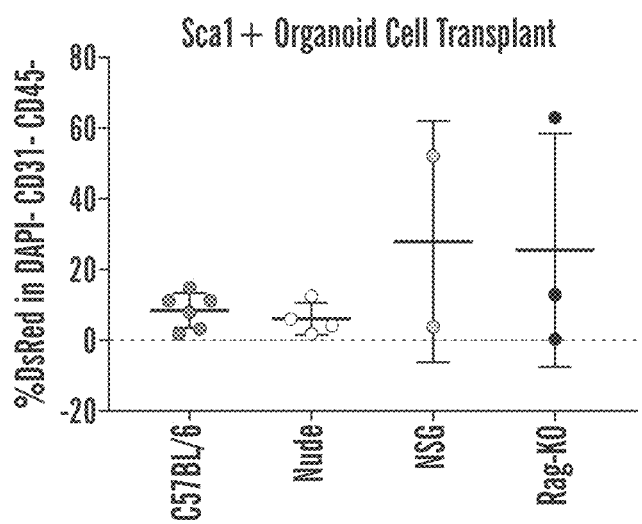
FIG. 7 shows characteristics of immune deficient mouse models.
FIGS. 8A-8C.
Figure 8B:
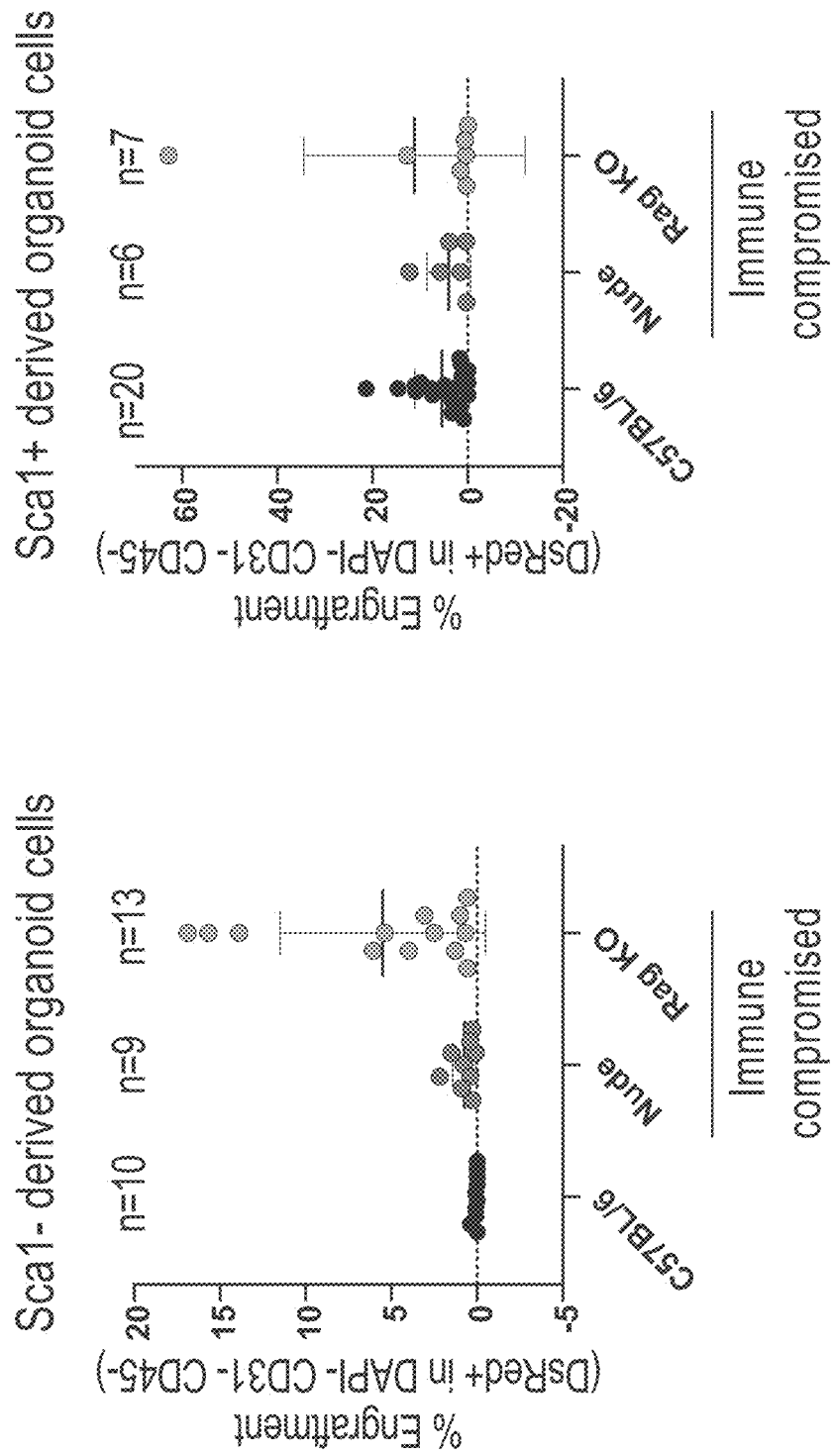
Figure 8C:
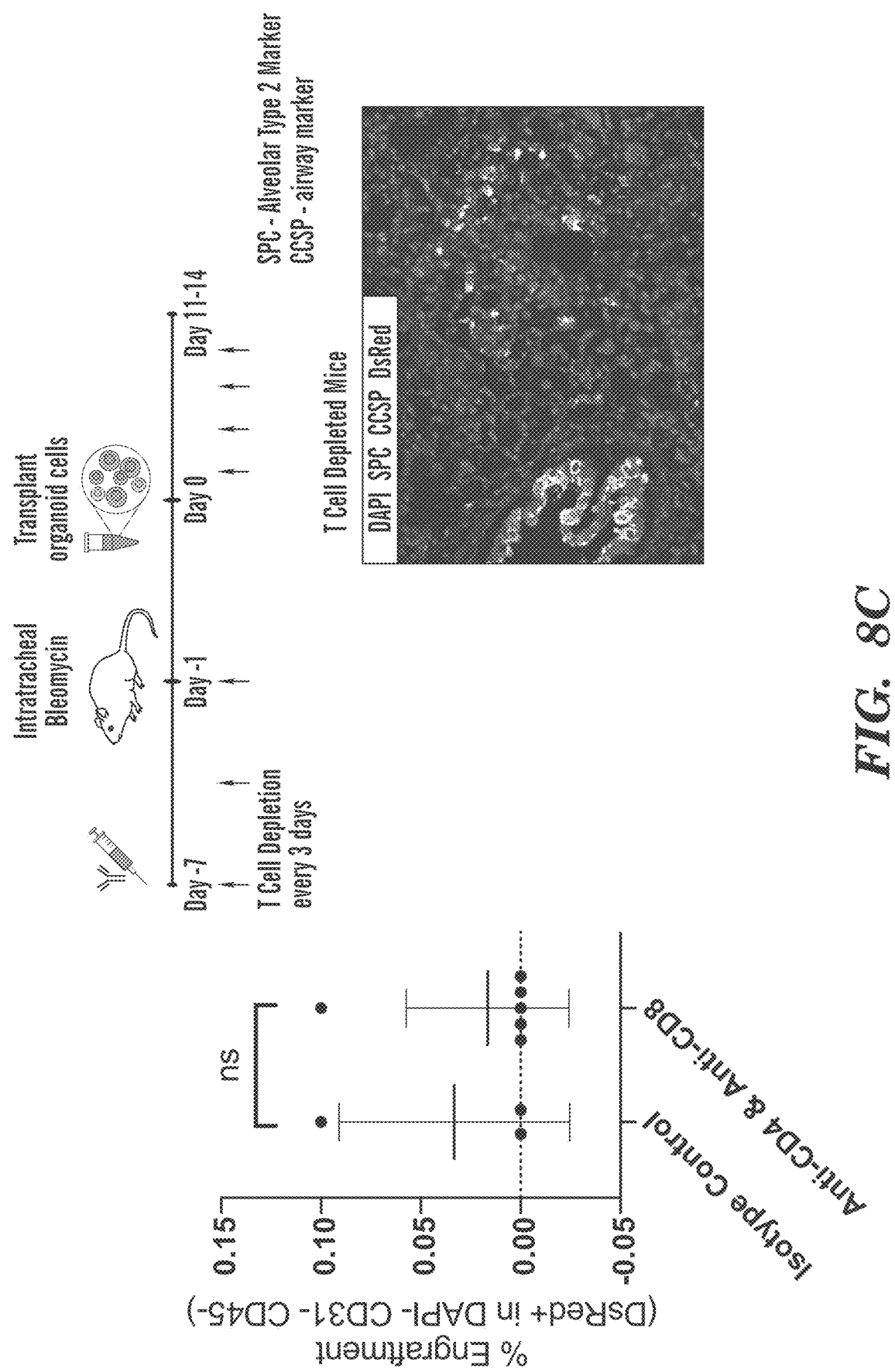
Figure 9:
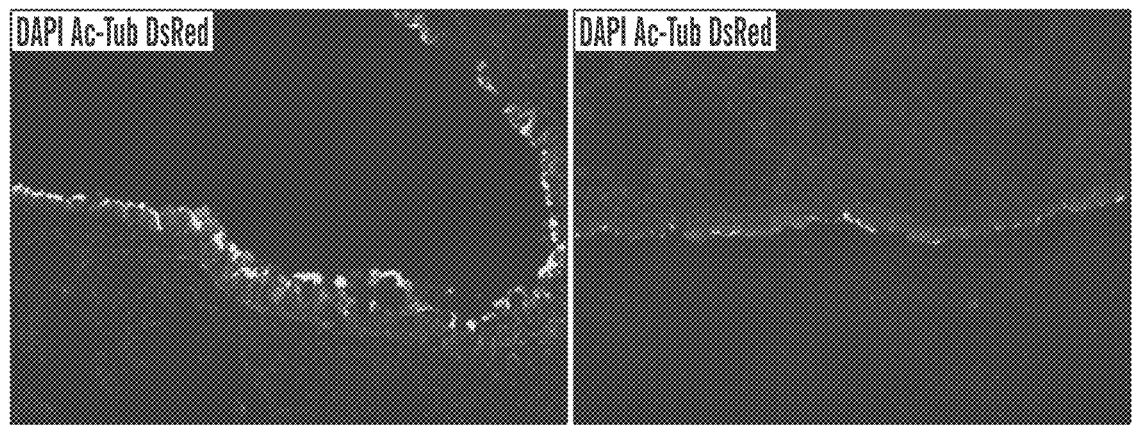
FIG. 9 shows representative immunofluorescence images relating to the engraftment of Sca1+ organoid cells in airways of immune deficient mouse models and the expression of ciliated cell markers.
Figure 10A:
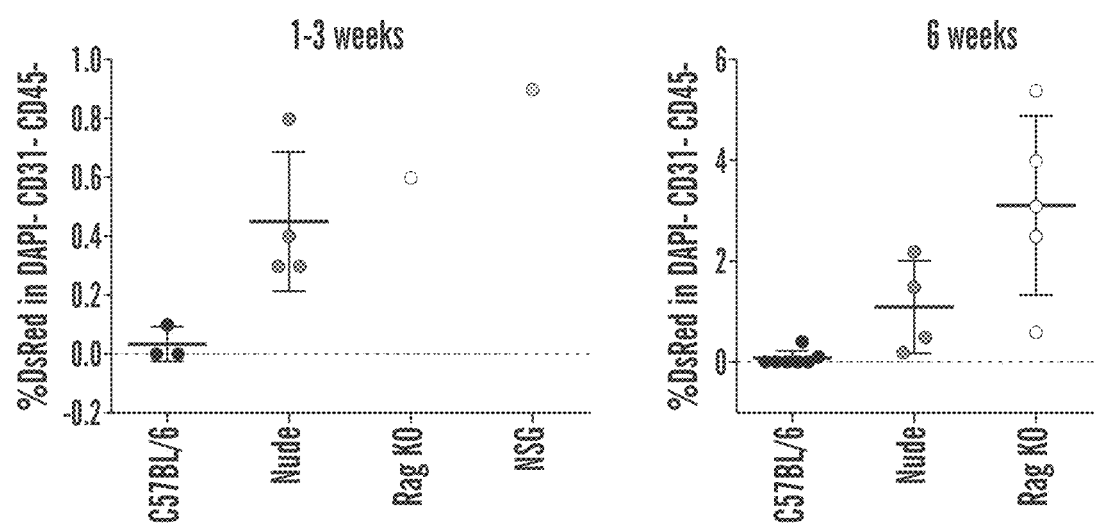
FIGS. 10A-10B.
Figure 10B:
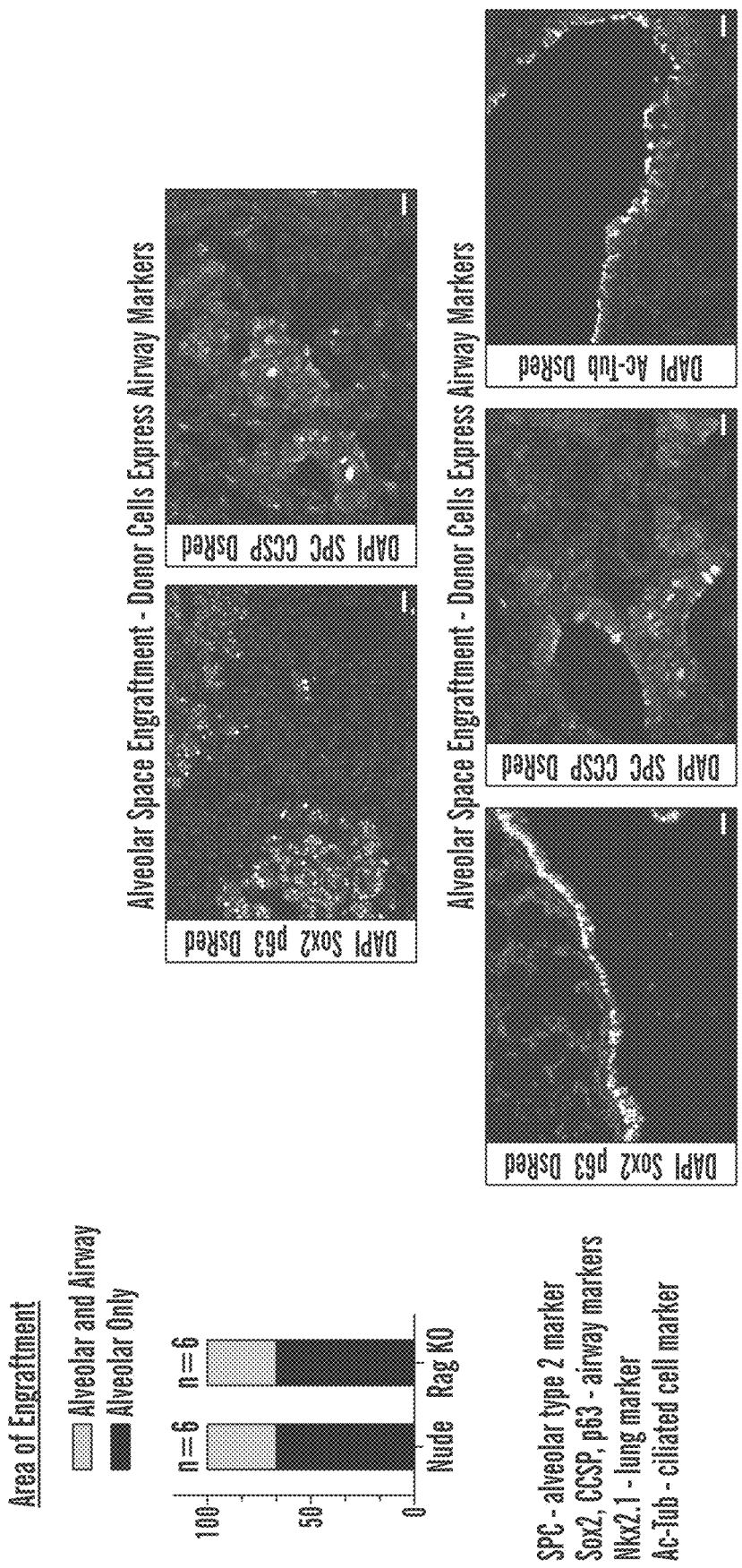
Figure 11:
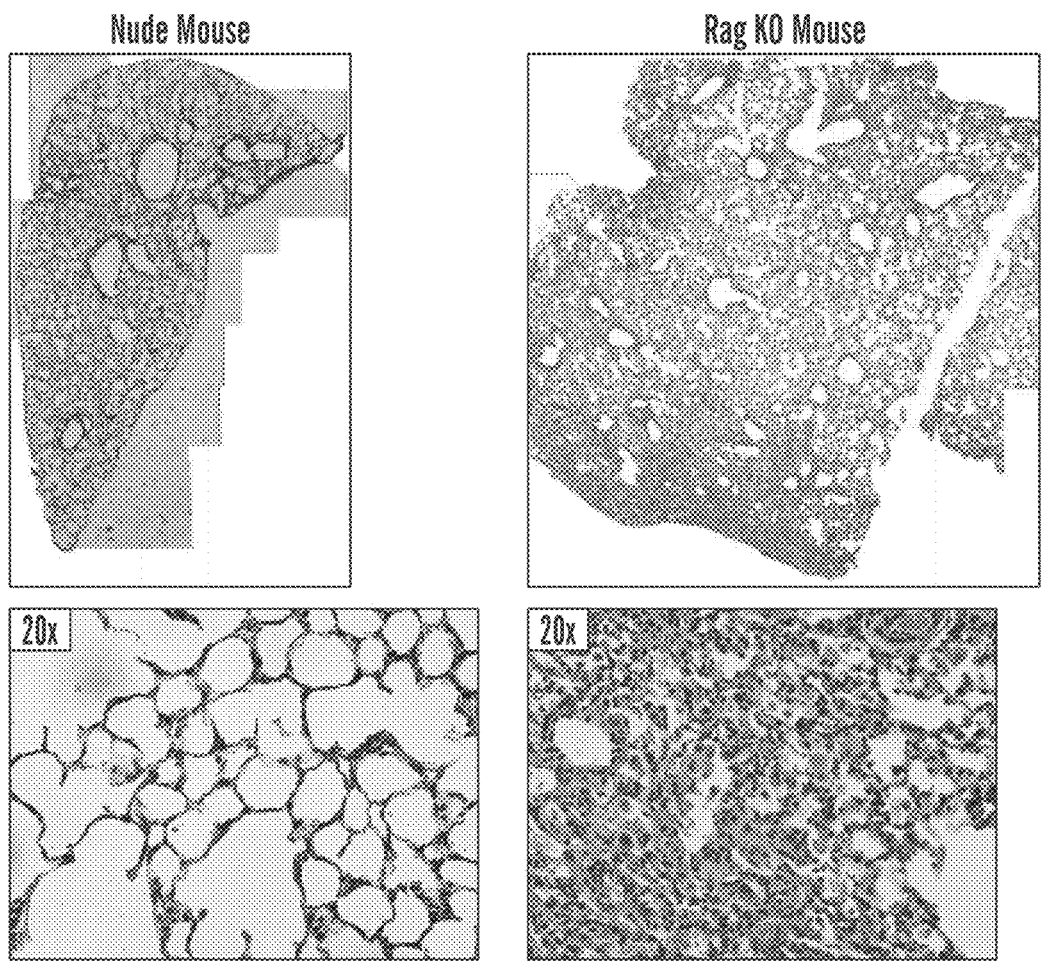
FIG. 11 shows data indicating that Sca1− organoid cell transplant lungs are relatively healthy in immune deficient mice.
Figure 12A:
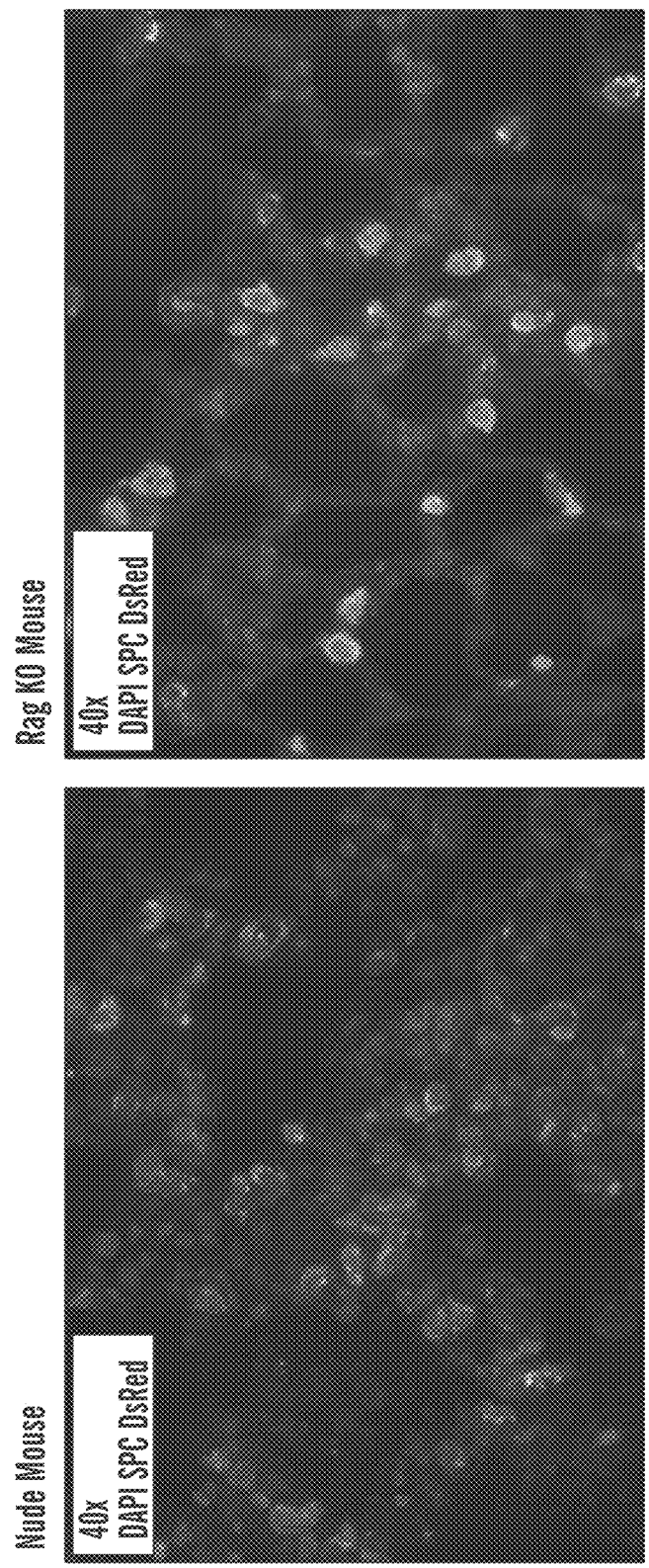
FIGS. 12A-12B.
Figure 12B:
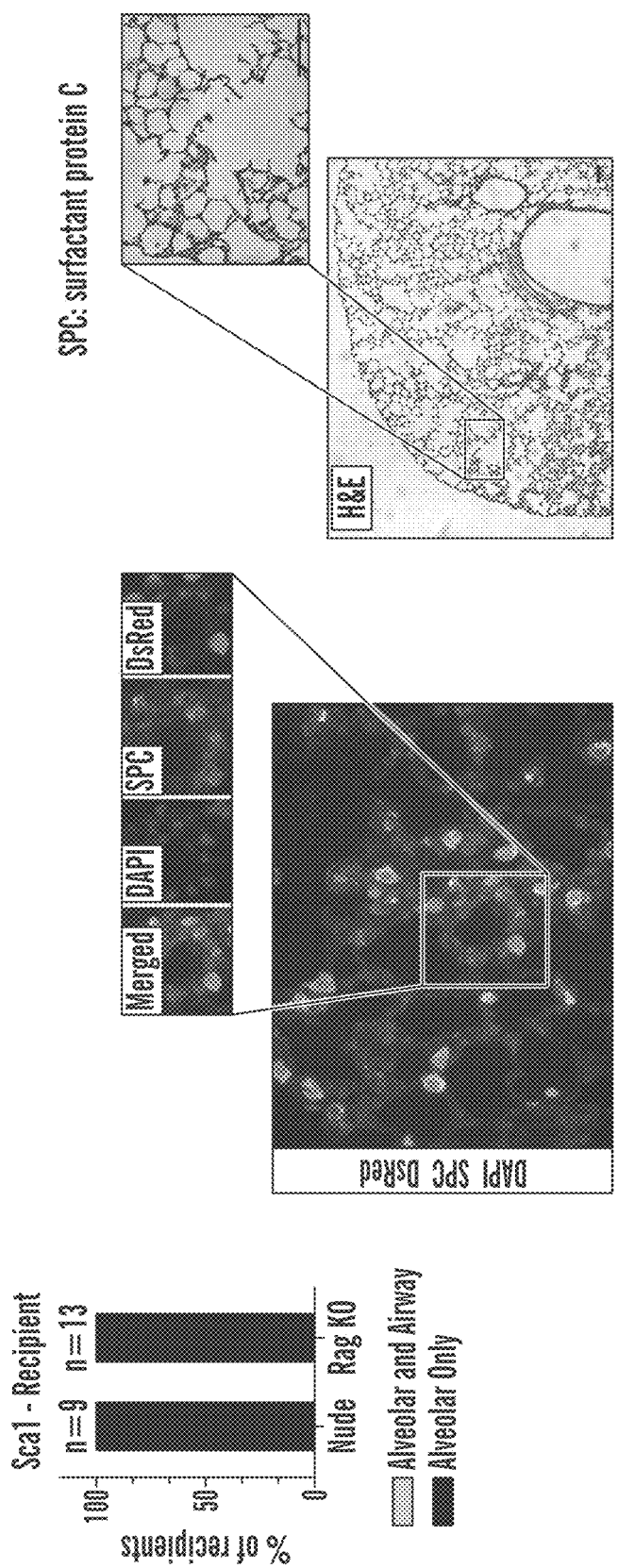
Figure 14:
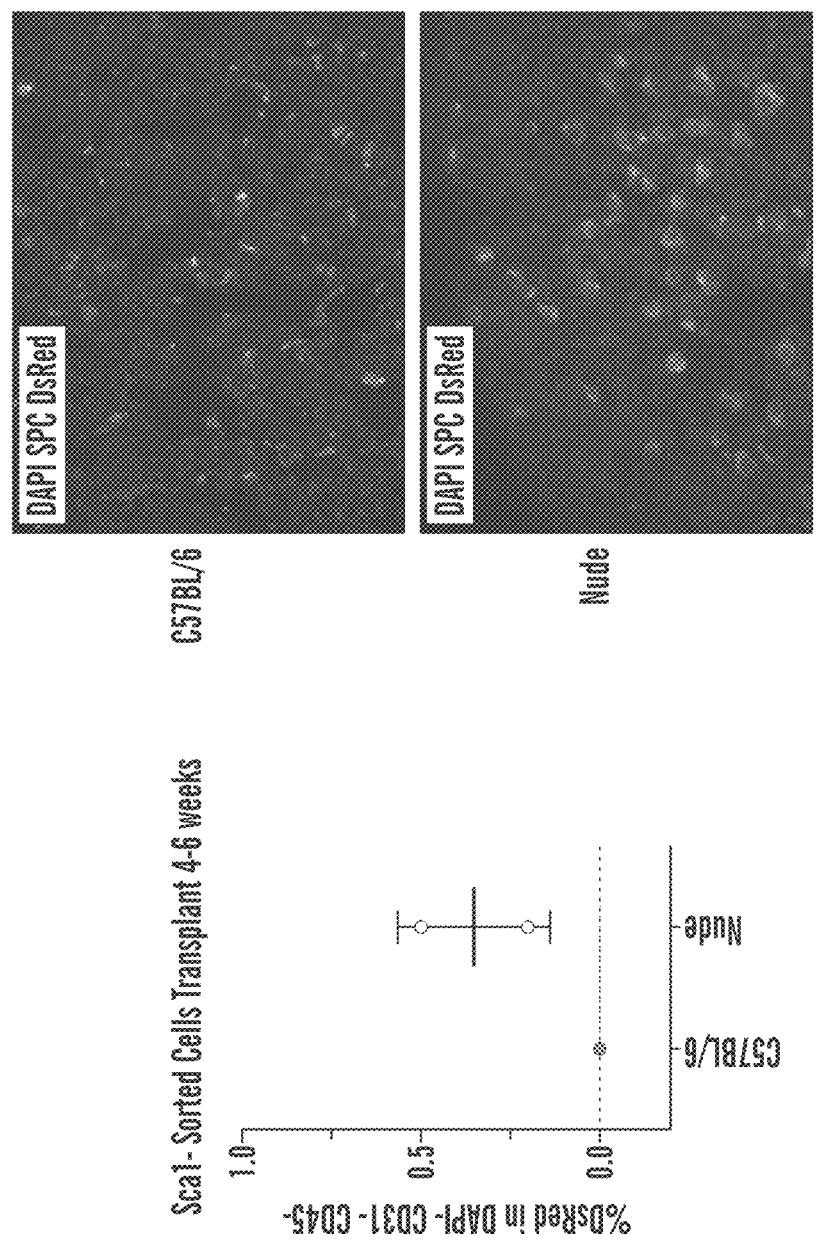

FIG. 14 shows data indicating that sorted Sca1− cell transplants engraft better in nude mice as compared to C56BL/6 mice.

FIG. 15 shows an exemplary schematic of making 3D basal cell organoids.

FIG. 16 shows data indicating that basal cells can engraft in C57BL/6 and immune deficient mice.

FIG. 17 shows representative immunofluorescence images of basal cell transplant lungs in NSG mice.

Figure 18:
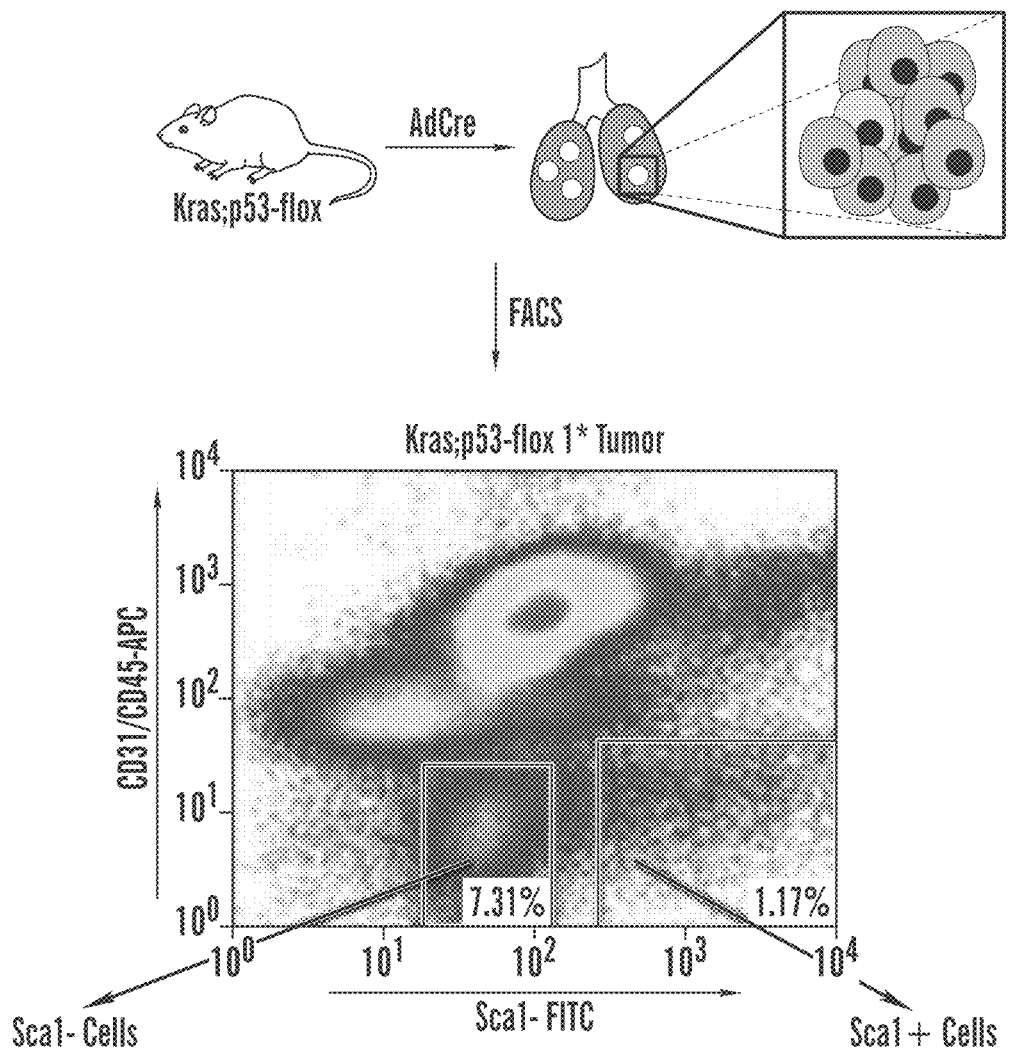

FIG. 18 shows an exemplary method of tumor-propagating cell transplantation (TPCs).

Figure 19:
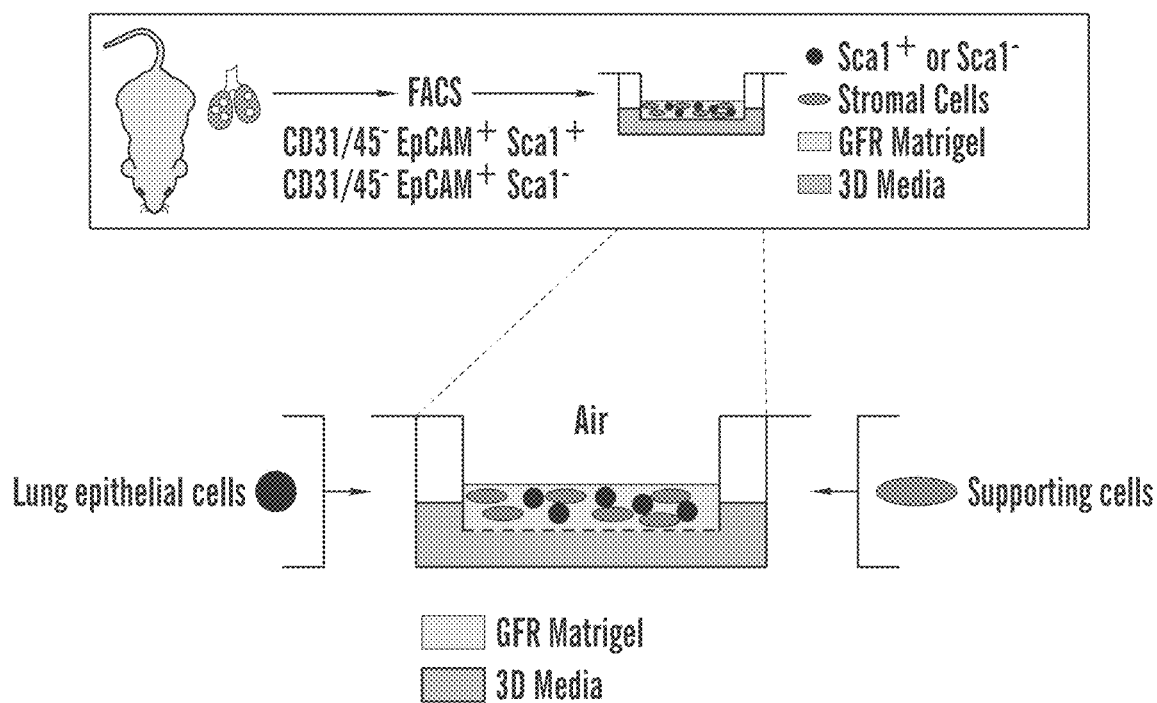
Figure 19:
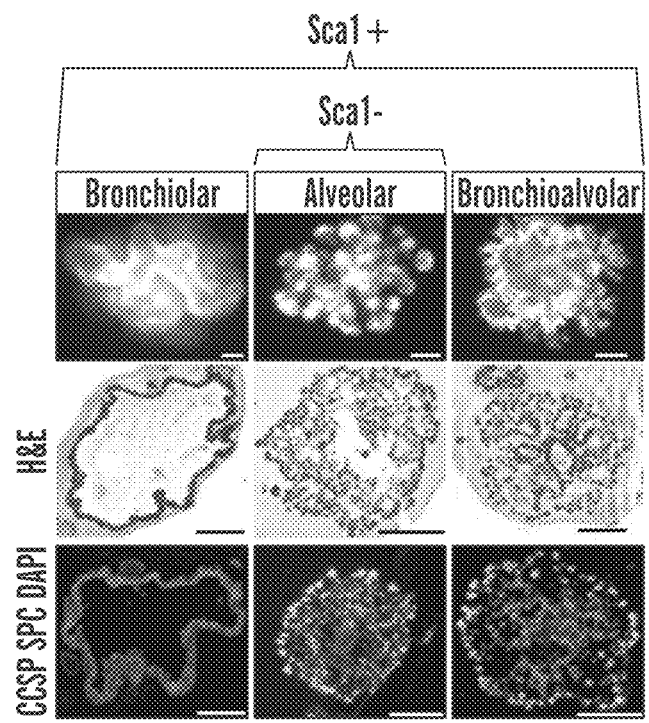

FIG. 19 shows an exemplary method of generating airway organoid cells and transplanting them into recipient mice. In addition, FIG. 19 shows data relating to a C57BL/6 bleomycin lung injury model and transplantation.

Figure 20:
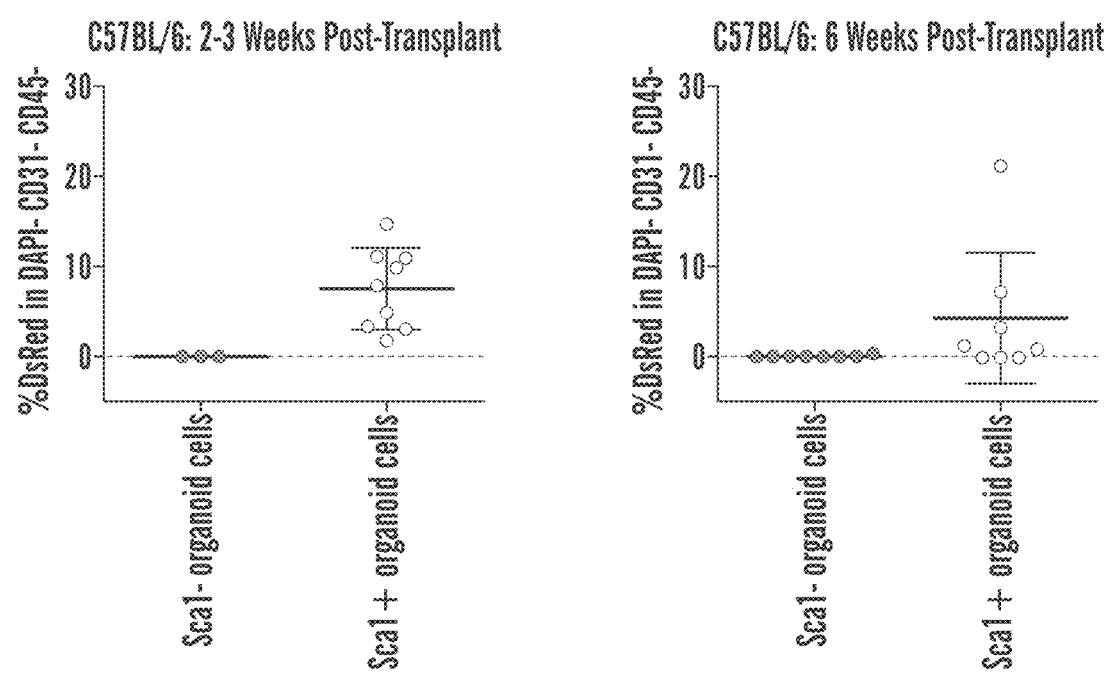

FIG. 20 shows data indicating that Sca1+ organoid cells have higher engraftment rates compared to Sca1− organoid cells in C57BL/6 mice.

Figure 21:
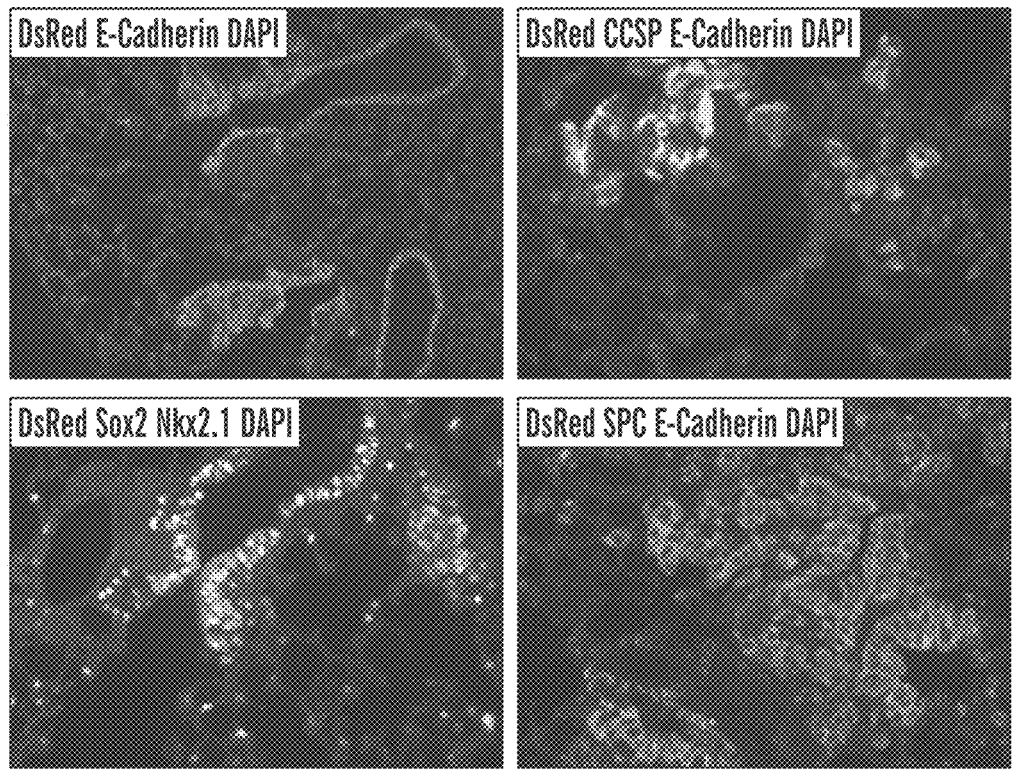

FIG. 21 shows representative images of the indicated engrafted cells.

Figure 22A:
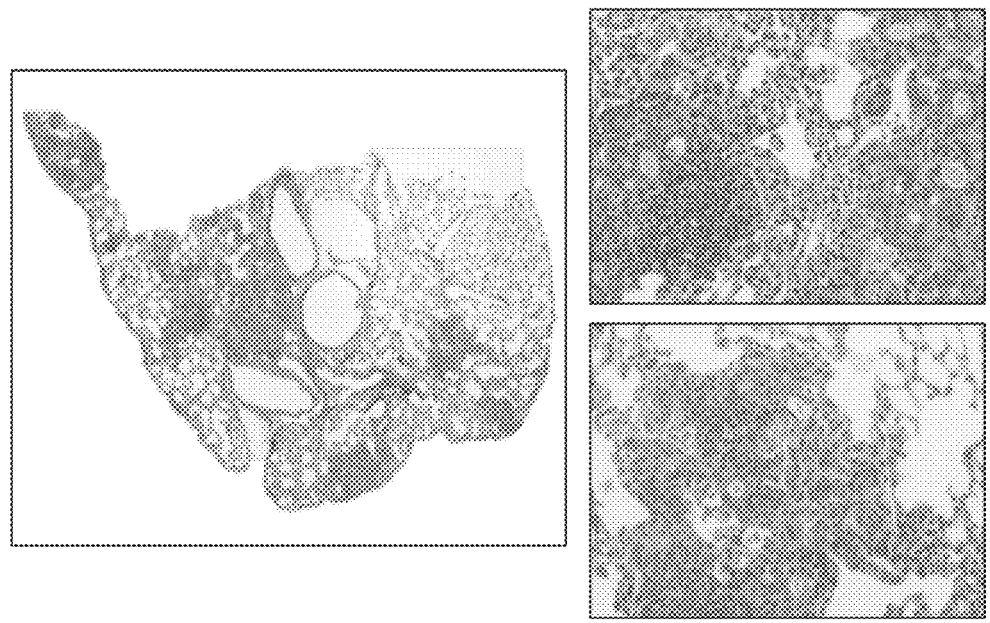
Figure 22B:
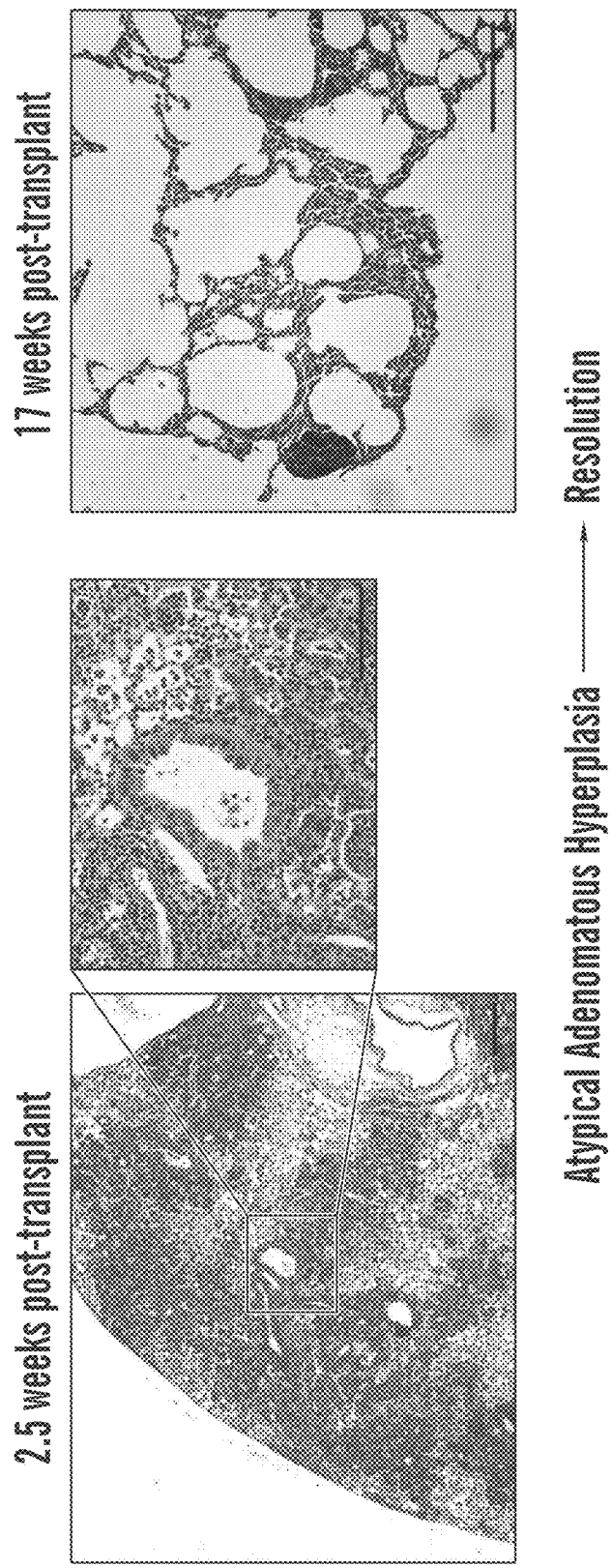
Figure 22C:
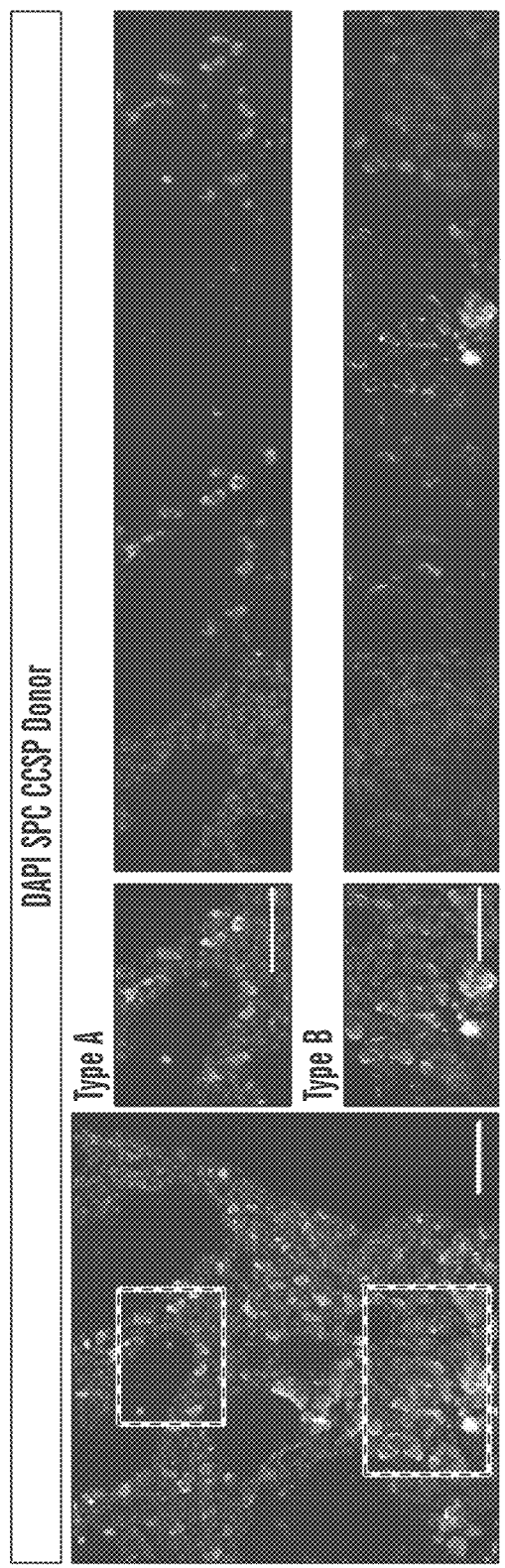

FIGS. 22A-22C. FIG. 22A shows data indicating that wildtype Sca1+ organoid cell transplants form atypical adenomatous hyperplasia. FIG. 22B shows that alveolar space engraftment and atypical adenomatous hyperplasia resolves with time. When Sca1+ derived organic cells engraft into the alveolar space, they express airway markers. H&E staining of the transplanted lungs shows large patches of atypical adenomatous hyperplasia at early time points after transplant. However, at 17 weeks post-transplant, these hyperplastic patches have mostly resolved. FIG. 22C shows a representative image of a Sca1+ recipient 17 weeks post-transplant with data indicating that airway markers are lost during resolution of adenomatous hyperplasia and alveolar markers become apparent. At 17 weeks post-transplant, two types of cells are detected in the alveolar space. Type A cells express alveolar markers but do not express airway markers. Type B cells either do not express alveolar markers or express them at low levels, while still expressing airway markers. This data is interpreted as follows: Type A cells have fully resolved the hyperplasia, while Type B cells are in the process of resolving.

FIG. 23 shows data indicating that subcutaneous delivery of Sca1+ organoids grow as well-differentiated structure in vivo and further re-culturing of wildtype Sca1+ organoid cells forms non-tumorigenic structures.

Figure 24:
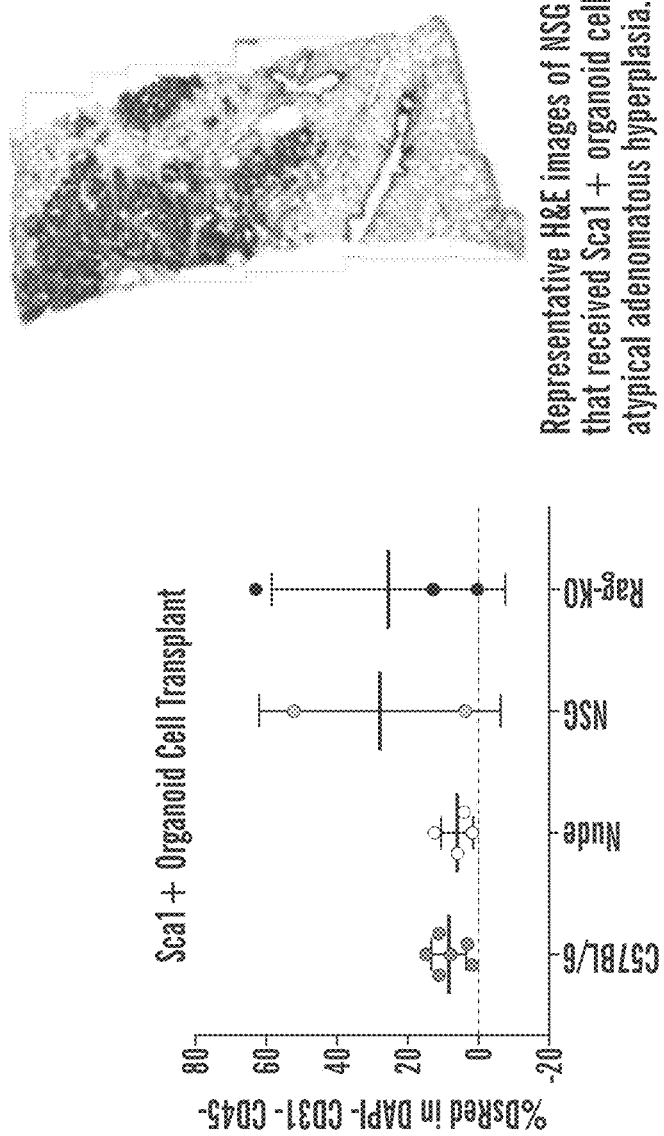

FIG. 24 shows data indicating that Sca1+ organoid cells form atypical adenomatous hyperplasia in immune deficient mice.

Figure 25A:
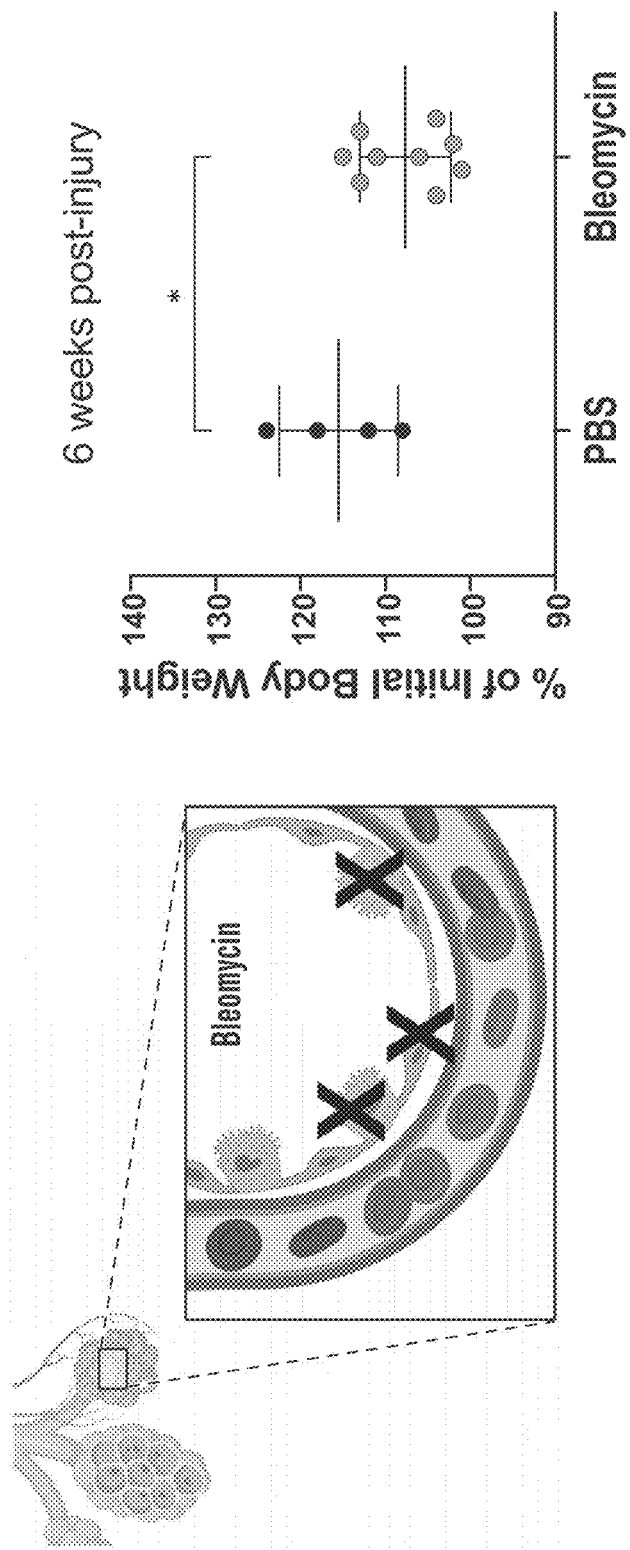
Figure 25B:
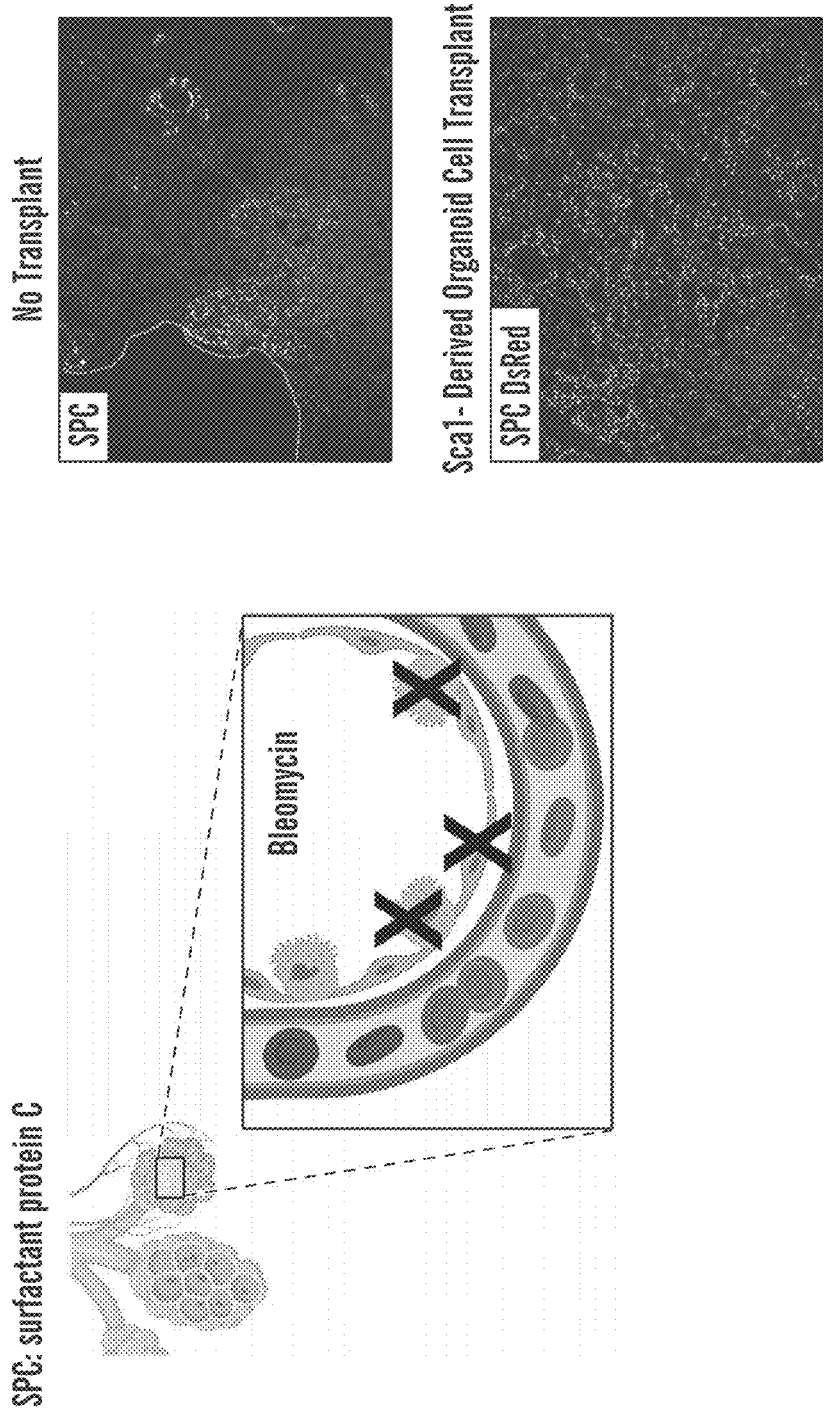

FIGS. 25A-25B. Bleomycin Injury model of alveolar injury. FIG. 25A Bleomycin is used to pre-condition and induce an injury in the recipient mice before transplantation. Bleomycin is used as a model of art-recognized alveolar injury, however club cell injury was also detected in this study. The graph shows that bleomycin intratracheal delivery results in an injury to recipient mice, based on the initial body weight of the animals. Animals that received bleomycin have reduced body weight. FIG. 25B shows data indicating that Sca1− derived organoid cells replace AT2 cells in injured lungs of Rag KO mice. In both images, mice have received bleomycin injury. In the top panel (mock transplant), there are large areas devoid of SPC+ cells, which is consistent with bleomycin injury that damages and kills alveolar cells. In the bottom panel (transplantation of Sca1− derived organoid cells), there is no evidence of the large areas devoid of SPC+ cells as in the mock-transplanted mice. A large number of SPC+ cells also co-express DsRed, suggesting that donor cells "fill in" areas of damaged alveolar cells.

Figure 26A:
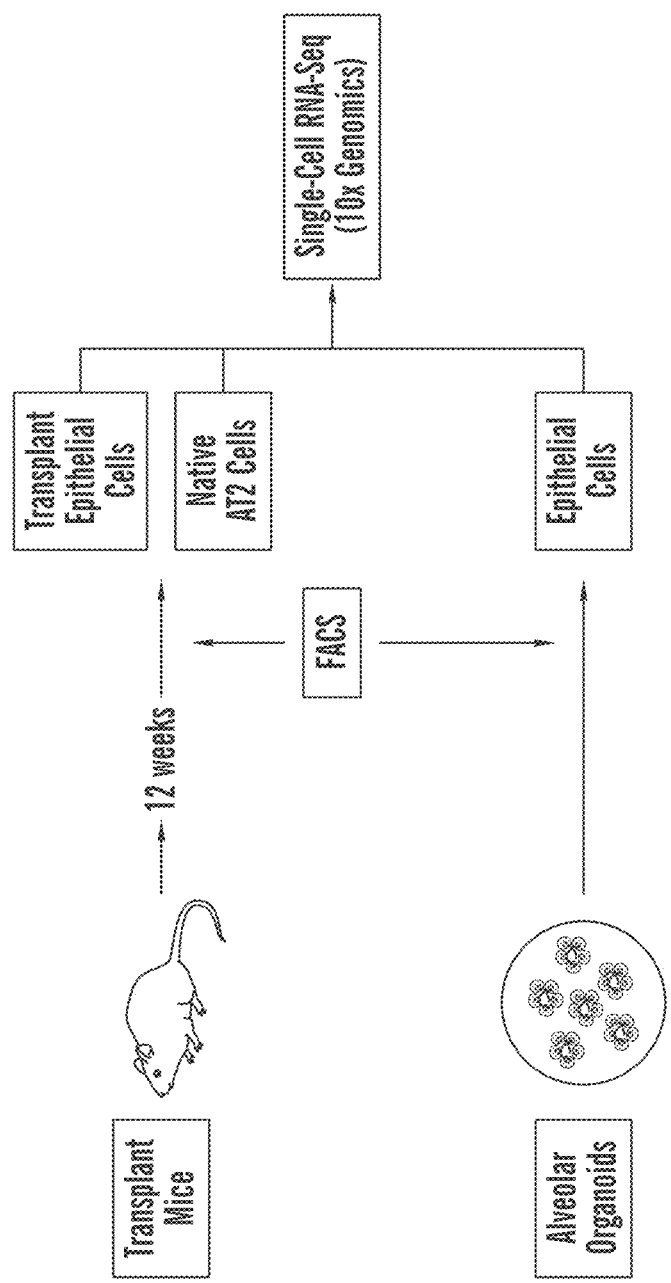
Figure 26B:
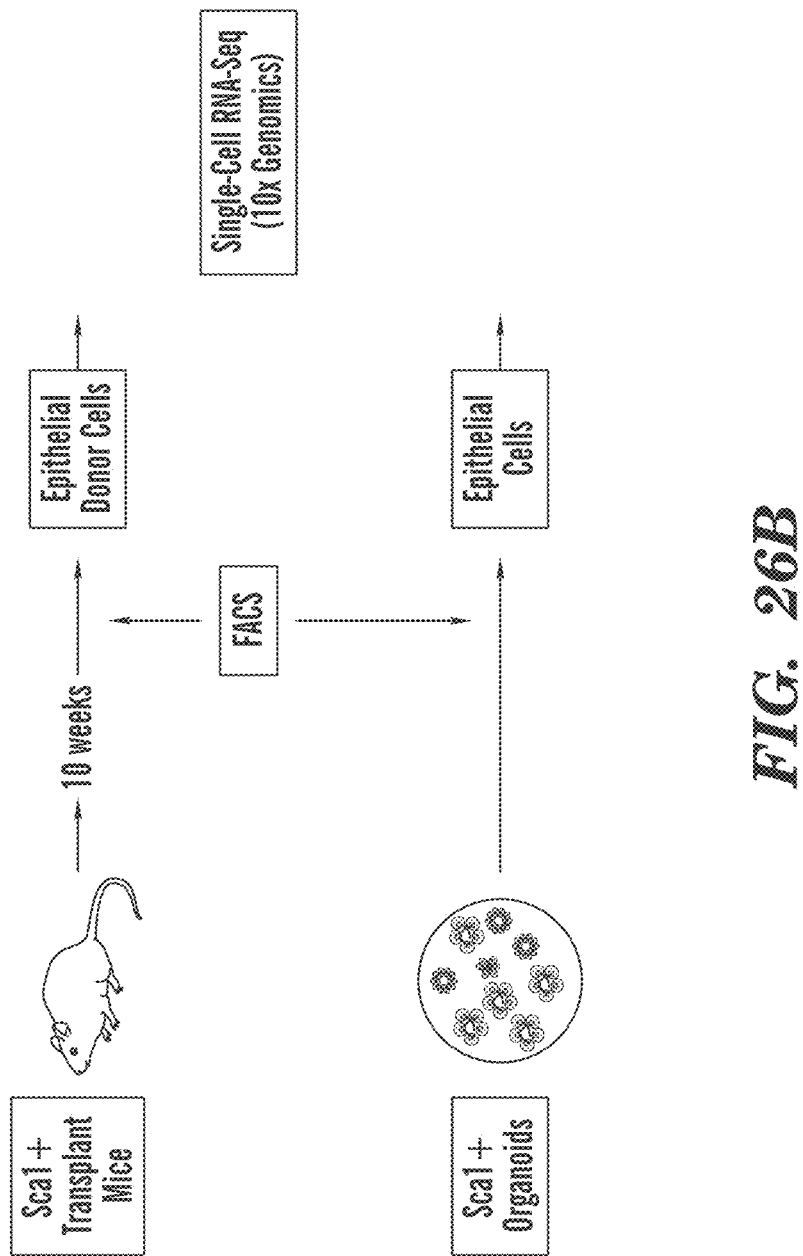

FIGS. 26A-26B. FIG. 26A shows an exemplary experimental design used to compare Sca1− transplanted, native and organoid cells using single-cell RNA-sequencing. Single-cell RNA-sequencing is used to identify cell populations transcriptionally in all Sca1− conditions. Sequencing was performed on (i) transplanted epithelial cells from RagKO Sca1− organoid cell recipient mice, (ii) endogenous AT2 cells from RagKO Sca1− organoid cell recipient mice, and (iii) epithelial cells from alveolar organoids. FIG. 26B is a schematic depicting methods for single-cell RNA-sequencing of Sca1+ transplant mouse cells and organoid cells. Single-cell RNA sequencing was used to identify cell populations transcriptionally in all Sca1+ conditions. Sequencing was performed on (i) transplant epithelial cells from RagKO Sca1+ organoid cell recipient mice, and (ii) epithelial cells from Sca1+ organoids. Note that there are no endogenous Sca1+ cells in this experiment (in contrast to FIG. 26A).

FIGS. 27A-27C Single-cell RNA sequencing of Sca1− transplant, native and organoid cells showing data indicating that organoid cells are transcriptionally distinct from mouse lung cells and transplant cells are transcriptionally similar to native cell counterparts. FIG. 27A UMAP shows all cells sequenced in Sca1− conditions. Cells are shaded according to their grouped annotation. FIG. 27B UMAP shows the same cells as FIG. 27A, but cells are now shaded by Leiden clusters, where transcriptionally similar cells are shown in the same shade. FIG. 27C shows cell type contributions to each Leiden cluster. The data provided in FIGS. 27A-27C indicate that organoid cells are transcriptionally distinct from mouse cells and that the transplant cells are transcriptionally similar to their endogenous cell counterparts. It is interesting to note that although organoid cells are distinct, upon delivery back into the mouse, they become transcriptionally similar to endogenous cells, indicating that they have similar function to endogenous cells.

Figure 28A:
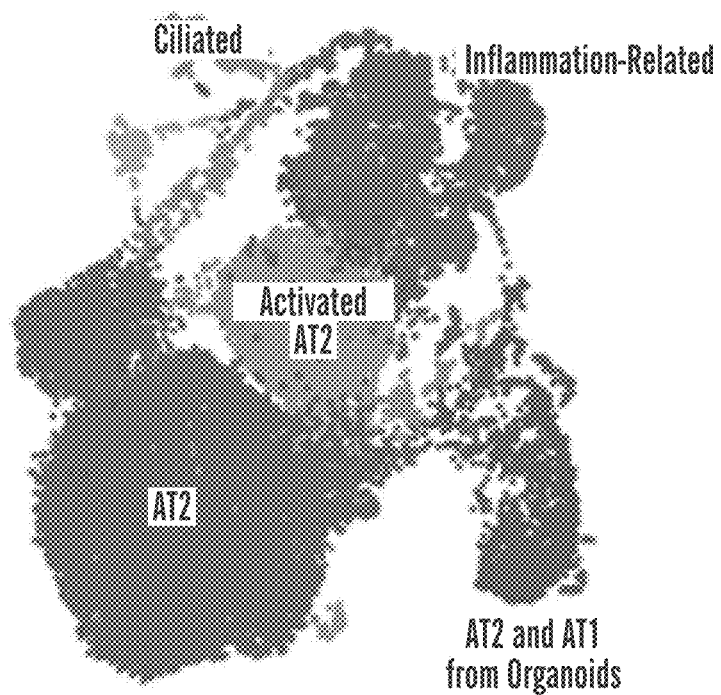
Figure 28A:
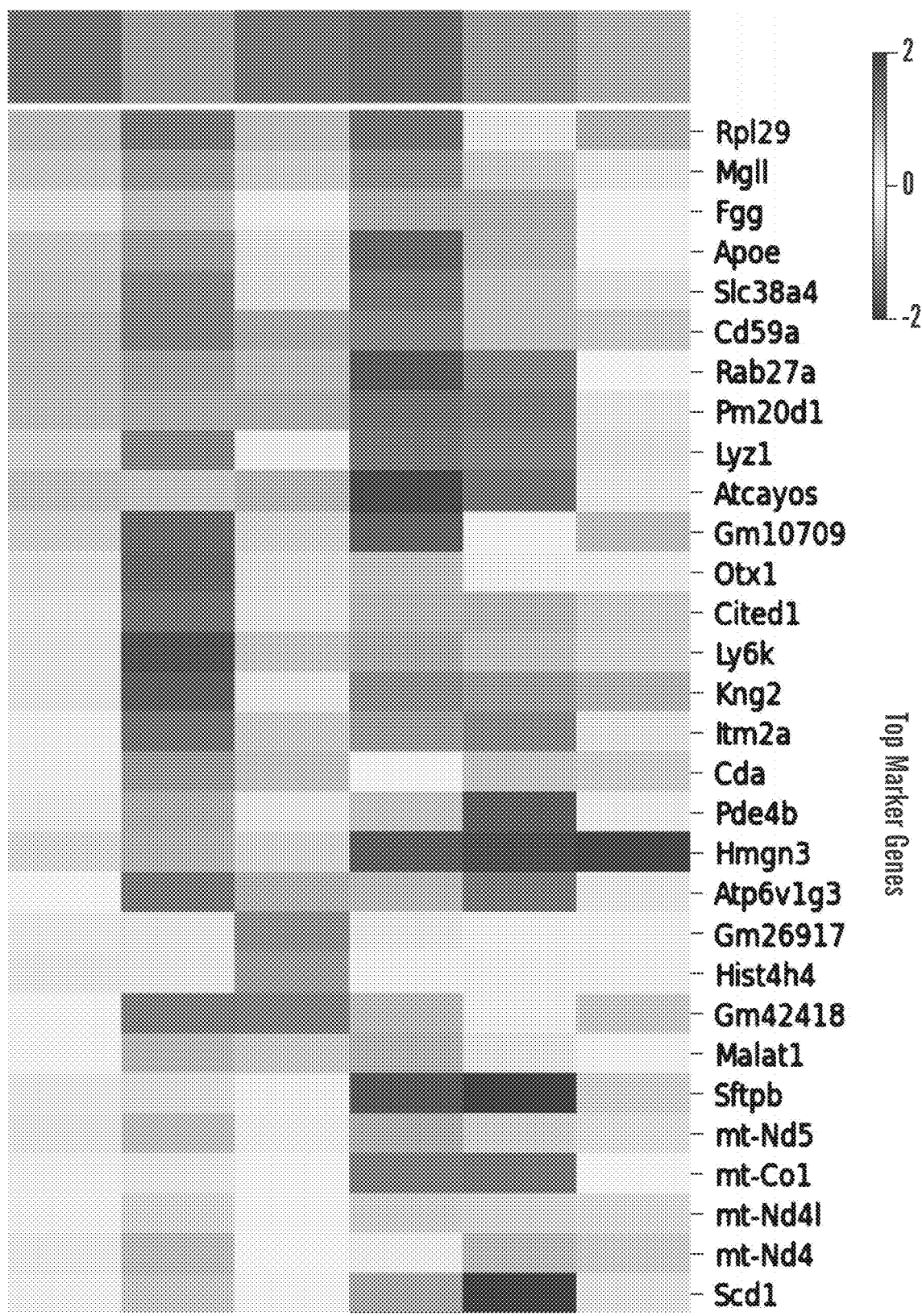
Figure 28A:
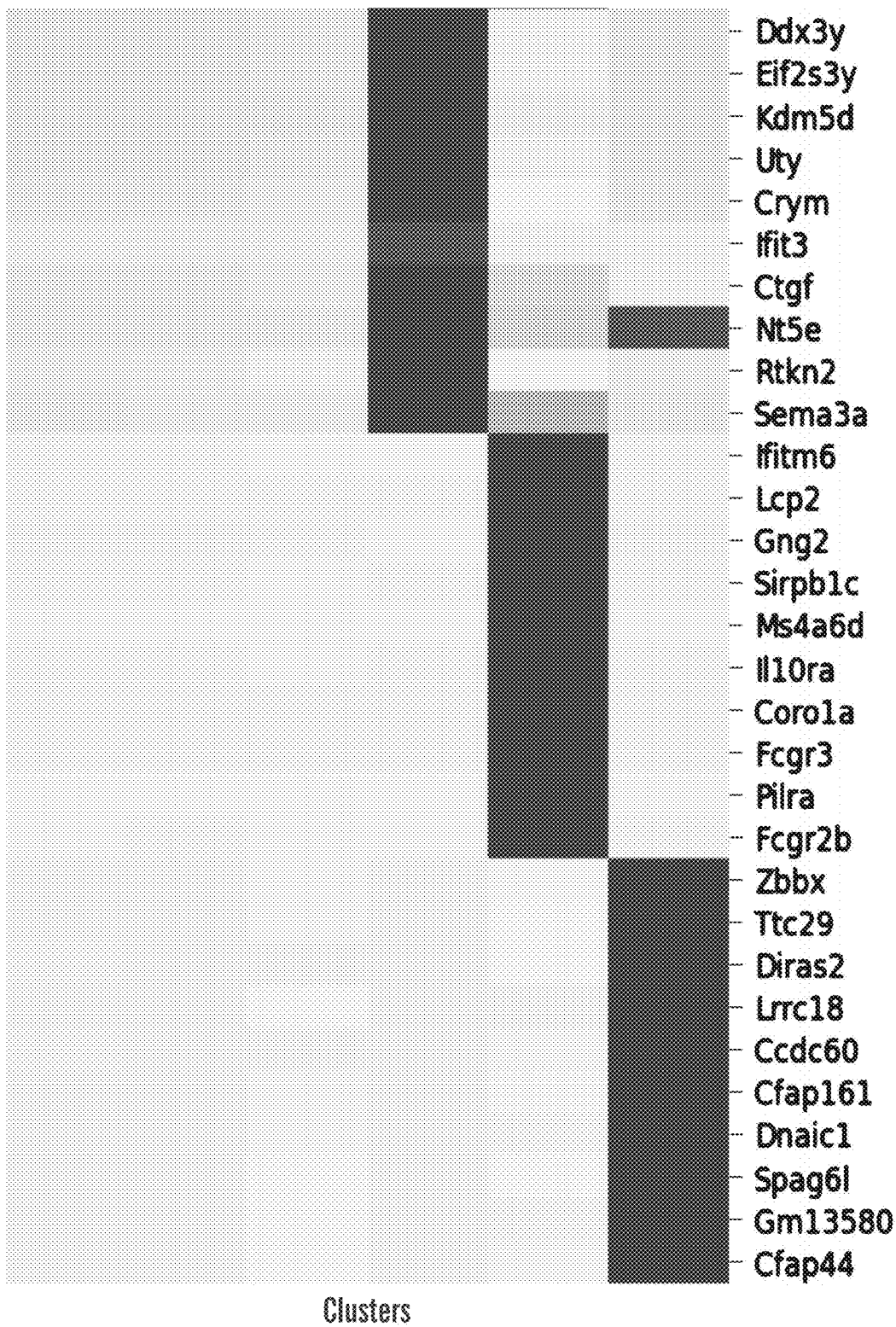
Figure 28B:
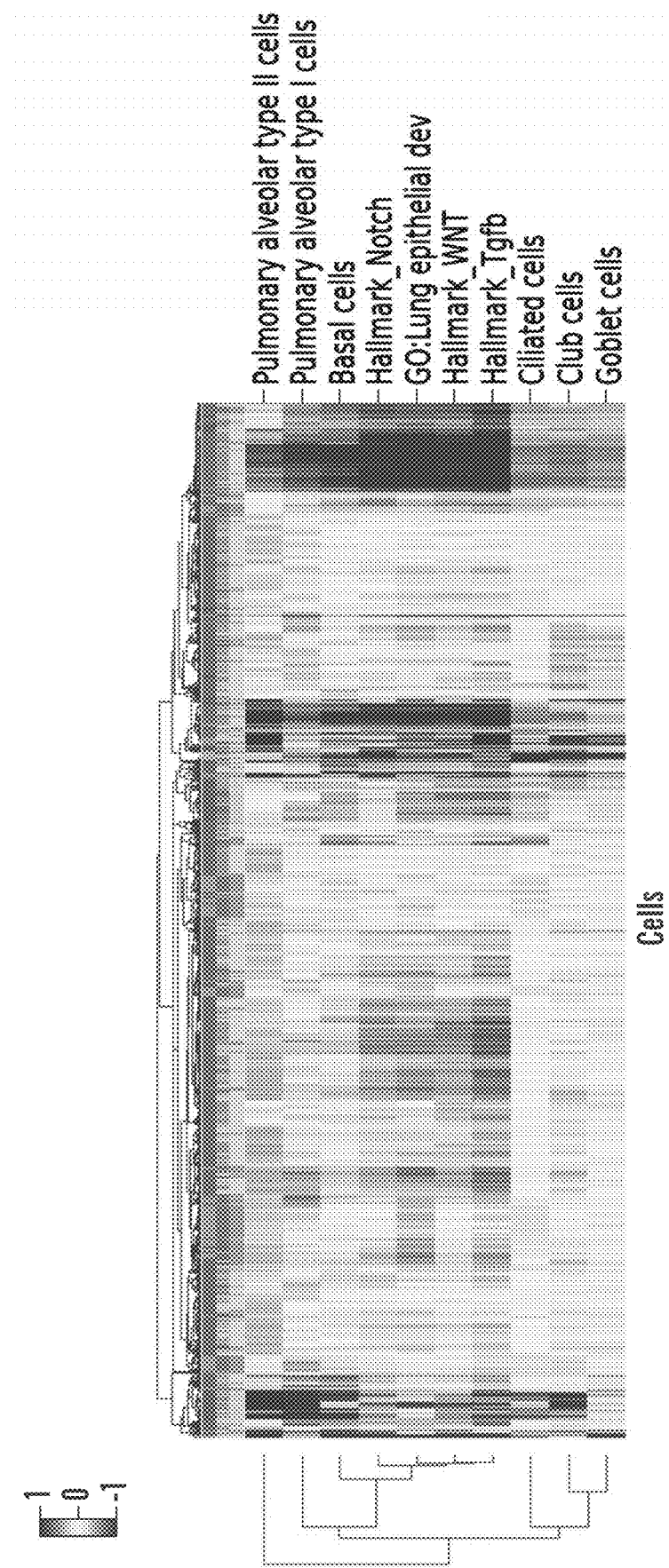
Figure 28C:
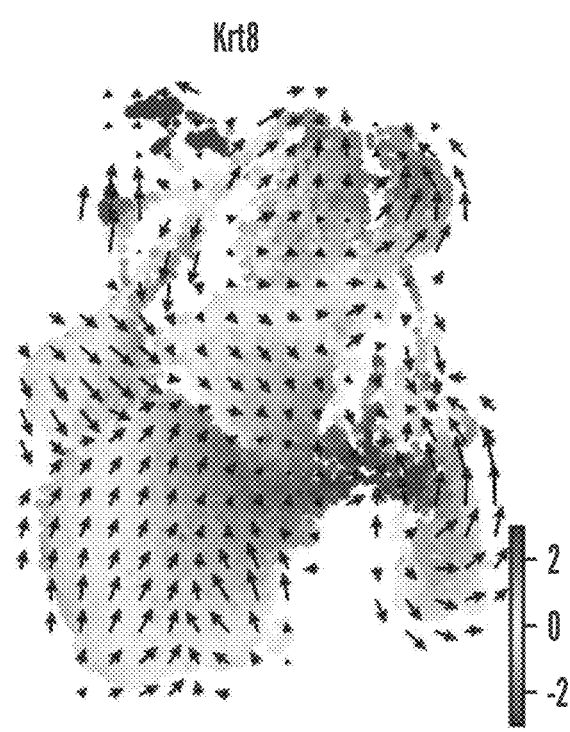

FIGS. 28A-28C show data relating to cell clusters annotated by top marker genes and cell type signatures. FIG. 28A (left) UMAP colored by Leiden clusters. Cell clusters are manually annotated using well-defined cell-type signatures; (right) top marker genes for each cluster used to identify cell types. FIG. 28B Cluster map of hierarchical clustering of all Sca1− samples. All endogenous and transplant cells cluster closely to one another by hierarchical clustering, indicating that they are transcriptionally similar. FIG. 28C UMAP of data showing expression of Keratin-8. Keratin-8 has been shown to be associated with bleomycin injury and may represent alveolar progenitor cells that are responsible for lung regeneration following injury. Arrows on UMAP represent RNA velocity analysis, which is used to predict the future state of cells. These data indicate that transplant and endogenous cells will become Keratin-8+ cells. Taken together, these data indicate that both transplant and endogenous cells include Keratin-8+ cells that are responsible for lung regeneration following bleomycin injury.

Figure 29A:
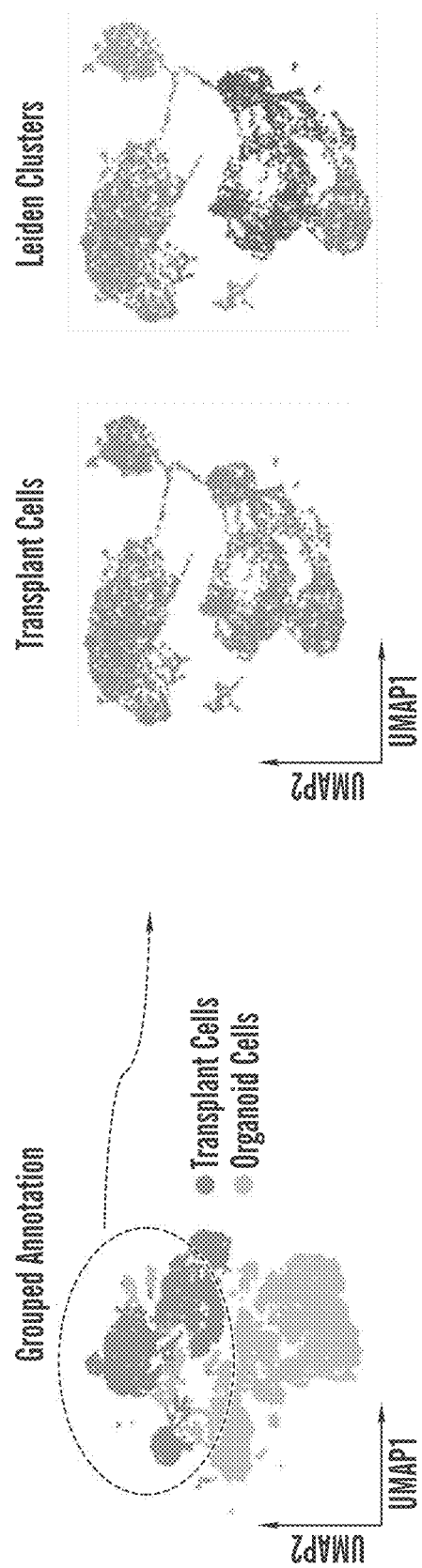
Figure 29B:
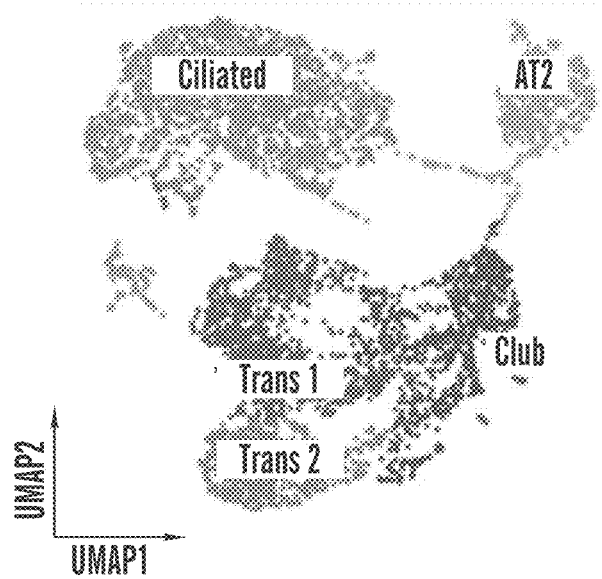
Figure 29B:
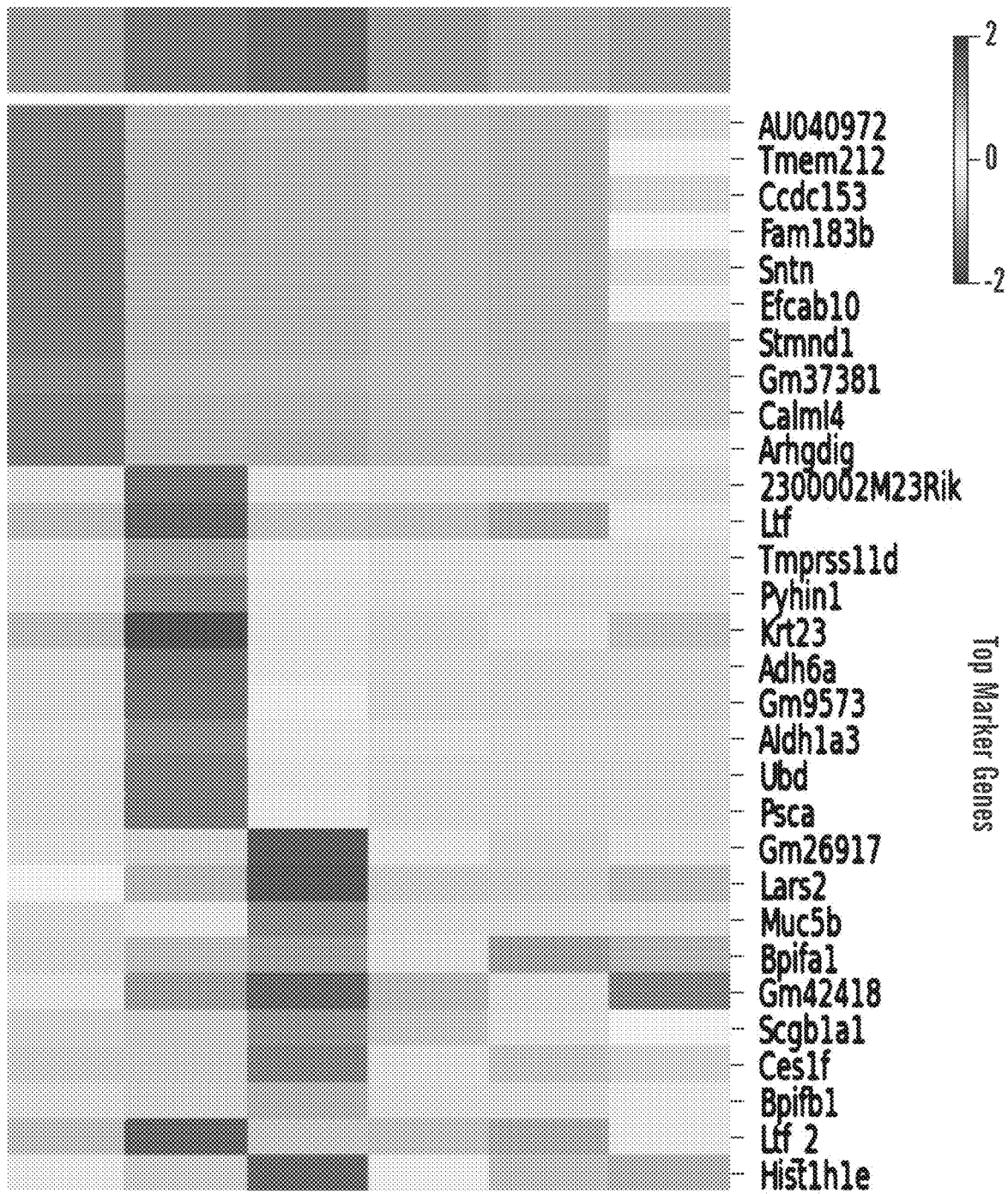
Figure 29B:
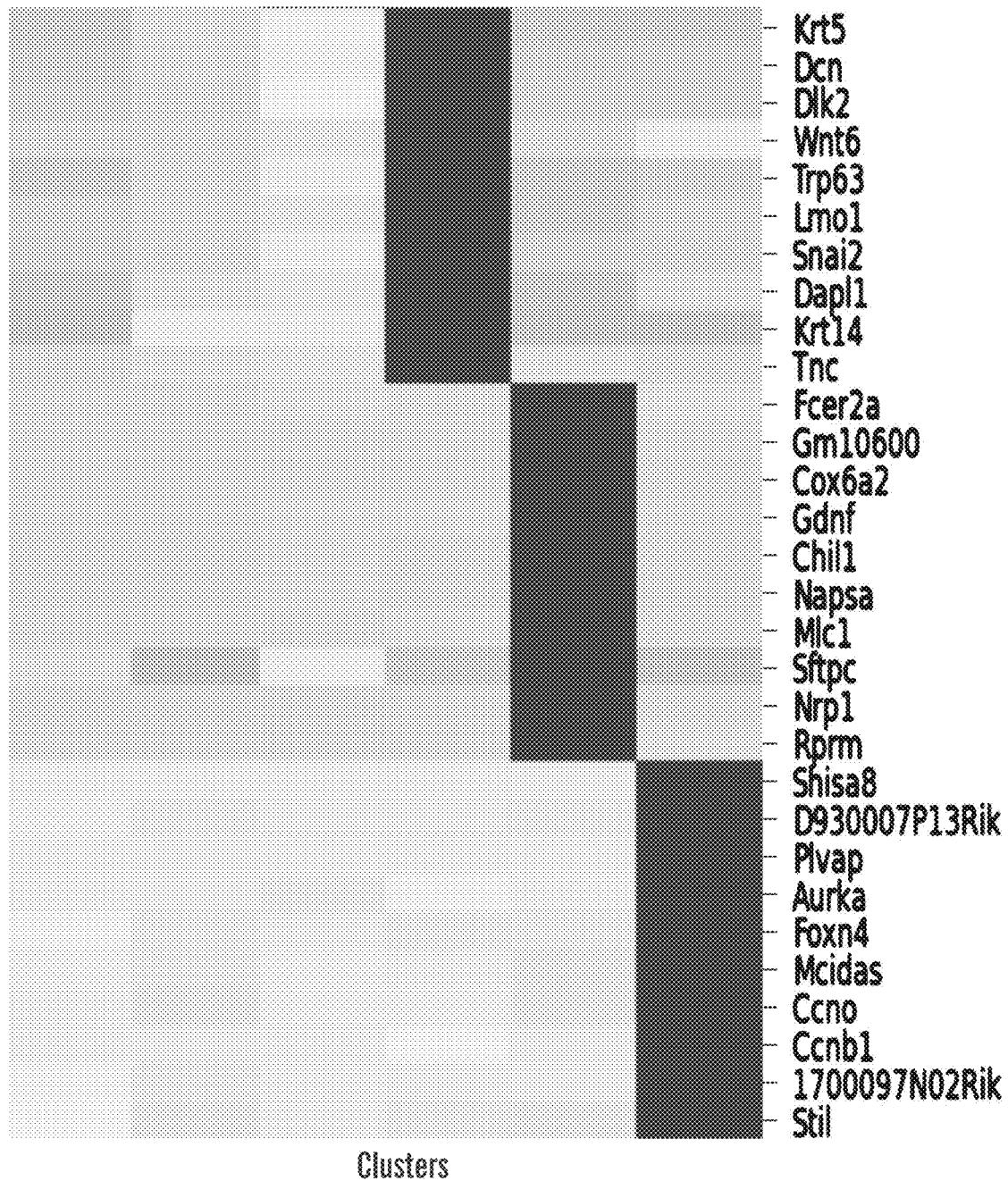
Figure 29C:
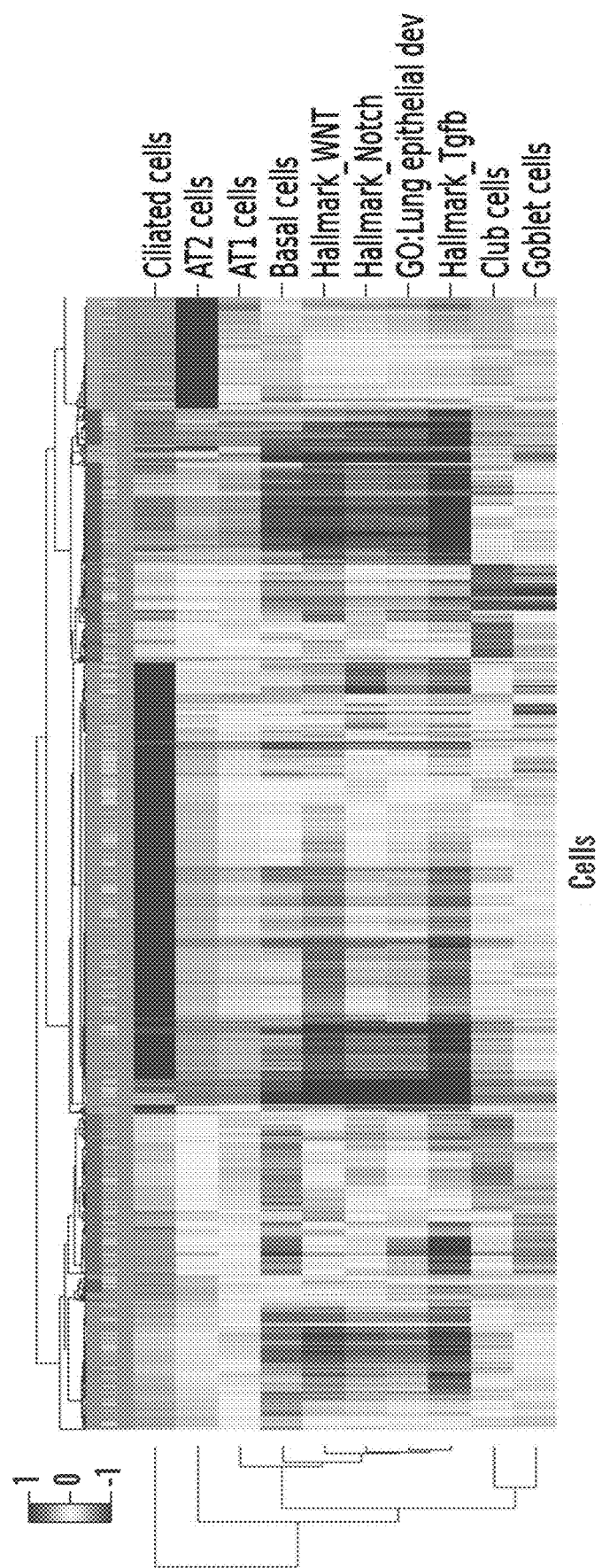
Figure 29D:
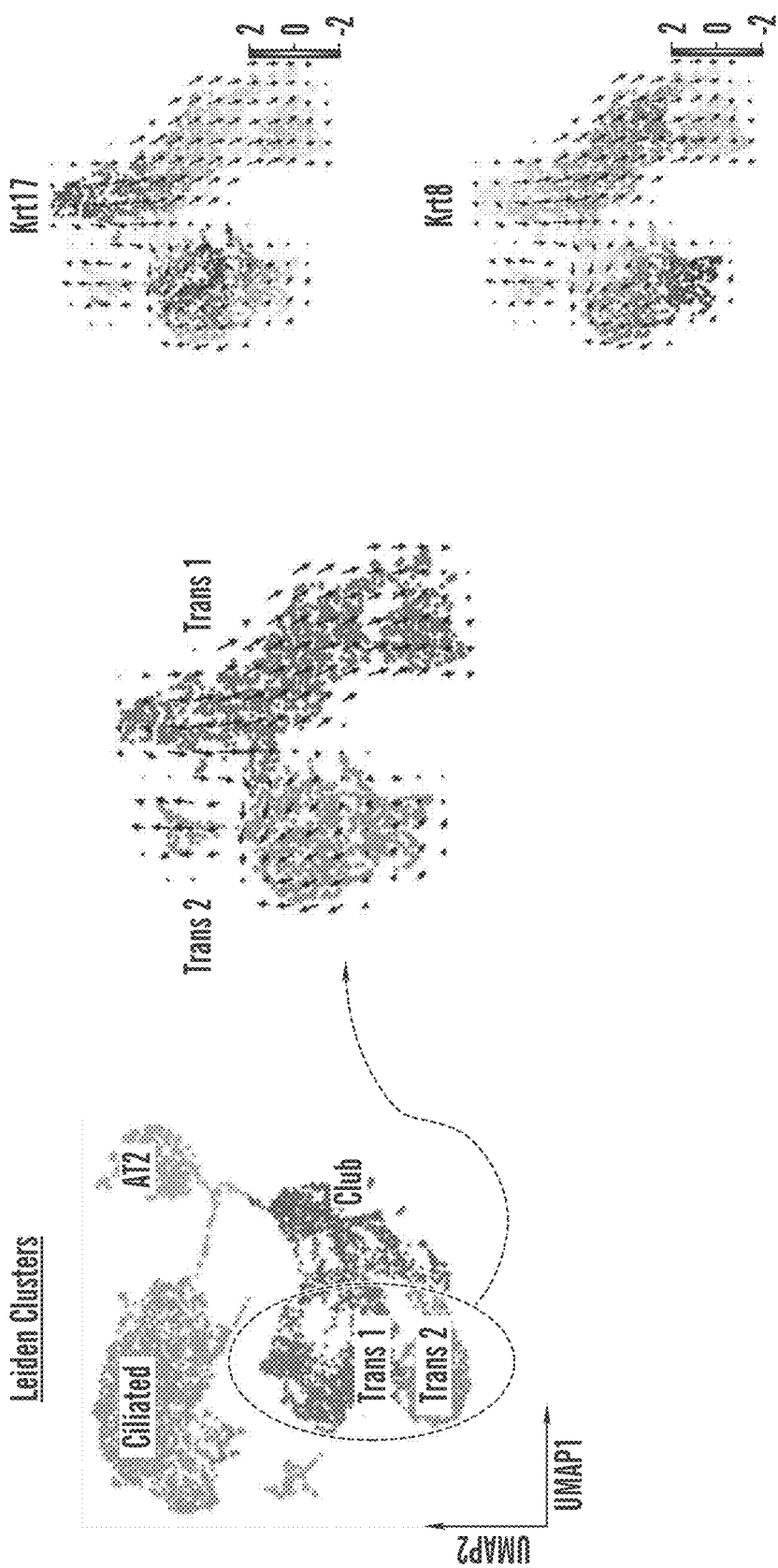
Figure 29E:
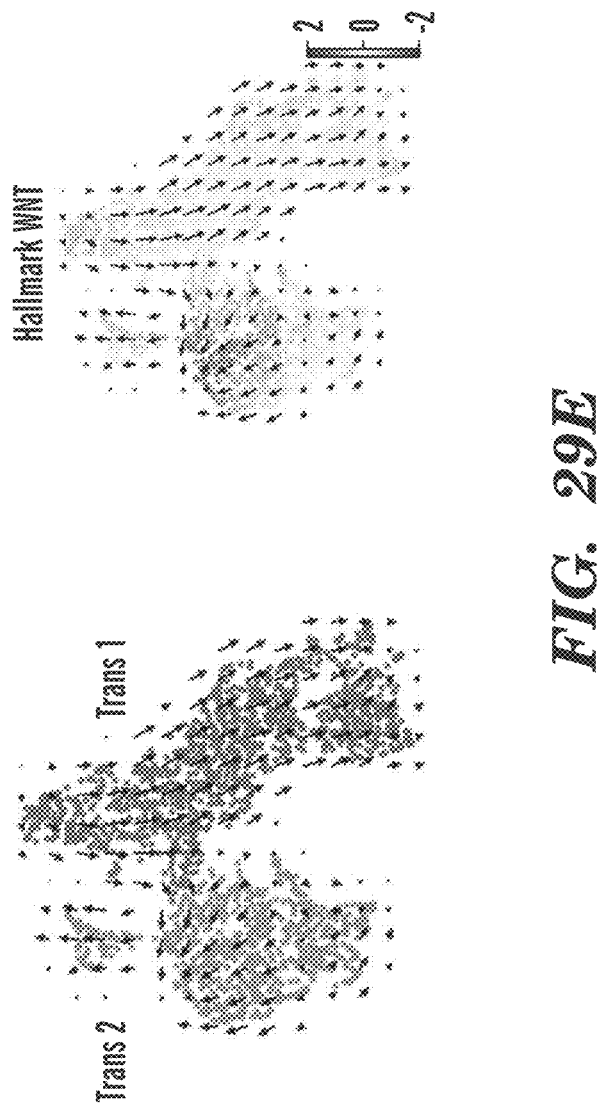
Figure 29E:
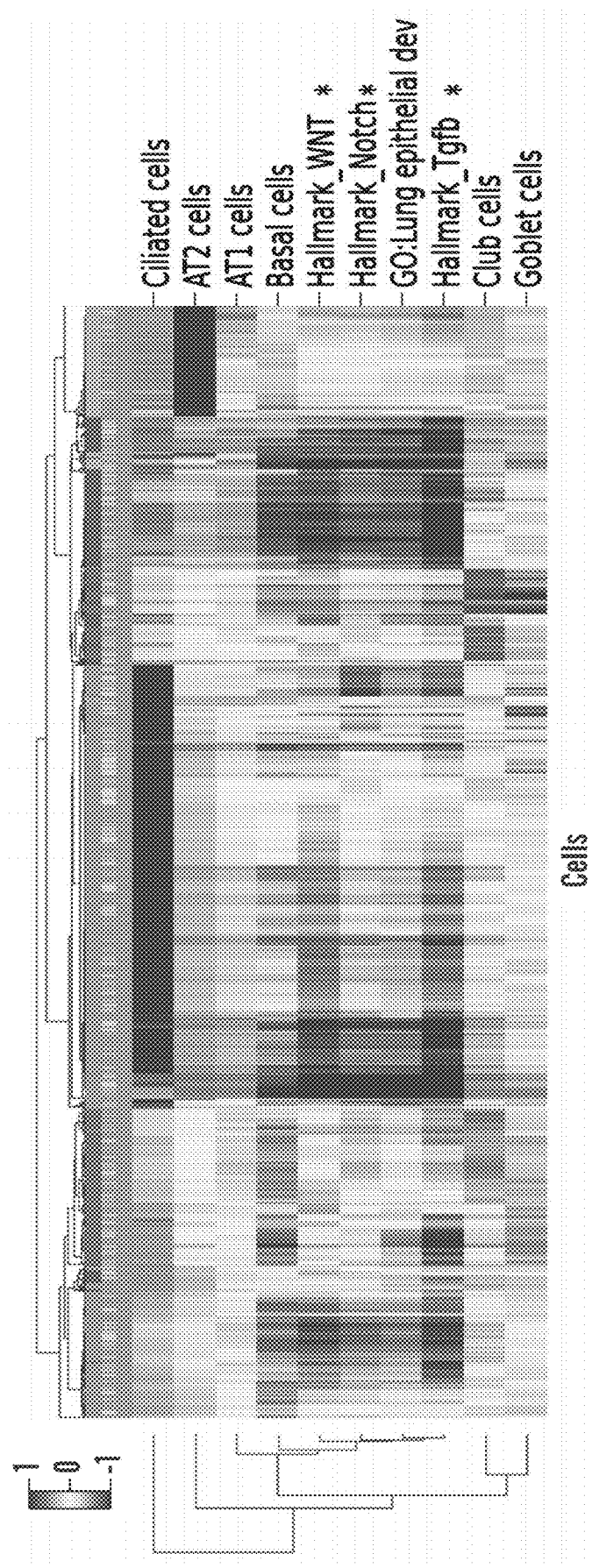

FIGS. 29A-29E. FIG. 29A (left) UMAP of all Sca1+ cells including transplant cells and organoid cells. Cells are shaded by grouped annotations; (middle) UMAP of transplant cells only; (right) UMAP is shaded by Leiden clusters, where transcriptionally similar cells are shaded the same. Taken together, these data indicate that organoid cells are distinct from transplant cells. FIG. 29B (left) UMAP of all Sca1+ cells including transplant cells and organoid cells. Cells are shaded by Leiden clusters and manually annotated using well-defined cell type signatures. Transitional clusters 1 and 2 are not defined by any specific lung epithelial signature, and thus they are annotated as transitional clusters; (right) top marker genes for each cluster. FIG. 29C Cluster map showing hierarchical clustering of all Sca1+ transplant cells. Well-defined lung cells epithelial cells, such as ciliated cells, AT2 cells and club cells can be identified from the cluster map. Transitional clusters 1 and 2 are most similar to one another according to hierarchical cluster map. Without wishing to be bound by theory, such transitional cells may correspond to the hyperplastic patches. FIG. 29D (left) UMAP of all Sca1+ cells including transplant cells and organoid cells (shaded by Leiden cluster and manually annotated using well-defined cell type signatures; (middle) UMAP of transitional clusters grouped by Leiden clusters; (right) UMAP of transitional clusters colored by Keratin 17 and Keratin 8 expression. Keratin 17 and Keratin 8 are good markers to distinguish transitional clusters and are known to be associated with an alveolar to basal transdifferentiation phenotype in human cells. RNA velocity (arrows on UMAP) predict that some Keratin 8+ cells may become Keratin 17+ cells. FIG. 29E Relevant pathways involved in transitional cell fate decisions. (Top left) UMAP of transitional clusters, (top right) Transitional 2 cells have higher score for Hallmark Wnt pathway; (bottom) transcriptional clusters have higher scores for pathways such as Hallmark Wnt, Hallmark Notch, and Hallmark Tgfb, which may be involved in transitional cell fate decisions.

Figure 30:
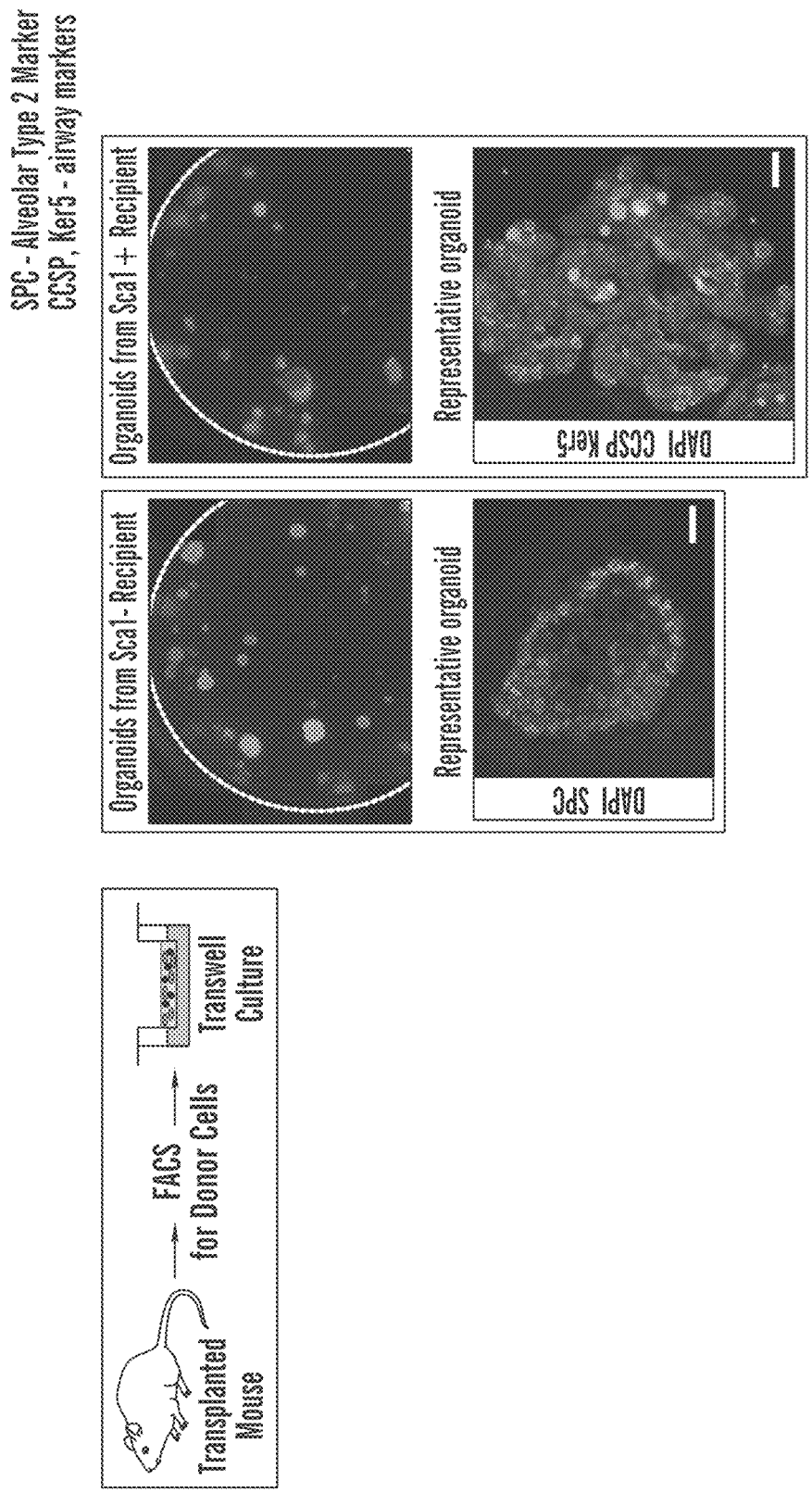

FIG. 30 Transplanted cells can be cultured and give rise to organoids. Transplanted cells are functional and retain progenitor cells function. Transplanted cells are re-isolated from mice using FACS and when placed back into culture, they form organoids. Transplanted cells from Sca1– recipients give rise to alveolar organoids, while transplanted cells from Sca1+ recipients give rise to alveolar and bronchiolar organoids. These data indicate that the transplanted cells are functional and retain their progenitor cell function as evidenced by their ability to give rise to organoids.

FIG. 31 Transplanted cells can respond to subsequent injury. Transplanted mice are given a second bleomycin injury to assess whether transplanted cells can respond to injury. BrdU is incorporated into proliferating cells and the lung response to injury by proliferating. The % BrdU+ cells were assessed in both transplant epithelial cells and endogenous epithelial cells. There was no significant difference observed in the percent of transplanted cells that incorporate BrdU between Sca1– and Sca1+ recipients. There was also no significant difference observed with respect to percent of endogenous epithelial cells that incorporate BrdU between no transplant, Sca1– recipients and Sca1+ recipients that all received a subsequent bleomycin injury. Nonetheless, transplanted cells are functional and can respond to a subsequent injury by proliferating.

Figure 32:
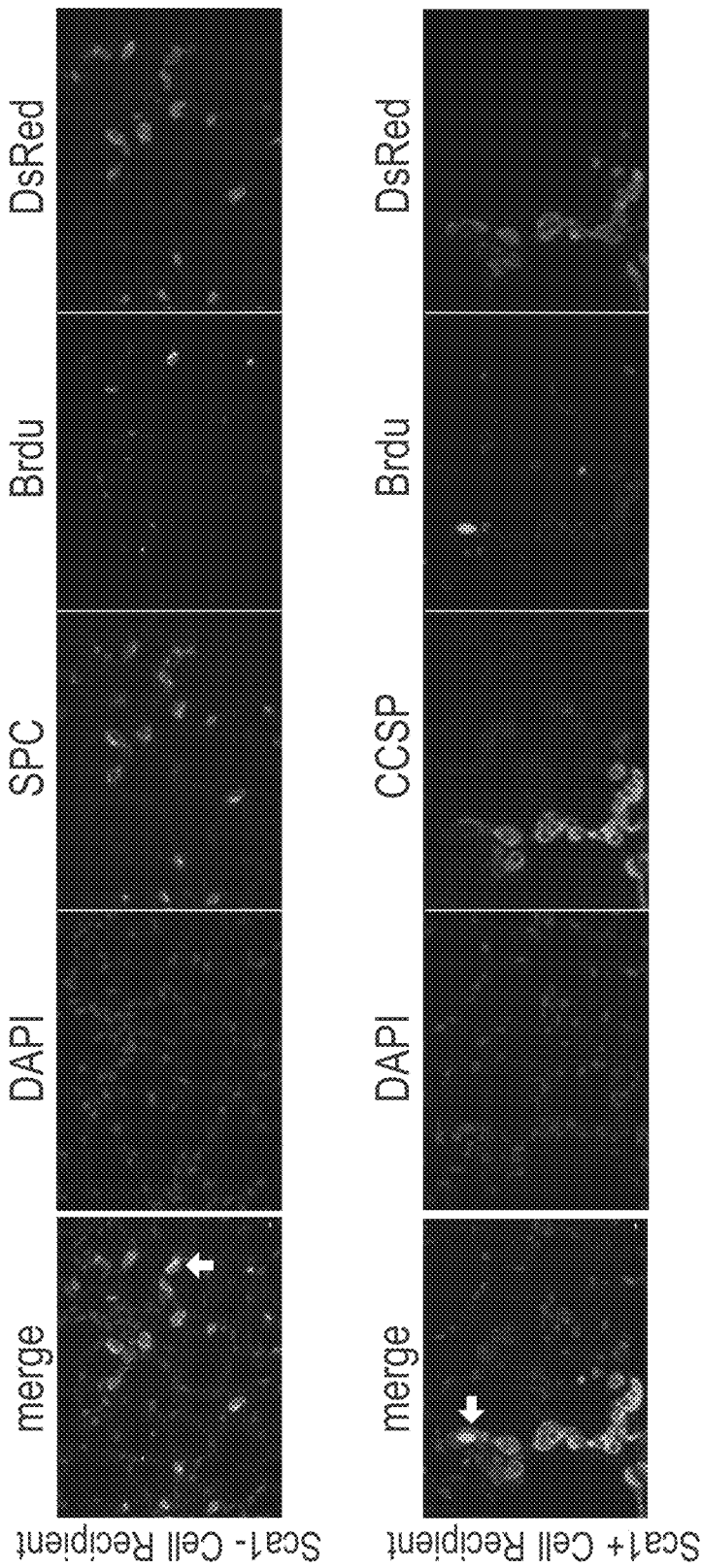

FIG. 32 shows representative IF images of transplant mice that received a subsequent bleomycin injury. These images show that some lung epithelial cells co-stain for BrdU and are proliferative. That is, transplanted cells are functional and respond to a second injury by proliferating. Donor cells are DsRed+. SPC is an alveolar type 2 cell marker. CCSP is an airway cell marker.

Figure 33:
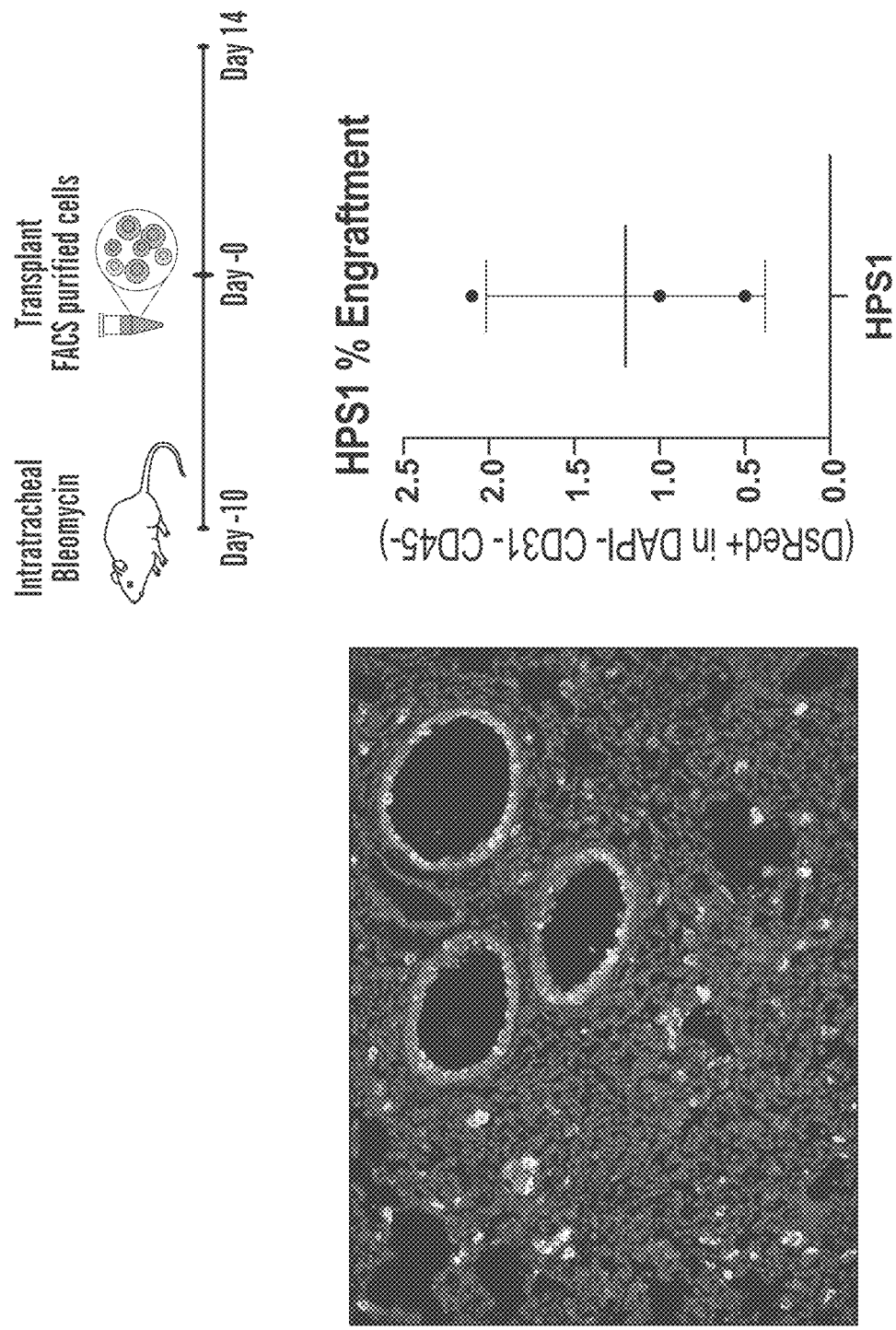

FIG. 33 Additional mouse models of disease. One potential caveat of the bleomycin injury model as an IPF model is that the fibrosis can self-resolve and the lung repairs. The Hermansky-Pudlak Syndrome (HPS1) mouse model ("pale ear model") can be a more suitable model for fibrosis, as it has been reported to have high mortality rates from bleomycin and is not able to resolve fibrosis. These data indicate that Sca1– FACS purified cells can engraft in HPS1 mice.

Figure 34:
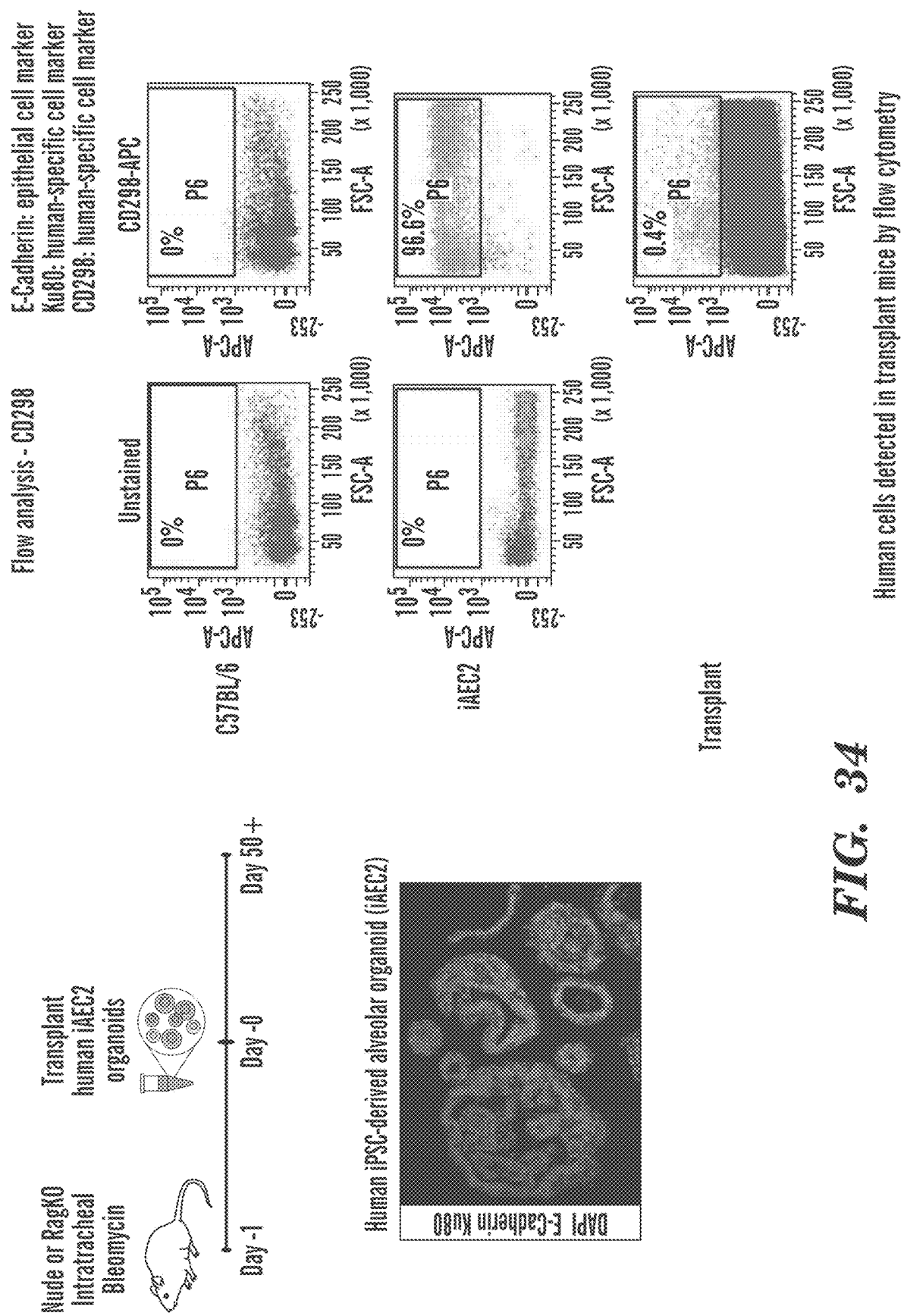

FIG. 34 human iPSC-derived alveolar organoid cells were transplanted into both nude and Rag KO immune-compromised mice. (upper left) schematic showing exemplary experimental design; (lower left) representative image of human iPSC alveolar organoids. (Ku80 is a human-specific marker); (right) Human transplant cells can be detected by flow cytometry analysis using the marker CD298.

FIG. 35 shows data indicating that human primary alveolar (hPal) organoid cells may engraft in mouse lung. Primary alveolar organoids obtained from freshly sorted cells of distal human lung were transplanted into nude mice. 14 days post-transplant, CD298+ cells were still evident in the mouse lung.

Figure 36:
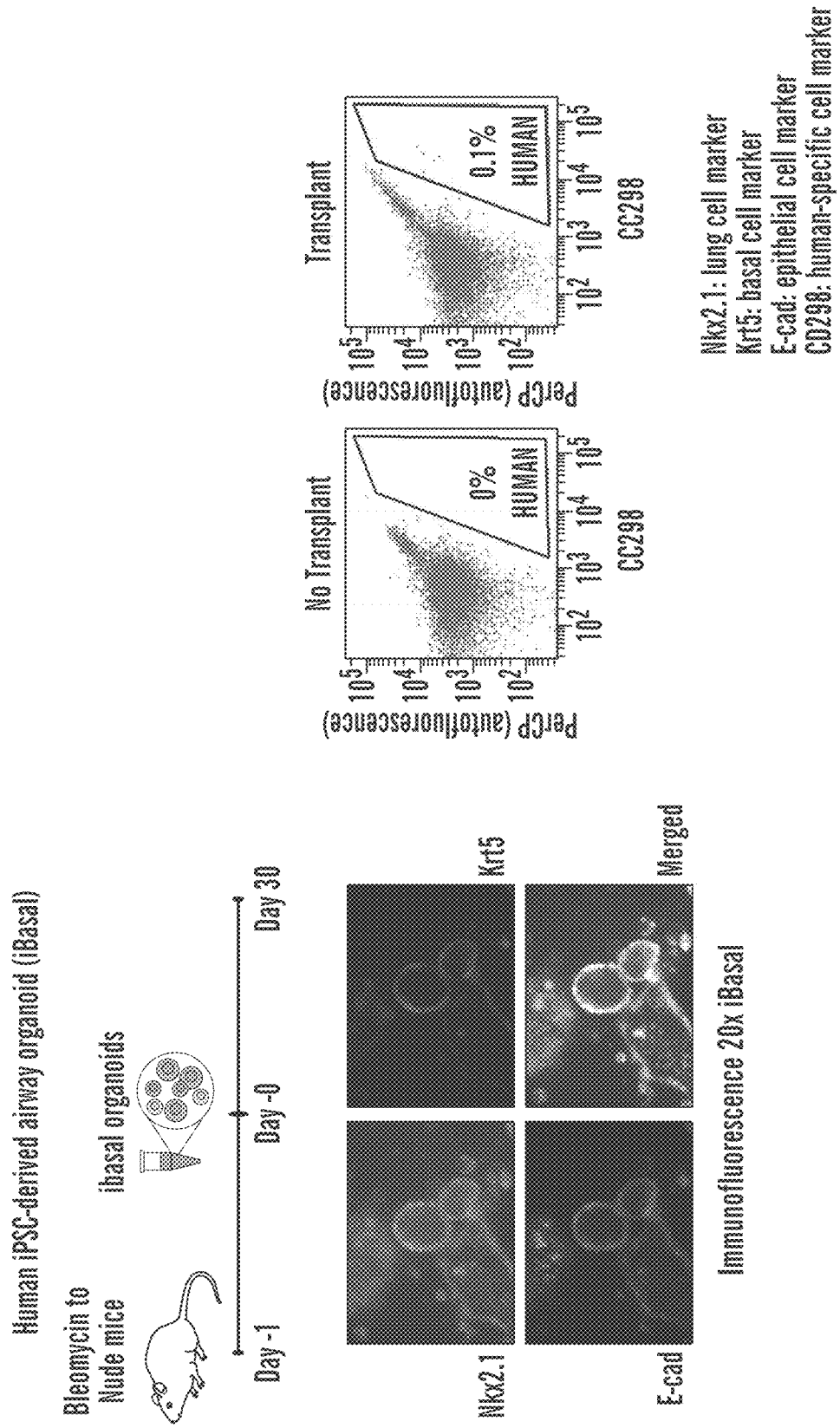

FIG. 36 shows data indicating that human iPSC-derived airway organoid cells may engraft in mouse lung. hiPSCs were cultured and differentiated towards airway (iBasal) organoids following the Kotton lab's protocol and were transplanted into nude mice. 30 days post-transplant, CD298+ cells were still detectable in the mouse lung.

Figure 37:
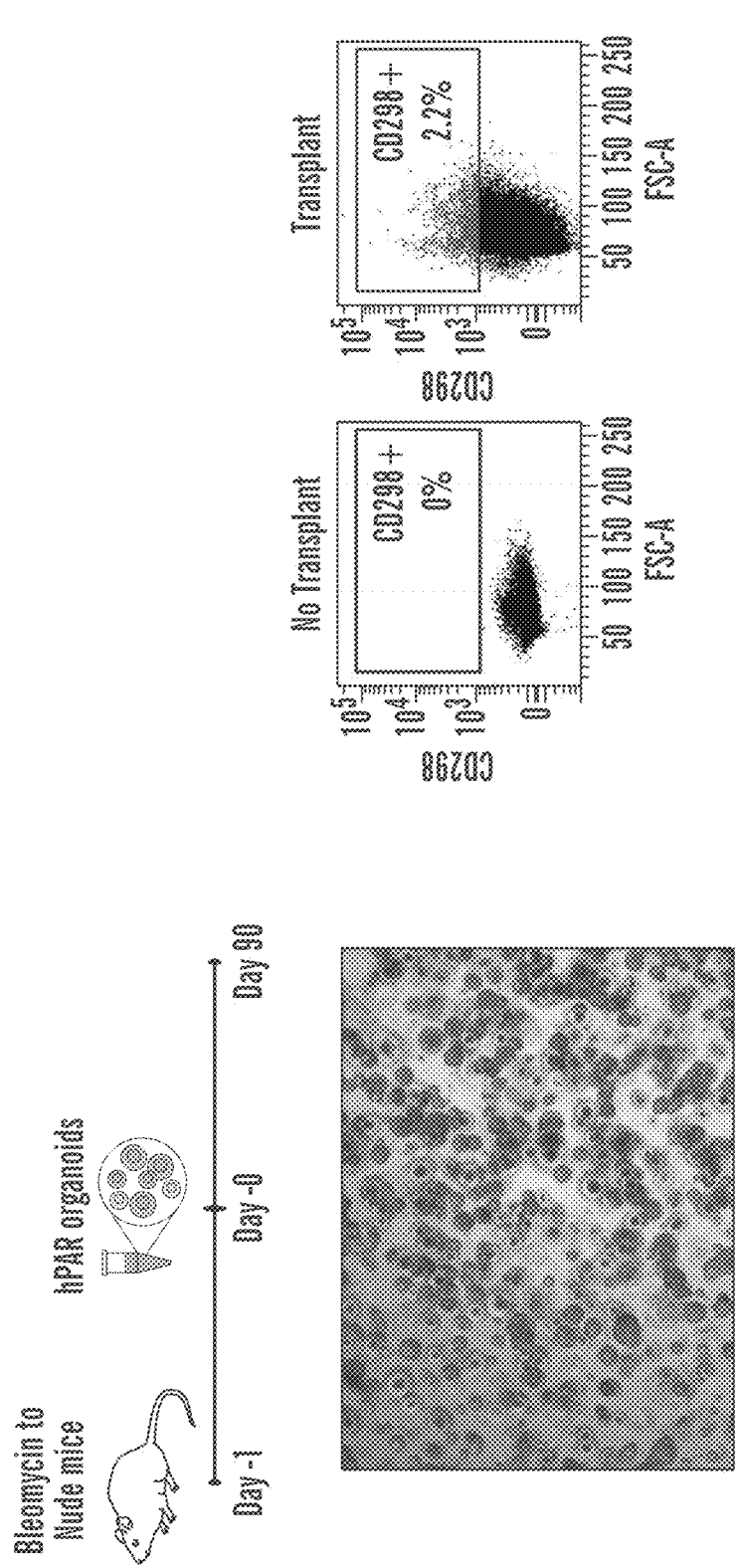

FIG. 37 shows data indicating that human primary airway (hPAR) organoid cells may engraft in mouse lung. Primary airway organoids obtained from the Clevers' lab were transplanted into nude mice. 3 months after transplanting the cells, CD298+ cells were still evident in the mouse lung.

Figure 38:
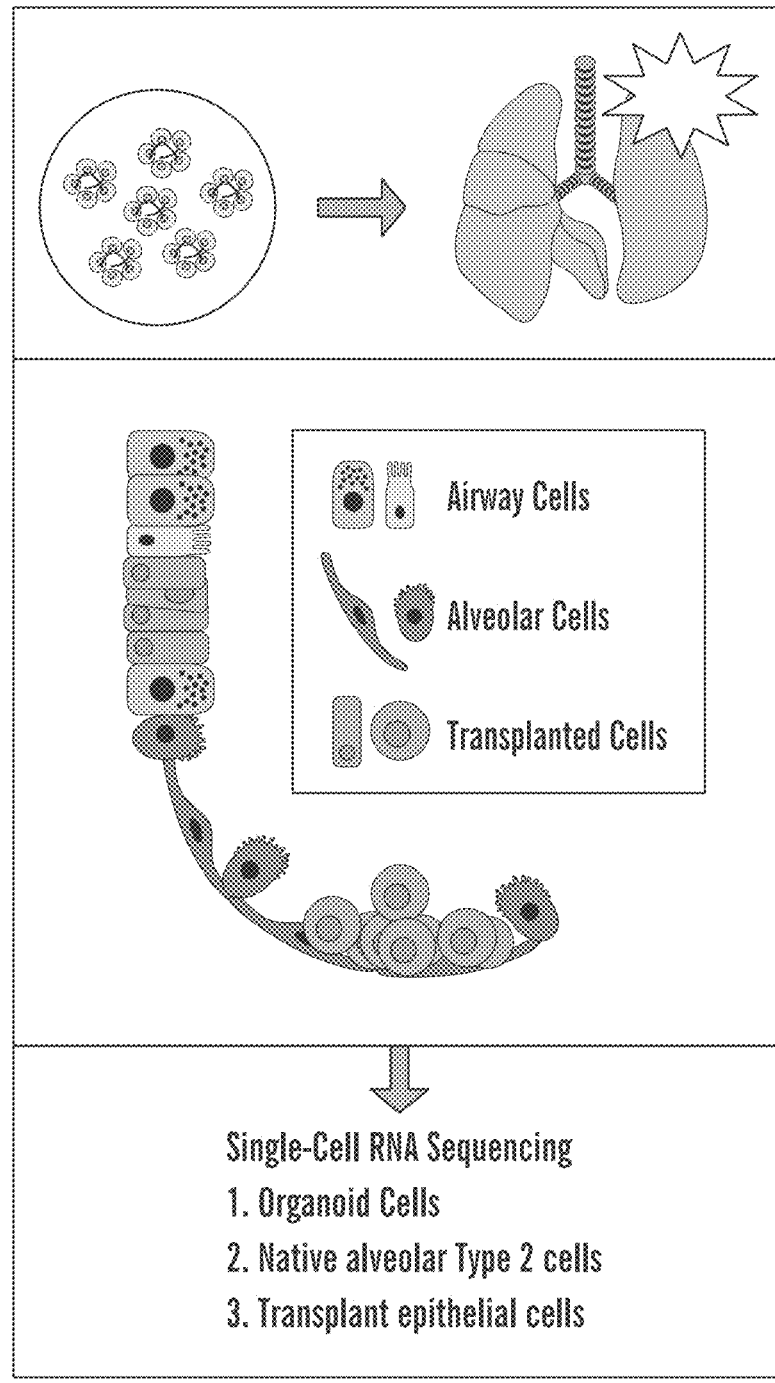

FIG. 38 shows a schematic representation of culture and transplantation of organoids into injured lung, and how their function is assessed. A summary of the findings of the studies herein are as follows: (i) Sca1– derived organoid cells engraft in alveolar space, (ii) Sca1– transplant cells are transcriptionally similar to native cell counterparts, (iii) Sca1+ derived organoid cells engraft in alveolar and airway space, (iv) Sca1+ transplant cells include well-defined lung epithelial cells and transitional cells, (v) Transplanted cells retain progenitor cell function and give rise to organoids when cultured, (vi) Transplanted cells are functional and proliferate in response to a subsequent injury, (vii) Organoid cell engraftment may be dependent on T cells, (viii) HPS1 mouse model may be an improved model to assess cell therapy potential, (ix) Human iPSC-derived alveolar, primary alveolar, iPSC-derived airway, and primary airway organoids can be transplanted and detected in recipient mice, and (x) Human cell transplant mice may be used to model COVID-19.

DETAILED DESCRIPTION

Provided herein are methods and compositions relating to the treatment of a lung disease or disorder or a lung injury using alveolar or airway organoids. Also provided herein are mouse models and screening assays using mice transplanted with alveolar or airway organoids for the development of agents useful for treating Coronavirus disease (COVID)-19. Also provided herein are methods for generating such alveolar organoids or airway organoids in vitro.

Also provided herein are functional transplantation methods for delivering lung organoid cells into injured mouse lungs intratracheally and that permit the organoids to form well-differentiated structures in vivo. Other publications have shown that various types of human and mouse lung cells engraft into an injured lung, but none of these studies have shown successful engraftment, functional aspects or characterized the cells that have engrafted. Furthermore, other studies have delivered cells that may be harder to derive (e.g. embryonic sources), whereas lung organoids described herein can be grown from adult mouse lung cells. Thus, these methods and compositions solve one of the issues associated with lung transplantation, that of availability of appropriate lung cells for transplantation.

In the studies presented herein, bronchiolar organoid cells are shown to engraft into the airways of the mice. These engrafted cells express airway markers. These results are promising for diseases such as cystic fibrosis, where patients with rare CF-related mutations, that do not respond to the CFTR modulators, may benefit from cell-based therapy. The data provided in the working Examples indicate that the transplanted cells can engraft into the airway and express acetylated alpha-tubulin, indicating the capacity of these cells to contribute to multiciliated cells and potential relevance to cystic fibrosis. Towards this end, the inventors have also transplanted basal cells from the trachea, and have shown that these engrafted cells express some airway markers.

It is also shown herein that alveolar organoid cells can engraft into the alveolar space of the injured mouse lung, and in particular more efficiently in immune deficient mouse models. It is important to note that alveolar cells are generally harder to culture and manipulate, but the inventors have been able to grow alveolar organoids that express alveolar markers, which is an improvement over prior studies. Without wishing to be bound by theory, comparisons of several strains of immune deficient mice indicate that the lack of T cells may be contributing to the ability for alveolar lung organoid cells to engraft efficiently in immunocompromised mice. This observation is novel and has implications for combining immunosuppressive drugs with cell-based therapy for lung diseases of the alveolar space. In addition, the transplanted alveolar cells can be reisolated and grown as alveolar organoids that express surfactant protein C, further indicating that these cells are functional.

Airway organoids or cells thereof are shown herein to functionally engraft into the alveolar space or the airway space.

It is further specifically contemplated herein to transplant human iPSC derived airway and alveolar organoid cells to the mouse models used herein to show human relevance. For example, mice transplanted with human cells can be a model for Coronavirus Disease-19 (COVID-19) and can permit screening of agents to treat COVID-19. It is specifically contemplated herein that primary human lung cells and/or iPS-derived lung cells can be transplanted into recipient mice suited for the study of SARS-CoV-2 infection or COVID-19 in vivo. This model is an improved model over the current COVID-19 model (hAEC2 transgenic mouse that expresses human AEC2 protein required for viral entry) because the mouse would express the full complement of genes expressed in lung cells, not just the hAEC2 gene as is true for current models. In addition, it is known that mice do not present with COVID-like illness, thought to be because they lack the human variant of the ACE2 receptor that is partially responsible for uptake of the virus. Thus, the mouse models contemplated herein are particularly advantageous because the transplanted cells are entirely human and comprise human-specific expression patterns of multiple genes that could be involved in SARS-CoV-2 infection and/or COVID-19 disease or lung injury.

The studies presented herein are novel in that the inventors focus on the delivery of cultured adult epithelial lung organoid cells, whereas others have focused either on rare sorted cells, mixed lung populations of adult mouse cells, mixed populations of embryonic mouse cells, or commercially available human lung cells. It is further specifically contemplated herein to deliver human iPSC-derived lung epithelial organoid cells, which has not been shown before. Furthermore, the inventors' focus on combining immunosuppressive drugs with cell-based therapy for lung diseases has not been explored.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this disclosure belongs.

As used herein, the term 'lung organoid' refers to a self-assembling structure generated from lung epithelial progenitor cells cultured in a 3-dimensional (3D) culture system, with or without mesenchymal support cells.

As used herein, the term "airway organoid" refers to a 3-dimensional, self-assembled cell structure produced in vitro from cells comprising the markers CD31−/CD45−, Epcam+ and Sca1+ for murine cells, or CD31−/CD45−, Epcam+, and NGFR+ for human cells. The term "airway organoids" encompasses such structures comprising lung epithelial cell such as bronchiolar cells (e.g., club cells), or bronchoalveolar cells and, if desired, other supporting cells such as stromal cells or mesenchymal cells. Airway organoids are typically grown in a cell culture medium using a gelatinous protein substrate such as Matrigel™ or growth-factor reduced Matrigel™. In some embodiments, the airway organoid is treated to remove cell culture medium or protein substrates prior to administration or transplantation into a subject. When an airway organoid is composed primarily of bronchiolar cells (e.g., club cells), it is referred to herein as a "bronchiolar organoid." This naming convention also applies to "bronchoalveolar organoids" and "alveolar organoids." Typically, an "airway organoid" will comprise at least two different lung epithelial cells such as alveolar cells and bronchiolar cells, or alveolar cells and bronchoalveolar cells, or bronchiolar cells and bronchoalveolar cells, or bronchiolar cells, basal cells, and other airway type cells that are not alveolar.

In some embodiments, the term "alveolar organoid" refers to a 3-dimensional, self-assembled cell structure produced in vitro from cells comprising the markers CD31−/CD45−, Epcam+ and Sca1− for murine cells, or CD31−/CD45−, Epcam+, and HTII-280+ for human cells. The term "alveolar organoids" encompasses such structures comprising alveolar cells, and optionally supporting cells such as stromal cells, if desired. Alveolar organoids are typically grown in a cell culture medium using a gelatinous protein substrate such as Matrigel™ or growth-factor reduced Matrigel™. In some embodiments, the alveolar organoid is treated to remove cell culture medium or protein substrates prior to administration or transplantation into a subject.

As used herein, the term "isolated cell thereof" or "cell thereof" when used in reference to an airway or alveolar organoid, refers to a cell isolated by dissociating or partially dissociating the airway or alveolar organoid (e.g., using dispase) and optionally selecting for a particular cell type (i.e., an alveolar cell, a bronchiolar cell or a bronchoalveolar cell). Isolated cells useful for transplantation or administration to a subject will generally lack cell culture medium or other in vitro culture growth substrates.

By the term "differentiated cell" is meant any primary cell that is not, in its native form, pluripotent as that term is defined herein. Those of ordinary skill in the art recognize that there is a spectrum of differentiation from totipotent or pluripotent cells at one end to fully differentiated cells that do not have the normal capacity to naturally differentiate to any other phenotype. In some embodiments, the term "differentiated cell" also refers to a cell of a more specialized cell type derived from a cell of a less specialized cell type (e.g., from an undifferentiated cell or a reprogrammed cell) where the cell has undergone a cellular differentiation process.

As used herein, the term "positive for" when referring to a cell positive for a marker (e.g., acetylated alpha tubulin positive or surfactant protein C positive) means that a cell surface marker is detectable above background levels on the cell using immunofluorescence microscopy or flow cytometry methods, such as fluorescence activated cell sorting (FACS). Alternatively, the terms "positive for" or "expresses a marker" means that expression of mRNA encoding a cell surface or intracellular marker is detectable above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "expresses" a marker (or is "positive for a marker") has an expression level detectable above the expression level determined for the negative control for that marker. Exemplary markers useful for identifying subsets of lung epithelial cells are shown in FIGS. 28A and 29B.

As used herein, the term "negative for" when referring to a cell negative for a marker (or the term "does not express") means that a cell surface marker cannot be detected above background levels on the cell using immunofluorescence microscopy or flow cytometry methods, such as fluorescence activated cell sorting (FACS). Alternatively, the terms "negative" or "does not express" means that expression of the mRNA for an intracellular marker or cell surface marker cannot be detected above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "does not express" a marker appears similar to the negative control for that marker. In some embodiments, it is advantageous to detect the loss of stem cell markers during step-wise differentiation of stem cells or progenitor cells to airway organoids or alveolar organoids.

As used herein, the terms "dedifferentiation" or "reprogramming" or "retrodifferentiation" refer to the process that generates a cell that re-expresses a more stem cell phenotype or a less differentiated phenotype than the cell from which it is derived. For example, a multipotent cell can be dedifferentiated to a pluripotent cell. That is, dedifferentiation shifts a cell backward along the differentiation spectrum of totipotent cells to fully differentiated cells. Typically, reversal of the differentiation phenotype of a cell requires artificial manipulation of the cell, for example, by expressing stem cell-specific mRNA and/or proteins. Reprogramming is not typically observed under native conditions in vivo or in vitro.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. Thus, apart from the sperm and ova, the cells from which they are made (gametocytes) and undifferentiated stem cells—all other cells in the mammalian body are somatic cells: internal organs, skin, bones, blood, and connective tissue are all substantially made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell (e.g., to generate an iPSC) can be performed both in vivo and in vitro (where in vivo is practiced when a differentiated cell is present within a subject, and where in vitro is practiced using an isolated differentiated cell maintained in culture).

The term "substantially pure," with respect to a particular cell population, refers to a population of cells that is at least about 75%, preferably at least about 85%, more preferably at least about 90%, and most preferably at least about 95% pure or more, with respect to the cells making up a total cell population. That is, the terms "substantially pure" or "essentially purified," with regard to a population of alveolar cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not alveolar cells as defined by the terms herein.

The terms "enriching" or "enriched" are used interchangeably herein and mean that the yield (fraction) of cells of one type, such as human alveolar cell compositions and cells for use in the methods described herein, is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

The term "marker" as used herein is used to describe the characteristics and/or phenotype of a cell. Markers can be used for selection of cells comprising characteristics of interest and can vary with specific cells. Markers are characteristics, whether morphological, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological characteristics. In one embodiment, the marker is a cell surface marker. Exemplary cell surface markers expressed on alveolar cells include, but are not limited to, Hopx+, Igfbp+, surfactant protein C). In some embodiments, the absence of a cell surface marker can be used to distinguish an alveolar cell from another lung cell or a cell of another lineage (e.g., a thyroid or brain lineage).

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level or level below detectable limits using a standard assay as compared to a reference sample), or any decrease between 10-100% as compared to a reference level.

The terms "increased", "increase" or "enhance" or "higher" are all used herein to generally mean an increase by a statistically significant amount; for the avoidance of any doubt, the terms "increased", "increase" or "enhance" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "agent" refers to any entity which is normally absent or not present at the levels being administered, in the cell. An agent can be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The terms "patient", "subject" and "individual" are used interchangeably herein, and refer to an animal, particularly a human, to whom treatment including prophylactic treatment is provided. The term "subject" as used herein refers to human and non-human animals. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "effective amount" includes within its meaning a sufficient amount of a cell composition or agent composition to provide the desired effect. For example, an effective amount using the methods as disclosed herein would be considered as the amount sufficient to reduce a symptom of a pulmonary disease, e.g., cystic fibrosis by at least 10%. Further, an effective amount as used herein would also include an amount sufficient to prevent or delay the development of a symptom experienced by a subject with a pulmonary disease, e.g. CF, or alter the course of a symptom disease (for example but not limited to, slow the progression or development of at least one symptom experienced by a subject with a pulmonary disease, e.g., CF), or reverse at least one symptom experienced by a subject with a pulmonary disease, e.g. CF. In one embodiment, an "effective amount" refers to a concentration of the active agent that is higher than the concentration necessary to produce the desired effect in 50% of a test population (i.e., EC50).

In certain aspects, the term "effective amount" can refer to an amount of the SARS-CoV-2 virus for use in infecting a mouse having engrafted human lung cells for modelling COVID-19 induced lung injury. Such effective viral amounts include an amount that produces detectable lung injury from SARS-CoV-2 or a higher effective amount that mimics severe lung damage that mimics the damage observed in subjects having moderate to severe COVID-19 illness that are admitted to the hospital or the ICU unit.

As used herein, the term "treating" includes administering a population of organoids or isolated cells, or compositions thereof as disclosed herein to a subject that results in functional engraftment of at least one cell into the subject's lungs. In one embodiment, the term "treating" refers to the reduction of at least one symptom experienced by a subject with a pulmonary disease, e.g., CF. Exemplary symptoms of lung diseases can include shortness of breath, pain upon breathing, labored breathing, reliance on externally administered oxygen, etc.

As used herein, the term "functionally engrafts" refers to the ability of transplanted cells to perform appropriate cell functions akin to the function of their corresponding endogenous cells. At a minimum, functionally engrafted cells will survive a desired region of the lung in a transplanted subject for at least 24 h after transplantation. In other embodiments, functionally engrafted cells will replace damaged cells (e.g., damaged alveolar cells) and can perform the functions of e.g., endogenous alveolar cells. In other embodiments, functionally engrafted cells adopt transcriptional profiles that are more similar to endogenous cells than the cells of the organoid administered to the subject. In preferred embodiments, functionally engrafted cells can reduce or inhibit at least one symptom of a lung injury, or lung disease/disorder.

The term "statistically significant" or "significantly" refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term "standard deviation" is a measure of the dispersion of a set of data from its mean. The more spread apart the data, the higher the deviation. Standard deviation is calculated as the square root of variance and can be calculated by one of ordinary skill in the art.

As used herein, the terms "administering," "introducing" and "transplanting" are used interchangeably, and refer to the placement of a population of organoids or isolated cells, or compositions thereof as disclosed herein into a subject by a method or route which results in at least partial localization of the population of organoids or isolated cells, or compositions thereof e.g. the lung or airways. A population of organoids or isolated cells, or compositions thereof as of the present disclosure can be administered by any appropriate route which results in an effective treatment in the subject.

The term "genetically modified" refers to an alteration of the exogenous nucleic acid that has been introduced by a process involving the hand of man (or a descendant of such a cell that has inherited at least a portion of the nucleic acid). The nucleic acid may for example contain a sequence that is exogenous to the cell, it may contain native sequences (e.g., sequences naturally found in the cells) but in a non-naturally occurring arrangement (e.g., a coding region linked to a promoter from a different gene), or altered versions of native sequences, etc., e.g., a correction of a genetic lesion or mutation in the CFTR gene that causes CF. The process of transferring the nucleic acid into the cell is referred to as "transducing a cell" and can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert. In some embodiments, a pharmaceutically acceptable carrier does not comprise cell culture medium or research grade cell culture components such as Matrigel™.

As used herein the term "comprising" or "comprises" is used in reference to compositions, methods, and respective component(s) thereof, that are essential to the disclosure, yet open to the inclusion of unspecified elements, whether essential or not. Accordingly, compositions or methods "comprising" one or more recited elements may include other elements not specifically recited. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Thus, the use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean ±1%. The present disclosure is further explained in detail by the following, including the Examples, but the scope of the disclosure should not be limited thereto.

Although any known methods, devices, and materials may be used in the practice or testing of the invention, the methods, devices, and materials in this regard are disclosed herein.

Embryonic Stem Cells and Adult Stem Cells

Provided herein, in some aspects, are methods of generating human alveolar organoids or human airway organoids from both embryonic stem cells, induced pluripotent stem cells and primary adult lung progenitor cells. In one embodiment, the methods provided herein relate to generation of human alveolar organoids or human airway organoids from induced pluripotent stem cells. Alternatively, in some embodiments, the methods provided herein do not encompass generation of human alveolar organoids or human airway organoids from embryonic stem cells or any other cells of human embryonic origin.

Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). Thus, a detailed discussion on embryonic stem cells is not included herein.

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli.

In contrast, adult stem cells are stem cells which are derived from tissues of a post-natal or post-neonatal organism or from an adult organism are also known in the art. An adult stem cell is structurally distinct from an embryonic stem cell not only in markers it does or does not express relative to an embryonic stem cell, but also by the presence of epigenetic differences, e.g. differences in DNA methylation patterns. In some embodiments, progenitor cells committed to the lung lineage (e.g., basal airway progenitor cells) or differentiated lung epithelial cells (i.e., alveolar cells, bronchiole cells, bronchoalveolar cells, primary airway cells) can be used to produce human airway organoids or human alveolar organoids for use in the methods and compositions described herein.

Marker-specific agents can be used to recognize stem cell markers, for instance labeled antibodies that recognize and bind to cell-surface markers or antigens on desired stem cells. Antibodies or similar agents specific for a given marker, or set of markers, can be used to separate and isolate the desired stem cells using fluorescent activated cell sorting (FACS), panning methods, magnetic particle selection, particle sorter selection and other methods known to persons skilled in the art, including density separation (Xu et al. (2002) Circ. Res. 91:501; U.S.S.N. 20030022367) and separation based on other physical properties (Doevendans et al. (2000) J. Mol. Cell. Cardiol. 32:839-851).

Induced Pluripotent Stem Cells (iPSCs)

In some embodiments, the human alveolar organoids or human airway organoids described herein are derived from isolated pluripotent stem cells. An advantage of using iPSCs is that the cells can be derived from the same subject to which the human alveolar or airway organoids (or an isolated cell thereof) are to be administered. That is, a somatic cell can be obtained from a subject, reprogrammed to an induced pluripotent stem cell, and then re-differentiated into a human alveolar organoid or human airway organoid to be administered to the subject (e.g., autologous cells). Since the alveolar or airway organoids are essentially derived from an autologous source, the risk of engraftment rejection or allergic responses is reduced compared to the use of cells from another subject or group of subjects. In some embodiments, the alveolar organoids or airway organoids are derived from non-autologous sources. In addition, the use of iPSCs negates the need for cells obtained from an embryonic source. Thus, in one embodiment, the stem cells used in the disclosed methods to generate airway organoids or alveolar organoids are not embryonic stem cells.

The somatic cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein. Reprogramming methodologies, and methods for enhancing such reprogramming, for generating pluripotent cells are well understood and described in the art, and are not described in detail herein.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for reprogramming: the term "somatic cells" refers to any cells forming the body of an organism, excluding germline cells. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, a hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, lung, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of human alveolar organoids to be used in the therapeutic treatment of disease, it is desirable, but not required, to use somatic cells isolated from the patient being treated. For example, somatic cells involved in diseases, and somatic cells participating in therapeutic treatment of diseases and the like can be used. In certain embodiments, the reprogrammed cells (or ESCs) are genetically modified, for example, to correct an inherent defect causing a lung disease or disorder. Cystic fibrosis is one such example where cells reprogrammed from a subject with CF are then genetically modified to correct a mutation in the cystic fibrosis transmembrane conductance regulator (CFTR) gene. These cells can then be re-differentiated and administered to the subject for repair of the lung tissue and reduction in the symptoms of cystic fibrosis. Techniques for modifying the genome include, for example, CRISPR/Cas, zinc fingers, and transcription activator-like effector nucleases (TALENs). Such techniques are well known in the art and are thus not described in detail herein.

In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fth117; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tc11); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Generation of Alveolar Organoids or Airway Organoids from Lung Cells

It is specifically contemplated herein that the alveolar organoid compositions or airway organoid compositions described herein are generated from a lung stem cell (e.g., a bronchoalveolar stem cell; a basal airway stem cell), an iPSC, an ESC or a differentiated lung cell (i.e., alveolar cell, bronchoalveolar cell, bronchiole cell, primary airway cell, pneumocyte type I or pneumocyte type II). Such lung cells or lung stem cells can be derived or isolated from lung tissue samples and/or a lung stem cell line. In one embodiment of all aspects of the compositions and methods described, the lung cells or lung stem cell(s) can be isolated using any method known to one of skill in the art or according to the method described herein. For example, fine needle aspiration for a small lung tissue sample from a live subject. In some embodiments of all aspects of the compositions and methods described, the lung stem cells are derived ex vivo from other cells, such as embryonic stem cells, induced pluripotent stem cells (iPS cells) or adult pluripotent cells. In some embodiments of any of the aspects, the lung cells or stem cells can be isolated from a subject. Lung cells can be isolated from lung tissue samples by any method known in the art. Methods of dissociating individual cells from a tissue sample are known in the art, e.g., in U.S. Pat. No. 7,547,674 and U. S. Patent Application U.S. 2006/0239983, 2009/0148421, and 2009/0180998. These references are herein incorporated by reference in their entirety.

For the production of airway organoids, lung cells to be cultured to form airway organoids are selected for the marker profile CD31/CD45−, Epcam+, and Sca1+ for murine cells, or CD31−/CD45−, Epcam+, and NGFR+ for human cells. For the production of alveolar organoids, lung cells to be cultured to form alveolar organoids are selected for the marker profile CD31/CD45−, Epcam+, and Sca1− for murine cells, or CD31−/CD45−, Epcam+, and HTII-280+ for human cells.

It is recognized that isolation of human lung stem cells from an adult subject is particularly difficult as very few true lung stem cells are present in the adult lung. Thus, in some embodiments the lung stem can be bronchoalveolar stem cells (BASCs), a human lung stem cell or basal airway stem cells. BASCs are readily identified by one of skill in the art, e.g., by use of the cell markers Clara; CCSP; and SPC, see, e.g., Lee et al. Cell 2014 156:440-455.

In some embodiments, the lung cells comprise pneumocyte/alveolar type 1 cells or pneumocyte/alveolar type 2 cells for the starting cell from which the alveolar or airway organoid is derived. In order to isolate alveolar type 2 cells (AEC2s) for organoid culture, FACS can be employed to detect genetic lineage tracing with a fluorescent reporter and/or the use of antibodies to bind surface markers such as e.g., $CD31^{neg}$, $CD45^{neg}$, $EpCAM^{med}$, $CD34^{neg}$, $Sca1^{neg}$, $CD24^{neg}$, and/or $Sftpc^{high}$. Human AEC2s are typically isolated with the use of a monoclonal antibody, HTII280, that is specific for human AEC2s (Gonzalez et al., 2010). From dissociated human lung, AEC2s are defined as being propidium iodide staining (PI)neg, CD31neg, CD45neg, EPCAMpos, HTII280pos. These cells can be isolated by either FACS or by magnetic bead sorting (MACS).

The methods described herein relate to differentiation of lung stem cells or lung cells to form organoids. Such lung cells can be directly isolated or derived in vitro from e.g., an iPSC or ESC. In one embodiment, the airway organoid comprises multiple cell types, such as surfactant producing cells (e.g., secretory cells and/or club cells), mucus producing cells (e.g., Goblet cells) and/or ciliated cells. These cell types are readily identified by phenotype and/or cell markers known in the art (e.g., by Immunofluorescence, histochemical staining, and/or FACS analysis). For example, ciliated cells are positive for acetylated tubulin and FOXJ1 and negative for CCSP, and Muc5a, Alician Blue, PAS. Club cells are positive for CCSP and negative for Acetylated tubulin, FOXJ1, Muc5a, Alician Blue, PAS. Goblet cells are positive for Muc5a Alician Blue and PAS, negative for FOXJ1 and acetylated tubulin, and may or may not be positive for CCSP.

In some embodiments of any of the aspects, the contacting step can occur while the cells are being cultured under conditions that support formation of alveolar organoids or airway organoids.

The methods described herein can further comprise the step of selecting for alveolar organoids or airway organoids. In some embodiments of any of the aspects, selecting for alveolar organoids can comprise size selection or selection for the presence of one or more markers. In some embodiments, selection for alveolar organoids can comprise selecting for organoids comprising both surfactant producing cells (e.g., secretory cells and/or club cells) and mucus producing cells (e.g., Goblet cells and/or ciliated cells). In some embodiments, the production of an alveolar or airway organoid is monitored by visual observation of formation of a 3-dimensional organoid structure.

Monitoring Differentiation of Alveolar or Airway Organoids

Provided herein are methods for differentiating lung cells to alveolar organoids or airway organoids in vitro. Such methods are exemplified in the Examples section herein. Also provided herein are compositions of alveolar or airway organoids having particular characteristics, such as the presence of one or more cell surface or other airway markers. Alternatively, or in addition, the alveolar organoid or airway organoid compositions described herein lack markers of embryonic stem cells or induced pluripotent stem cells.

With respect to methods relating to reprogramming somatic cells to iPSCs, cell surface markers, particularly stem cell surface markers, are useful with the methods and compositions described herein to identify or monitor the differentiation or dedifferentiation state of a cell. For example, during reprogramming of a somatic cell to an induced pluripotent stem cell the activation of stem cell markers can be used to confirm that the somatic cell has been dedifferentiated (either partially or completely). Alternatively, during differentiation of an ES cell or an iPSC to a human lung cell, the activation of lung-specific markers can be used to confirm the degree of differentiation that the stem cell has undergone. In addition, the activation or deactivation of particular lung-specific markers can be used to determine the presence or degree of multipotency of a human lung progenitor cell. This can be achieved by comparing the lung-specific markers present on, or expressed by the cell with the marker profile of lung cells during development and inferring the degree of multipotency of the differentiated cell based on the known degree of multipotency of the corresponding lung cell during embryonic development.

When monitoring the emergence of alveolar organoids in vitro, visual observation of alveolar organoid structure or the production of airway-like structures can be used as a phenotypic measure. Alveolar organoids comprise such airway-like structures surrounded by lung mesenchymal cells and comprise cells that stain positive for AECI and AECII markers. Alveolar organoids can be produced from alveolar type I (AEC1) or alveolar type II (AECII) cells. Where the lung alveolar organoids are produced from AEC2s, the 3D organoid structures that arise can contain the cell markers Ager+, Pdpn+, Hopx+ AEC1s in the interior and Sftpc+ cells on the outside.

Alternatively, genetic selection methods can be used, where a lung cell or reprogrammed cell can be genetically engineered to express a reporter protein operatively linked to a tissue-specific promoter and/or a specific gene promoter; therefore the expression of the reporter can be used for positive selection methods to isolate and enrich the desired lung stem cell during reprogramming or alveolar cell. For example, a fluorescent reporter protein can be expressed in the desired stem cell by genetic engineering methods to operatively link the marker protein to a promoter active in a desired stem cell (Klug et al. (1996) J. Clin. Invest. 98:216-224; U.S. Pat. No. 6,737,054). In some embodiments, cells from which the human alveolar organoids or airway organoids are derived are not modified using genetic means to include a marker protein. Other approaches for positive selection include drug selection, for instance as described by Klug et al., supra, involving enrichment of desired cells by density gradient centrifugation. Negative selection can be performed, selecting and removing cells with undesired markers or characteristics, for example fibroblast markers, epithelial cell markers etc.

Undifferentiated ES cells express genes that can be used as markers to detect the presence of undifferentiated cells. The polypeptide products of such genes can be used as markers for negative selection. For example, see U.S.S.N. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including, but not limited to, stage-specific embryonic antigen (SSEA)-3, SSEA-4, TRA-I-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. Undifferentiated human ES cell lines do not stain for SSEA-1, but differentiated cells stain strongly for SSEA-1. Methods for proliferating hES cells in the undifferentiated form are described in WO 99/20741, WO 01/51616, and WO 03/020920, the contents of which are herein incorporated by reference in their entireties.

Exemplary cell surface markers expressed on lung progenitor cells (i.e., cells that are partially reprogrammed or partially differentiated from an iPSC) include, but are not limited to, Sox2, Sox9, p63, FoxP2, ETV4/5, FoxA2, Nkx2.1, Gata6, ID2, CK5, NGFR, FoxJ1, CCSP, Scgb3a2, Muc5ac, T1a, Spc, and Scgn.

In some embodiments, it is desirable to "enrich" a population of cells. For example, enrichment of a given iPSC or lung stem cell prior to generating the alveolar organoids. An enriched population of cells refers to the percentage of cells (e.g., percent of cells) in a population of cells is at least 10% of the total number of cells in the population. For example, an enriched population comprises at least 15% human lung progenitor cells, at least 20%, at least 30%, at least 40%, at least 50%, at least 60%, at least 70%, at least 80%, at least 90%, at least 95%, at least 99% or even 100% of the population comprises human lung progenitor cells. In some embodiments, a population of cells comprises at least 100 cells, at least 500 cells, at least 1000 cells, at least $1\times10^4$ cells, at least $1\times10^5$ cells, at least $1\times10^6$ cells, at least $1\times10^7$ cells, at least $1\times10^8$ cells, at least $1\times10^9$ cells, at least $1\times10^{10}$ cells, at least $1\times10^{11}$ cells, at least $1\times10^{12}$ cells, at least $1\times10^{13}$ cells, at least $1\times10^{14}$ cells, at least $1\times10^{15}$ cells, or more. In some embodiment, "enrichment" is determined by assessing the proportion of cells in the population compared to the proportion of the same cells in native lung tissue in vivo.

Treatment of Lung Disease/Disorders and Lung Injury

The methods and compositions provided herein relate to the generation and use of human alveolar organoids, airway organoids and cells thereof. Accordingly, provided herein are methods for the treatment and prevention of a lung injury or a lung disease or disorder in a subject in need thereof. The methods described herein can be used to treat, ameliorate, prevent or slow the progression of a number of lung diseases or their symptoms, such as those resulting in pathological damage to lung or airway architecture and/or alveolar damage. The terms "respiratory disorder," "respiratory disease," "lung disease," "lung disorder," "pulmonary disease," and "pulmonary disorder," are used interchangeably herein and refer to any condition and/or disorder relating to respiration and/or the respiratory system, including the lungs, pleural cavity, bronchial tubes, trachea, upper respiratory tract, airways, or other components or structures of the airway system.

In one embodiment, the respiratory disease comprises COVID-19. Coronavirus disease 2019 (COVID-19) is a respiratory and systemic illness caused by 2019 Novel Coronavirus (2019-nCoV or SARS-CoV-2) where a high proportion of infected subjects present with severe symptoms and deaths. Typically, with most respiratory viruses, people are thought to be most contagious when they are most symptomatic (the sickest). With SARS-CoV-2, however, there have been reports of spread from an infected patient with no symptoms to a close contact. In addition, COVID-19 can cause severe illness of otherwise healthy subjects of any age, although immune compromised individuals and the elderly are still the highest risk population.

Other lung diseases include, but are not limited to, bronchopulmonary dysplasia (BPD), chronic obstructive pulmonary disease (COPD), cystic fibrosis, bronchiectasis, cor pulmonale, pneumonia, lung abscess, acute bronchitis, chronic bronchitis, emphysema, pneumonitis (e.g., hypersensitivity pneumonitis or pneumonitis associated with radiation exposure), alveolar lung diseases and interstitial lung diseases, environmental lung disease (e.g., associated with asbestos, fumes or gas exposure), aspiration pneumonia, pulmonary hemorrhage syndromes, amyloidosis, connective tissue diseases, systemic sclerosis, ankylosing spondylitis, pulmonary actinomycosis, pulmonary alveolar proteinosis, pulmonary anthrax, pulmonary edema, pulmonary embolus, pulmonary inflammation, pulmonary histiocytosis X, pulmonary hypertension, surfactant deficiencies, pulmonary hypoplasia, pulmonary neoplasia, pulmonary nocardiosis, pulmonary tuberculosis, pulmonary veno-occlusive disease, rheumatoid lung disease, sarcoidosis, postpneumonectomy, Wegener's granulomatosis, allergic granulomatosis, granulomatous vasculitides, eosinophilia, asthma and airway hyperreactivity (AHR) (e.g., mild intermittent asthma, mild persistent asthma, moderate persistent asthma, severe persistent asthma, acute asthma, chronic asthma, atopic asthma, allergic asthma or idiosyncratic asthma), allergic bronchopulmonary aspergillosis, chronic sinusitis, pancreatic insufficiency, lung or vascular inflammation, bacterial or viral infection, e.g., *Haemophilus influenzae, S. aureus, Pseudomonas aeruginosa* or respiratory syncytial virus (RSV) infection or an acute or chronic adult or pediatric respiratory distress syndrome (RDS) such as grade I, II, III or IV RDS or an RDS associated with, e.g., sepsis, pneumonia, reperfusion, atelectasis or chest trauma.

Chronic obstructive pulmonary diseases (COPDs) include those conditions where airflow obstruction is located at upper airways, intermediate-sized airways, bronchioles or parenchyma, which can be manifested as, or associated with, tracheal stenosis, tracheal right ventricular hypertrophy pulmonary hypertension, polychondritis, bronchiectasis, bronchiolitis, e.g., idiopathic bronchiolitis, ciliary dyskinesia, asthma, emphysema, connective tissue disease, bronchiolitis of chronic bronchitis or lung transplantation.

The methods described herein can also be used to treat or ameliorate acute or chronic lung diseases/disorders or their symptoms or complications, including airway epithelium injury, airway smooth muscle spasm or airway hyperresponsiveness, airway mucosa edema, increased mucus secretion, excessive T cell activation, or desquamation, atelectasis, cor pulmonale, pneumothorax, subcutaneous emphysema, dyspnea, coughing, wheezing, shortness of breath, tachypnea, fatigue, decreased forced expiratory volume in the 1st second ($FEV_1$), arterial hypoxemia, respiratory acidosis, inflammation including unwanted elevated levels of mediators such as IL-4, IL-5, IgE, histamine, substance P, neurokinin A, calcitonin gene-related peptide or arachidonic acid metabolites such as thromboxane or leukotrienes ($LTD_4$ or $LTC_4$), and cellular airway wall infiltration, e.g., by eosinophils, lymphocytes, macrophages or granulocytes.

Any of these and other respiratory or pulmonary conditions or symptoms are known in the art. See e.g., The Merck Manual, 17th edition, M. H. Beers and R. Berkow editors, 1999, Merck Research Laboratories, Whitehouse Station, N.J., ISBN 0911910-10-7, or in other references cited herein.

Organoid cell type may depend on the disease that is being treated. In one embodiment, a disease affecting the alveolar space will require alveolar organoids. In one embodiment, a disease affecting the airways will require airway organoids. In one embodiment, diseases affecting the alveolar space and/or airway will require a combination of alveolar and airway organoids. Exemplary diseases of the Alveolar space or airway are provided herein in Table 1.

TABLE 1

Diseases of the Alveolar space or airway

| | Affected Region of Lung |
|---|---|
| Surfactant protein deficiency | Alveolar space |
| Hermansky-Pudlak Syndrome | Alveolar space |
| Pulmonary Fibrosis | Alveolar space |
| COPD | Airway |
| Cystic Fibrosis | Airway |
| ARDS | Alveolar space |
| Bronchiolitis | Airway |
| Bronchopulmonary Dysplasia | Alveolar space |

Airway organoids, alveolar organoids or cells thereof can be implanted or administered directly to the respiratory airways, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of alveolar or airway organoids or cells thereof are administered directly to the lungs of an infant suffering from bronchopulmonary dysplasia by intra-tracheal administration. In other embodiments, alveolar organoids, airway organoids or cells thereof can be administered via an indirect systemic route of administration, such as an intraperitoneal or intravenous route, however this is not a preferred method of administration. In some embodiments, the engrafted cells have a similar transcription pattern as their corresponding endogenous cells.

When provided prophylactically, alveolar organoids, airway organoids or cells thereof as described herein can be administered to a subject in advance of any symptom of a lung disorder, e.g., an asthma attack or to a premature infant. Accordingly, the prophylactic administration of an airway organoid or alveolar organoid serves to prevent a lung disorder, as disclosed herein.

When provided therapeutically, alveolar organoids, airway organoids or cells thereof are administered at (or after) the onset of a symptom or indication of a lung disorder, e.g., upon the onset of COPD, or detection of COVID-19 induced lung injury.

In some embodiments of the aspects described herein, the alveolar organoids, airway organoids or cells thereof being administered according to the methods described herein comprises allogeneic alveolar organoids, airway organoids or cells thereof obtained from one or more donors. As used herein, "allogeneic" refers to a lung cell or biological sample comprising lung cells used to generate alveolar or airway organoids that are obtained from one or more different donors of the same species, where the genes at one or more loci are not identical. For example, alveolar organoids, airway organoids or cells thereof being administered to a subject can be derived from umbilical cord blood obtained from one more unrelated donor subjects, or from one or more non-identical siblings. In some embodiments, "syngeneic" lung cell populations can be used for generating alveolar or airway organoids, such as those obtained from genetically identical animals, or from identical twins. In other embodiments of this aspect, the lung cells used to generate the alveolar or airway organoids are "autologous" cells; that is, the alveolar organoids, airway organoids or cells thereof are derived from cells obtained or isolated from a subject and administered to the same subject, i.e., the donor and recipient are the same.

In one embodiment, engrafted exogenous lung cells are detected using standard techniques after administration. For example, the exogenous cells can be detected in a lung biopsy using cell markers specific to this population as described herein.

In one embodiment, engrafted exogenous lung cells are not detected using standard techniques after administration.

In one embodiment, the presence of engrafted exogenous lung cells after administration is assessed by examining the subject for various beneficial outcomes of the organoid cell-based therapy. In one embodiment, presence of engrafted exogenous lung cells after administration is confirmed by having at least one beneficial outcomes of the organoid cell-based therapy. For example, one can determine if the subject receiving a successful engraftment has an increased oxygen saturation, e.g., as measured by a pulse oximeter; and improved spirometry to measure how much and how quickly air can move in and out of lungs; an improved lung volume test to assess the amount of air a subject can hold in their lungs and the amount of air that remains after the subject exhales; an improved Gas diffusion test that measures how oxygen and other gases move from the lungs to the bloodstream; and improved exercise stress test that assesses how exercise affects lung function; or an Arterial Blood Gas that measures the pH and levels of O2 and CO2 from an artery. In one embodiment, the beneficial outcome is at least 5%, 10%, 15%, 20%, 25%, 30%, 35%, 40%, 45%, 50%, 55%, 60%, 65%, 70%, 75%, 80%, 85%, 90%, 95%, 99% or more as compared to prior to administration. For example, engraftment can be confirmed if the subject has an oxygen saturation of 90% prior to administration, and 98% after administration.

Pharmaceutically Acceptable Carriers

The methods of administering alveolar organoids, airway organoids or cells thereof to a subject as described herein involve the use of therapeutic compositions comprising such organoids or cells thereof. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. At a minimum, the pharmaceutically acceptable carrier will comprise an osmolarity that permits retention of cell viability.

In general, the alveolar organoids, airway organoids or cells thereof described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the human alveolar organoids, human airway organoids, or cells thereof as described herein using routine experimentation.

A cell composition comprising airway organoids, alveolar organoids or cells thereof can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Immunosupressive Agents

In some embodiments, the subject being administered the airway or alveolar organoids as described herein, is also treated with an immunosuppressive agent. In certain aspects, the engraftment of the airway organoid, alveolar organoid or cell thereof is improved by treatment with an immunosuppressive agent. For example, the number or percentage of engrafted cells can be increased when the subject is also treated with an immunosuppressive agent. Accordingly, in some embodiments the percentage of engrafted cells is at least 10% higher when the subject is treated with an immunosuppressive agent than the number of cells engrafted in the absence of the immunosuppressive agent (e.g., at least 20% more, at least 30% more, at least 40% more, at least 50% more, at least 60% more, at least 70% more, at least 80% more, at least 90% more, at least 95% more, at least 98% more, at least 1-fold more, at least 2-fold more, at least 10-fold or more cells engraft in the presence of the immunosuppressive agent than in the absence.

In some embodiments, the method of transplantation as described herein further comprises administering at least one immunosuppressive therapeutic. Exemplary immunosuppressive therapeutics can include, but are not limited to, prednisone, budesonide, prednisolone, tofacitinib, cyclosporine, tacrolimus, sirolimus, everolimus, azathioprine, leflunomide, mycophenolate, abatacept, adalimumab, anakinra, certolizumab, etanercept, golimumab, infliximab, ixekizumab, natalizumab, rituximab, secukinumab, tocilizumab, ustekinumab, vedolizumab, basiliximab, or daclizumab. In certain embodiments, the immunosuppressive therapeutic is selected from a class of therapeutics including, but not limited to, corticosteroids (e.g., prednisone), Janus kinase inhibitors (e.g., tofacitinib), calcineurin inhibitors (e.g., cyclosporine), mTOR inhibitors (e.g., sirolimus), IMDH inhibitors (e.g., azathioprine), biologic immunosuppressives (e.g., abatacept), or immunosuppressive monoclonal antibodies (e.g., basiliximab).

In one embodiment of any aspect, the method further comprises administering at least one additional therapeutic for the lung disease or disorder. Such agents can improve engraftment or can be used to aid in reduction of symptoms of the lung disease or disorder.

The immunosuppressive agent can be administered prior to transplantation, during transplantation or following transplantation. It is specifically contemplated herein that the subject is treated with an immunosuppressive agent, at a minimum, until the cells have successfully engrafted. In other embodiments, the immunosuppressive agent is administered on a regular basis to ensure the engrafted cells are not rejected by the recipient or subject.

Administration and Efficacy

Provided herein are methods for treating a lung disease, a lung disorder, or a lung injury comprising administering alveolar organoids, airway organoids, or cells thereof to a subject in need thereof.

Measured or measurable parameters of disease or treatment efficacy include clinically detectable markers of disease, for example, elevated or depressed levels of a clinical or biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

The term "effective amount" as used herein refers to the amount of alveolar organoids or cells thereof needed to alleviate at least one or more symptom of the lung injury or the lung disease or disorder, and relates to a sufficient amount of a composition to provide the desired effect, e.g., treat a subject having COVID-19 induced-injury, smoking-induced injury or cystic fibrosis. The term "therapeutically effective amount" therefore refers to an amount of alveolar organoids, airway organoids or cells thereof or a composition comprising alveolar organoids, airway organoids or cells thereof that is sufficient to promote a particular effect when administered to a typical subject, such as one who has or is at risk for a lung disease or disorder. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the lung tissue prior to administering the cells according to the methods described herein. In some embodiments, the subject is first diagnosed as being at risk of developing lung disease or disorder prior to administering the cells. For example, a premature infant can be at a significant risk of developing a lung disease or disorder. In some embodiments, a clinician will receive the results of an assay that indicate the subject has a lung disease or disorder, a lung injury, COVID-19, with or without co-presenting immune deficiency (i.e., immune compromised) prior to administration or transplantation of human airway organoids, human alveolar organoids or cells thereof.

For use in the various aspects described herein, an effective amount of dissociated alveolar organoids, airway organoids or cells thereof, comprises at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The alveolar organoids, airway organoids or cells thereof can be derived from one or more donors, or can be obtained from an autologous source. In some embodiments of the aspects described herein, the stem cells are expanded in culture prior to generation of alveolar organoids or airway organoids and the subsequent administration to a subject in need thereof.

Exemplary modes of administration for use in the methods described herein include, but are not limited to, injection, intrapulmonary (including intranasal and intratracheal) infusion, inhalation as an aerosol (including intranasal), and implantation (with or without a scaffold material). "Injection" includes, without limitation, intravenous, intramuscular, intraarterial, intradermal, intraperitoneal, transtracheal, intratracheal and subcutaneous. The phrases "parenteral administration" and "administered parenterally" as used herein, refer to modes of administration other than enteral and topical administration, usually by injection, and includes, without limitation, intravenous, intraperitoneal, intramuscular, intraarterial, intradermal, transtracheal, and subcutaneous administration. As will be appreciated by those of skill in the art, administration routes that permit direct administration of the cells to lung tissue is preferred over other routes. The human alveolar organoids or cells thereof described herein can be administered to a subject having any lung disease or disorder by any appropriate route which results in an effective treatment in the subject.

In some embodiments, a therapeutically effective amount of alveolar organoids, airway organoids or cells thereof is administered using intrapulmonary administration, such as an intranasal or intratracheal route, or as described herein in the Examples section. As defined herein, "intrapulmonary" administration or delivery refers to all routes of administration whereby the alveolar organoids, airway organoids or cells thereof is/are administered in a way that results in direct contact of these cells with the airways of a subject, including, but not limited to, transtracheal, intratracheal, and intranasal administration. In some such embodiments, the cells are injected into the nasal passages or trachea. In some embodiments, the cells are directly inhaled by a subject. In some embodiments, intrapulmonary delivery of cells includes administration methods whereby cells are administered, for example as a cell suspension, to an intubated subject via a tube placed in the trachea or "tracheal intubation."

As used herein, "tracheal intubation" refers to the placement of a flexible tube, such as a plastic tube, into the trachea (e.g., orotracheal intubation via the mouth/throat). In some embodiments, cells are administered to a subject having "nasotracheal intubation," which is defined as a tracheal intubation where a tube is passed through the nose, larynx, vocal cords, and trachea.

In some embodiments of the aspects described herein, a subject having a lung disorder is first diagnosed or selected prior to administration of the cells.

In some embodiments of the aspects described herein, one or more routes of administration are used in a subject to achieve distinct effects. For example, alveolar organoids, airway organoids or cells thereof can be administered to a subject by both intratracheal and inhalation administration routes, for example, for treating or repairing lung epithelium or replacing damaged alveolar cells. In such embodiments, different effective amounts of the alveolar organoids or cells thereof can be used for each administration route.

Where aerosol administration is to be used, nebulizer devices require formulations suitable for dispensing the particular composition. The choice of formulation will depend upon the specific composition used and the number of alveolar organoids, airway organoids or cells thereof to be administered; such formulations can be adjusted by the skilled practitioner. However, as an example, where the composition is alveolar organoids, airway organoids or cells thereof in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells.

Typically, each formulation for aerosol delivery via a nebulizer is specific to the type of device employed and can involve the use of an appropriate propellant material, in addition to the usual diluents, adjuvants and/or carriers useful in therapy.

In some embodiments, additional agents to aid in treatment of the subject can be administered before or following treatment with the alveolar organoids, airway organoids or cells thereof described herein. Such additional agents can be used to prepare the lung tissue for administration of the alveolar organoids, airway organoids or cells thereof. Alternatively, the additional agents can be administered after the alveolar organoids, airway organoids or cells thereof to support the engraftment and growth of the administered cell in the damaged lung. Such additional agents can be formulated for use with a metered-dose inhaler device, which generally comprises a finely divided powder containing a protein or small molecule suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant.

Formulations for dispensing from a powder inhaler device can comprise a finely divided dry powder containing proteins or small molecules and can also include a bulking agent, such as lactose, sorbitol, sucrose, or mannitol in amounts which facilitate dispersal of the powder from the device, e.g., 50 to 90% by weight of the formulation. Protein agents should most advantageously be prepared in particulate form with an average particle size of less than 10 μm (or microns), most preferably 0.5 to 5 μm, for most effective delivery to the distal lung.

Nasal delivery of protein or other agents in addition to alveolar organoids, airway organoids or cells thereof is also contemplated. Nasal delivery allows the passage of the protein or other agent to the blood stream directly after administering the therapeutic product to the nose, without the necessity for deposition of the product in the lung. Exemplary formulations for nasal delivery include those with dextran or cyclodextran.

The efficacy of treatment can be determined by the skilled clinician. However, a treatment is considered "effective treatment," as the term is used herein, if any one or all of the symptoms, or other clinically accepted symptoms or markers of lung disease, lung injury and/or a lung disorder are reduced, e.g., by at least 10% following treatment with a composition comprising alveolar organoids, airway organoids or cells thereof as described herein. Methods of measuring these indicators are known to those of skill in the art and/or described herein.

Indicators of lung disease or lung disorder, or lung injury include functional indicators, e.g., measurement of lung capacity and function, and oxygen saturation (e.g., tissue oxygen saturation or systemic arterial oxygen saturation), as well as biochemical indicators.

For idiopathic pulmonary fibrosis, for example, improved symptoms include an increase of at least 10% of predicted forced vital capacity (FVC) relative to values prior to treatment. FVC is the total volume of air expired after a full inspiration. Patients with obstructive lung disease usually have a normal or only slightly decreased vital capacity. Patients with restrictive lung disease have a decreased vital capacity.

Another measure is FEV1 (Forced Expiratory Volume in 1 Second). This is the volume of air expired in the first second during maximal expiratory effort. The FEV1 is reduced in both obstructive and restrictive lung disease. The FEV1 is reduced in obstructive lung disease because of increased airway resistance. It is reduced in restrictive lung disease because of the low vital capacity.

A related measure is FEV1/FVC. This is the percentage of the vital capacity which is expired in the first second of maximal expiration. In healthy patients the FEV1/FVC is usually around 70%. In patients with obstructive lung disease FEV1/FVC decreases and can be as low as 20-30% in severe obstructive airway disease. Restrictive disorders have a near normal FEV1/FVC.

Where necessary or desired, animal models of lung injury or lung disease can be used to gauge the effectiveness of a particular composition as described herein. As one example, the bleomycin-induced lung injury model of acute lung injury (ALI) can be used. Animal models of lung function are useful for monitoring bronchoconstriction, allergic response, late airway hyperresponsiveness in response to inhaled allergens, among other endpoints and can include, for example, head-out plethysmography or body-plethysmography models (see e.g., Hoymann, H G et al., *J Pharmacol Toxicol Methods* (2007) 55(1):16-26). Exemplary animal models for asthma, including models of allergic asthma (e.g., acute and chronic allergic asthma), are known in the art. See e.g., Nials and Uddin. (2008) *Dis Model Mech* 1:213-220; Zosky and Sly (2007) *Clin Exp Allergy* 37(7): 973-88; and Kumar and Foster. (2002) *Am J Respir Cell Mol Biol* 27(3):267-72. Animal models of pneumonia are reviewed by Mizgerd and Skerrett (2008) *Am J Physiol Lung Cell Mol Physiol* 294:L387-L398. In addition, small animal imaging can be applied to lung pathophysiologies (Brown R H, et al., *Proc Am Thorac Soc* (2008) 5:591-600).

Screening Assays

Human airway organoids, human alveolar organoids or mouse models generated by transplantation of the same are useful to screen for agents for the treatment of a lung disease or disorder or for improving culture conditions for alveolar organoids, airway organoids or cells thereof.

In some embodiments, the alveolar organoids, airway organoids or cells thereof can be used in methods, assays, systems and kits for the formation of alveolar organoids or airway organoids, or for the treatment of a lung disease or disorder. Where the alveolar organoids, airway organoids or cells thereof are derived from iPSCs, such assays for drug screening and toxicology studies have an advantage over existing assays because they are of human origin, and do not require immortalization of cell lines, nor do they require tissue from cadavers, which can poorly reflect the physiology of normal human cells. For example, the methods, assays, systems, and kits can be used to identify and/or test for agents useful in treating a lung disease or disorder, or for preventing/treating a lung injury.

In other embodiments, a mouse model of lung injury (e.g., COVID-19 induced lung injury) can be generated by infecting a recipient mouse, previously transplanted with human airway organoids, human alveolar organoids or cells thereof, with an effective amount of SARS-CoV-2 to induce a detectable lung injury, and screening for agents that can reduce the degree of, or prevent the onset of, COVID-19 induced lung injury. Such mouse models are advantageous over existing COVID-19 models because they can include engrafted cells of multiple different human lung cell types, particularly when the mouse models are generated using human airway organoids.

Also provided herein are methods for screening a test compound for biological activity, the method comprising (a) contacting alveolar organoids or cells thereof as described herein with a test compound and (b) determining any effect of the compound on the cell(s). In one embodiment, the screening method further comprises generating alveolar organoids, airway organoids or cells thereof as disclosed herein. The effect on the cell can be one that is observable directly or indirectly by use of reporter molecules.

In one embodiment, the human alveolar organoid cells described herein are used for Sars-CoV-2 infection (COVID19) related research. Studies have reported that the expression of human ACE2, which is primarily expressed on Alveolar Type 2 cells, is necessary for SARS-CoV-2 infection and disease pathogenesis. However, the structural difference between human and mouse ACE2 make mouse a poor model for SARS-CoV-2 infection. Thus, the engraftment of human alveolar organoid cells is an optimal model for COVID19-related research.

In one embodiment, the human airway organoid cells described herein are used for Sars-CoV-2 infection (COVID19) related research. Recent studies have also shown that ACE2 is expressed in some nasal and airway cells.

Immune compromised mouse strains, such as nude, Rag KO, NSG, and NRG would be necessary to prevent rejection of human cells. It is specifically contemplated herein that these mice would be optimal for generation of the COVID19 model using the organoid cells of the instant application. Mice bearing engrafted human lung epithelial cells will be infected with SARS-CoV-2 and the consequences of viral infection in vivo will be characterized.

In one embodiment, mice that are engrafted with the human alveolar or airway organoid cells described herein can be used to screen for therapeutics useful in treating a Sars-CoV-2 infection (COVID19).

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate differentiation, modulate cell morphology, or a combination thereof. In some instances, a biological activity can refer to the ability of a test compound to produce a toxic effect in a biological sample or can determine the toxic dose at which 50% of subjects are killed (i.e., TD50).

As discussed above, the alveolar organoids, airway organoids or cells thereof can be derived from a lineage which is phenotypic and/or genotypic of a disease (e.g., a lung disease). Alternatively, the alveolar organoids, airway organoids or cells thereof can be derived from a lineage which is phenotypic and/or genotypic of an organ and/or tissue or a part thereof (e.g., lung).

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and commercially available. These small molecule libraries can be screened using the screening methods described herein. A chemical library or compound library is a collection of stored chemicals that can be used in conjunction with the methods described herein to screen candidate agents for a particular effect. A chemical library comprises information regarding the chemical structure, purity, quantity, and physiochemical characteristics of each compound. Compound libraries can be obtained commercially, for example, from Enzo Life Sciences™, Aurora Fine Chemicals™, Exclusive Chemistry Ltd.™, ChemDiv, ChemBridge™, TimTec Inc.™, AsisChem™, and Princeton Biomolecular Research™, among others.

Without limitation, the compounds can be tested at any concentration that are predicted to or can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen, the size of which is only limited by the speed of generation of alveolar organoids or cells thereof. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Kits

Another aspect of the technology described herein relates to kits for treating a lung disease or disorder, kits for screening a candidate agent and/or kits for generating alveolar organoids, airway organoids or cells thereof. Described herein are kit components that can be included in one or more of the kits described herein.

In one embodiment, the kits described herein can include alveolar organoids, airway organoids or cells thereof, as that term is used herein. In one embodiment, one or more signaling pathway agonists or antagonists that promote differentiation of a stem cell or iPSC to a lung stem cell and ultimately to an alveolar organoid are included in the kit. In another embodiment, a component described herein such as one or more TGF-β receptor inhibitor(s), one or more BMP agonists, one or more FGF agonists, and instructions for converting a stem cell (e.g., embryonic stem cell, isolated pluripotent stem cell, anterior foregut endoderm cell, or definitive endoderm cell) to a human lung progenitor cell is provided. In some embodiments, reagents for selecting cells based on their expression of CD31, CD45, Epcam and Sca1 (e.g., antibodies) are provided in the kit.

Another aspect of the technology disclosed herein relates to kits to alveolar organoids, airway organoids or cells thereof according to the methods as disclosed herein. In some embodiments, the components described herein can be provided singularly or in any combination as a kit. Such kits can optionally include one or more agents that permit the detection of alveolar cell markers, airway cell markers or a lung cell marker or set thereof (e.g., antibodies to detect airway markers such as acetylated alpha tubulin or surfactant protein C). In addition, the kit optionally comprises informational material.

In some embodiments, the alveolar organoids, airway organoids or cells thereof or reagents for generating alveolar organoids, airway organoids or cells thereof in the kit can be provided in a watertight or gas tight container, which in some embodiments is substantially free of other components of the kit. For example, an appropriate medium for generating alveolar organoids, airway organoids or cells thereof can be supplied in more than one container, e.g., it can be supplied in a container having sufficient reagent for a predetermined number of screening assays, e.g., 1, 2, 3 or greater. One or more cells or reagents as described herein can be provided in any form, e.g., liquid, dried or lyophilized form. It is preferred that the cells or reagents described herein are substantially pure and/or sterile. When the one or more cells or reagents described herein is provided in a liquid solution, the liquid solution preferably is an aqueous solution, with a sterile aqueous solution being preferred. When the cells or reagents described herein is provided as a dried form, reconstitution generally is by the addition of a suitable solvent. The solvent, e.g., sterile water or buffer, can optionally be provided in the kit. Given the complexity of an alveolar organoid or airway organoid, it is preferred that such organoids are supplied in a 3D culture system comprising an appropriate medium and/or substrate for maintaining cell viability. Such kits will need to be transported in a time-sensitive and temperature-sensitive manner.

The informational material provided in the kit can be descriptive, instructional, marketing or other material that relates to the methods described herein and/or the use of a compound(s) described herein for the methods described herein. The informational material of the kits is not limited in its form. In one embodiment, the informational material can include information about the cells or reagents, concentration, date of expiration, batch or production site information, and so forth. In one embodiment, the informational material relates to methods for using or administering the compound.

In one embodiment, the informational material can include instructions to administer alveolar organoids, airway organoids or cells thereof as described herein in a suitable manner to effect treatment of a lung injury or a lung disease or disorder., e.g., in a suitable dose, dosage form, or mode of administration (e.g., a dose, dosage form, or mode of administration described herein). In another embodiment, the informational material can include instructions for differentiating a given cell to alveolar organoids, airway organoids or cells thereof. Alternatively, the informational material can include instructions for screening a candidate agent for treating a lung disease or disorder.

In addition to a compound(s) described herein, the composition of the kit can include other ingredients, such as a solvent or buffer, a stabilizer, a preservative, and/or an additional agent, e.g., for differentiating stem cells (e.g., in vitro) or for treating a condition or disorder described herein. Alternatively, the other ingredients can be included in the kit, but in different compositions or containers than a cell or reagent described herein. In such embodiments, the kit can include instructions for admixing, for example, a cell with a reagent described herein and the other ingredients, or for using a compound(s) described herein together with the other ingredients, e.g., instructions on combining the two agents prior to use or administration.

The kit can include a component for the detection of a marker for alveolar organoids or cells thereof, ES cells, iPSC cells, thyroid lineage cells, neuronal lineage cells etc. In addition, the kit can include one or more antibodies that bind a cell marker, or primers for an RT-PCR or PCR reaction, e.g., a semi-quantitative or quantitative RT-PCR or PCR reaction. Such components can be used to assess the activation of lung cell-specific markers or the loss of ES cell, iPSC, thyroid lineage, or neuronal lineage markers. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit can also include one or more reagents for enhancing the efficiency of induced pluripotent stem cell production, such as an HDAC inhibitor (e.g., valproic acid) or a DNA methyltransferase inhibitor (e.g., 5azaC).

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

The present invention may be as defined in any one of the following numbered paragraphs:

1. A method for treating a lung disease or disorder, or a lung injury in a subject, the method comprising administering to a subject, intratracheally, a composition comprising an alveolar organoid, airway organoid, or an isolated cell thereof,
    optionally, wherein the alveolar organoid or airway organoid are produced in vitro or ex vivo from a lung cell by culturing the lung cell in a 3-dimensional culture for a time and under conditions sufficient to produce an alveolar organoid or airway organoid, and
    wherein the alveolar organoid, airway organoid or cell thereof functionally engrafts into the lung, thereby treating the lung disease or disorder or lung injury in the subject.
2. A method for treating a lung disease or disorder, or a lung injury, the method comprising administering to a subject, intratracheally, a composition comprising an alveolar organoid, airway organoid, or an isolated cell thereof,
    wherein the alveolar organoid or cell thereof is CD31/CD45−, Epcam+ and Sca1− in murine cells, or CD31−/CD45, Epcam+, and HTII-280+ in human cells),
    wherein the airway organoid or cell thereof is CD31/CD45−, Epcam+ and Sca1+ in murine cells, or CD31−/CD45−, Epcam+, and NGFR+ in human cells, and
    wherein the alveolar organoid, airway organoid or cell thereof functionally engrafts into the lung, thereby treating the lung disease or disorder or lung injury in the subject.
3. The method of paragraph 1 or 2, wherein the alveolar organoid, airway organoid or cell thereof are autologous to the subject to be treated.
4. The method of paragraph 1 or 2, wherein the alveolar organoid, airway organoid or cell thereof are heterologous to the subject to be treated.
5. The method of paragraph 1 or 2, wherein the alveolar organoid or airway organoid further comprises a lung epithelial cell, or a stromal cell.
6. The method of paragraph 1, wherein the lung cell is isolated from a donor or is derived in vitro from a stem cell.
7. The method of paragraph 6, wherein the stem cell is an induced pluripotent stem cell (iPSC), an embryonic stem cell, or a lung progenitor cell.
5. The method of paragraph 1, wherein the lung cell is isolated from the donor using fluorescence-activated cell sorting (FACS).
6. The method of paragraph 1 or 2, wherein the alveolar organoid or airway organoid is a human primary alveolar (hPAL) cell-derived organoid, a human iPSC-derived organoid or a human primary airway (hPAR) cell-derived organoid.

7. The method of paragraph 1, wherein the lung cell is CD31/CD45− and Epcam+.
8. The method of paragraph 7, wherein the lung cell is Sca1+ and wherein the airway organoid derived from the lung cell is Sca1+.
9. The method of paragraph 7, wherein the lung cell is Sca1− and wherein the airway organoid derived from the lung cell is Sca1−.
10. The method of paragraph 2 or 8, wherein the Sca1+ organoids engraft and populate in the alveolar space.
11. The method of paragraph 2 or 9, wherein the Sca1− organoids engraft into regions of the lung having damaged alveolar cells.
12. The method of paragraph 2 or 11, wherein the cells of the Sca1− organoids upon engraftment are transcriptionally similar to the corresponding endogenous cells.
13. The method of paragraph 12, wherein the engrafted cells are Keratin 8+.
14. The method of paragraph 10, wherein the engrafted cells are Keratin 8+ and/or Keratin 17+.
15. The method of paragraph 1 or 2, wherein the transplanted or engrafted cells retain progenitor function as assessed by (i) their ability to give rise to organoids when returned to in vitro culture and/or (ii) their ability to respond to a second lung injury.
16. The method of any of paragraphs 1-15, wherein the subject is immunocompromised.
17. The method of any of paragraphs 1-16, further comprising, prior to transplanting, the step of diagnosing a subject as having a lung disease or disorder.
18. The method of any of paragraphs 1-17, further comprising, prior to transplanting, receiving the results of an assay that diagnoses a subject as having a lung disease or disorder.
19. The method of any of paragraphs 1-18, further comprising, prior to transplanting, the step of diagnosing a subject as being immunocompromised.
20. The method of any of paragraphs 1-19, further comprising, prior to transplanting, receiving the results of an assay that diagnoses a subject as being immunocompromised.
21. A mouse useful for modelling COVID-19 induced lung injury, comprising a recipient mouse having engrafted human primary lung cells or iPS-derived lung cells,
   wherein the mouse is made by the process of administering, intratracheally, an airway organoid, or an isolated cell thereof into the recipient mouse,
   wherein the airway organoid or cell thereof is CD31/CD45−, Epcam+ and Sca1+, and
   wherein the airway organoid or cell thereof functionally engrafts into the lung.
22. The mouse of paragraph 21, wherein the engrafted cells express CD298.
23. The mouse of paragraph 21, wherein the transplanted or engrafted cells retain progenitor function as assessed by (i) their ability to give rise to organoids when returned to in vitro culture and/or (ii) their ability to respond to a second lung injury.
24. The mouse of paragraph 23, wherein the mouse (i) is immune compromised, and/or (ii) comprises at least two different human lung cells.
25. A method of screening an agent for treatment of COVID-19, the method comprising:
   (i) contacting the mouse of paragraph 21 with an effective amount of SARS-CoV-2 to induce a lung injury,
   (ii) administering a candidate agent to the infected mouse of step (i),
   (iii) and identifying an agent capable of treating COVID-19 when the degree of lung injury is reduced in the presence of the agent as compared to a reference control.
26. The method of paragraph 25, wherein the reference control is the degree of lung injury prior to administration of the candidate agent.
27. The method of paragraph 25, wherein the reference control is the degree of lung injury in a substantially in a mouse of paragraph 21 that is not contacted with the SARS-CoV-2.
28. The method of paragraph 25, wherein the SARS-CoV-2 is administered by inhalation.
29. A transplant composition comprising a human alveolar organoid, wherein the cells of the alveolar organoid are CD31/CD45−, Epcam+ and Sca1−.
30. A transplant composition comprising a human airway organoid, wherein the cells of the airway organoid are CD31/CD45−, Epcam+ and Sca1+.
31. The transplant composition of paragraph 29, wherein the human airway organoid is an alveolar organoid, a bronchiolar organoid or a bronchoalveolar organoid.
32. A method of treating a lung disease or disorder in a subject, the method comprising:
   a. obtaining an iPSC and differentiating the iPSC to a lung cell;
   b. culturing the lung cell of step (a) in a Basic 3D medium for a sufficient amount of time to allow the lung cell to differentiate into alveolar organoids; and
   c. transplanting the alveolar organoid or an isolated cell population thereof of step (c) via intratracheal delivery in a subject in need thereof,
   wherein transplanting results in engraftment of the alveolar organoid or isolated cell population thereof
33. A method of treating a lung disease or disorder in a subject, the method comprising:
   a. obtaining an iPSC and differentiating the iPSC to an alveolar cell; and
   b. transplanting the alveolar cell or population thereof of step (a) via intratracheal delivery in a subject in need thereof,
   wherein transplanting results in engraftment of the alveolar cell.
34. The method of paragraph 32, further comprising, prior to step (b), the step of genetically modifying the lung cell.
35. The method of paragraphs 33, further comprising, prior to step (b), the step of genetically modifying the alveolar cell.
36. The method of paragraphs 1, 2, 32 or 33, further comprising administering an immunosuppressive agent prior to, or substantially at the same time as the transplantation.
37. The method of paragraphs 32 or 33, wherein the subject is immunocompromised.
38. A method of producing alveolar/airway organoids from a lung cell, comprising culturing a population of lung cells in a Basic 3D medium for a sufficient amount of time to allow the lung cells to differentiate into organoids comprising alveolar and airway cells.
39. The method of paragraph 38, wherein the population of lung cells comprises alveolar cells and bronchiole cells.
40. The method of paragraphs 38 or 39, wherein a lung cell of the population of lungs cell is differentiated from induced pluripotent stem cells or embryonic stem cells.
41. The method of any one of paragraphs 38-40, wherein the population of lung cells are co-cultured with a second population of lung cells.

42. The method of paragraph 41, wherein the second population of lung cells comprises a cell type selected from the group consisting of: stromal cell, epithelial cell, smooth muscle cell, ciliated cell, and goblet cell.

43. The method of paragraphs 41 or 42, wherein the second population of cells is a substantially pure population.

44. The method of any one of paragraphs 41-43, wherein the lung cells and the second population of cells are co-cultured on an air/liquid interface.

45. The method of any one of paragraphs 38-44, wherein the lung cells and the second population of cells are co-cultured in a gelatinous protein mixture.

46. The method of any one of paragraphs 38-45, wherein the Basic 3D medium comprises: DMEM, insulin-transferrin-selenium (ITS), fetal bovine serum (FBS), at least one antibiotic, HEPES, and/or L-glutamine.

47. The method of any one of paragraphs 38-46, wherein the at least one antibiotic is penicillin or streptomycin.

48. The method of any one of paragraphs 38-47, wherein the iPSCs are derived from a subject with a pulmonary disease or disorder.

49. The method of paragraph 48, wherein the disease or disorder is selected from the group consisting of: Surfactant protein deficiency, Hermansky-Pudlak syndrome, Idiopathic Pulmonary fibrosis, Pulmonary fibrosis, Chronic obstructive pulmonary disease (COPD), Emphysema, Chronic bronchitis, Pneumonia, Asthma, Sarcoidosis, Pleural effusion, Pleurisy; Bronchiectasis, Lymphangioleiomyomatosis (LAM), Cystic fibrosis, Interstitial lung disease, Lung cancer, Tuberculosis, Acute respiratory distress syndrome (ARDS), Infant respiratory distress syndrome (IRDS), Coccidioidomycosis, Histoplasmosis, Hypersensitivity pneumonitis (allergic alveolitis), Influenza (flu), Mesothelioma, Pertussis (whooping cough), Pulmonary hypertension, Pulmonary embolism, Pulmonary edema, Pulmonary alveolar proteinosis, Pulmonary contusion, Pulmonary alveolar microlithiasis, Severe acute respiratory syndrome (SARS), and Pneumothorax, bronchopulmonary dysplasia, pneumoconiosis, alpha-1 antitrypsin deficiency, asbestosis, bronchiolitis, byssinosis, cryptogenic organizing pneumonia, and primary ciliary dyskinesia.

50. The method of any of paragraphs 38-49, wherein the lung cell is differentiated from an iPSC or ESC, and is genetically modified.

51. The method of any of paragraphs 38-50, wherein the lung cell is differentiated from an iPSC or ESC derived from a subject having a lung disease or disorder, and is genetically modified.

52. A method of isolating alveolar and airways cells from an alveolar/airway organoid of any of paragraphs 34-47, the method comprising:
  a. contacting an alveolar/airway organoid of any of paragraphs 34-47 with dispase for a sufficient amount of time to allow for the gelatinous protein mixture to dissolve;
  b. centrifuging the material of step (a) to isolate the alveolar/airway organoid from supernatant;
  c. contacting the isolated alveolar/airway organoid from step (b) with trypsin for a sufficient amount of time to isolate the alveolar and airway cells from the second population of lung cells; and
  d. resuspending the alveolar and airway cells of step (c) in a suitable buffer.

53. A composition comprising an organoid made by the method of any one of paragraphs 38-51 or a population of isolated alveolar and airway cells produced by the method of paragraph 52.

54. The composition of paragraph 53, further comprising a pharmaceutically acceptable carrier.

55. The composition of paragraph 53, wherein the population is a substantially pure population.

56. A method of treating a lung disease or disorder, the method comprising transplanting the alveolar/airway organoid made by the method of any of paragraphs 38-51, the isolated alveolar and airway cell made by the method of paragraph 52 or a population thereof, or the composition of any of paragraphs 53-55 to a subject in need thereof.

57. The method of paragraph 56, wherein transplanting is performed via intratracheal delivery.

58. The method of paragraphs 56 or 57, wherein transplanting results in engraftment of the airway cells of the alveolar/airway organoid, the isolated alveolar and airway cells population, or the composition.

59. The method of paragraph 56, wherein engraftment of airway cells occurs in the trachea, lung parenchyma, bronchioles, respiratory bronchioles, alveolar ducts, alveolar sacs, alveoli, pulmonary acinus, pulmonary lobule, lower respiratory tract, upper respiratory tract, left lung, and/or right lung.

60. The method of any of paragraphs 56-59, further comprising, prior to transplanting, the step of diagnosing a subject as having a lung disease or disorder.

61. The method of any of paragraphs 56-60, further comprising, prior to transplanting, receiving the results of an assay that diagnoses a subject as having a lung disease or disorder.

62. A method of treating a lung disease or disorder in a subject, the method comprising:
  a. obtaining a iPSC and differentiating the iPSC to a lung cell;
  b. culturing the lung cell of step (a) in a Basic 3D medium for a sufficient amount of time to allow the lung cells to differentiate into alveolar/airway organoids comprising alveolar and airway cells; and
  c. transplanting the alveolar and airway organoid or an isolated cell population thereof of step (c) via intratracheal delivery in a subject in need thereof,
  wherein transplanting results in engraftment of the airway cells.

63. The method of paragraph 62, further comprising, prior to step (b), the step of genetically modifying the lung cell.

64. The method of any of paragraphs 62-63, further comprising administering at least one immunosuppressive therapeutic.

65. The method of any of paragraphs 1, 2, 32, 33, or 56-64, further comprising administering at least one additional therapeutic for treatment of the lung disease or disorder.

66. A method of increasing the efficiency of engraftment of an alveolar cell following an alveolar cell transplant, the method comprising co-administering an immunosuppressant agent with the transplantation.

67. The method of paragraph 66, wherein the immunosuppressant agent inhibits T cells.

68. The method of paragraph 66 or 67, wherein the immunosuppressant agent is administered prior to, during, or after the transplant.

69. The method of any of the preceding paragraphs, wherein the genetic modification is in a nucleotide modification in a disease gene.

70. The method of paragraph 69, wherein the nucleotide modification is a nucleotide deletion, nucleotide insertion, or nucleotide base substitution.
71. The method of paragraph 69 or 70, wherein the disease gene is CTFR or HSP1.
72. A method for screening a candidate agent for treating a lung disease or disorder, the method comprising (i) contacting an alveolar organoid or isolated cell thereof with a candidate agent for treating a given lung disease or disorder, and
  (ii) comparing the expression or activity of at least one disease marker that is modulated in the presence and absence of the candidate agent,
    wherein a change in the expression or activity of the at least one disease marker is indicative that the candidate agent can be used to treat the given lung disease or disorder.
73. The method of paragraph 72, wherein the alveolar organoids or cells thereof are generated using cells derived from a subject having a lung disease or disorder.
74. A method for screening a candidate agent for accelerating formation of alveolar organoids in vitro, the method comprising: contacting the population of lung cells with a candidate agent and comparing the length of time to generate an alveolar organoid in the presence and absence of the candidate agent, wherein a decrease in the length of time indicates that the candidate agent accelerates formation of alveolar organoids.
75. A method of producing alveolar organoids, the method comprising culturing a population of CD31/CD45−, Epcam+, Sca1− lung cells in a Basic 3D medium for a sufficient amount of time to allow the population of lung cells to differentiate into alveolar organoids.
76. The method of paragraph 75, wherein the population of lung cells comprises a type 1 alveolar cell, or a type II alveolar cell.
77. The method of paragraphs 75 or 76, wherein a lung cell of the population of lung cells is differentiated from induced pluripotent stem cells (iPSC) or embryonic stem cells.
78. The method of paragraph 75, wherein the population of lung cells are co-cultured with a second population of lung cells.
79. The method of paragraph 78, wherein the second population of lung cells comprises a cell type selected from the group consisting of: stromal cell, epithelial cell, smooth muscle cell, ciliated cell, and goblet cell.
80. The method of paragraphs 78 or 79, wherein the second population of cells is a substantially pure population.
81. The method of any one of paragraphs 75-80, wherein the population of lung cells and the second population of cells are co-cultured on an air/liquid interface.
82. The method of any one of paragraphs 75-81, wherein the population of lung cells and the second population of cells are co-cultured in a gelatinous protein mixture.
83. The method of any one of paragraphs 75-82, wherein the Basic 3D medium comprises: DMEM, insulin-transferrin-selenium (ITS), fetal bovine serum (FBS), at least one antibiotic, HEPES, and/or L-glutamine.
84. The method of paragraph 83, wherein the at least one antibiotic is penicillin or streptomycin.
85. The method of paragraph 77, wherein the iPSCs are derived from a subject with a pulmonary disease or disorder.
86. The method of paragraph 85, wherein the disease or disorder is selected from the group consisting of: Surfactant protein deficiency, Hermansky-Pudlak syndrome, Idiopathic Pulmonary fibrosis, Pulmonary fibrosis, Chronic obstructive pulmonary disease (COPD), Emphysema, Chronic bronchitis, Pneumonia, Asthma, Sarcoidosis, Pleural effusion, Pleurisy; Bronchiectasis, Lymphangioleiomyomatosis (LAM), Cystic fibrosis, Interstitial lung disease, Lung cancer, Tuberculosis, Acute respiratory distress syndrome (ARDS), Infant respiratory distress syndrome (IRDS), Coccidioidomycosis, Histoplasmosis, Hypersensitivity pneumonitis (allergic alveolitis), Influenza (flu), Mesothelioma, Pertussis (whooping cough), Pulmonary hypertension, Pulmonary embolism, Pulmonary edema, Pulmonary alveolar proteinosis, Pulmonary contusion, Pulmonary alveolar microlithiasis, Severe acute respiratory syndrome (SARS), and Pneumothorax, bronchopulmonary dysplasia, pneumoconiosis, alpha-1 antitrypsin deficiency, asbestosis, bronchiolitis, byssinosis, cryptogenic organizing pneumonia, and primary ciliary dyskinesia.
87. The method of any of paragraphs 75-86, wherein a lung cell of the population of lung cells is differentiated from an iPSC or ESC, and is genetically modified.
88. The method of any of paragraphs 75-87, wherein a lung cell of the population of lung cells is differentiated from an iPSC or ESC derived from a subject having a lung disease or disorder, and is genetically modified.
89. A method of isolating an alveolar cell from an alveolar organoid of any of paragraphs 75-88, the method comprising:
  a. contacting an alveolar organoid of any of paragraphs 1-14 with dispase for a sufficient amount of time to allow for the gelatinous protein mixture to dissolve;
  b. centrifuging the material of step (a) to isolate the alveolar organoid from supernatant;
  c. contacting the isolated alveolar organoid or step (b) with trypsin for a sufficient amount of time to isolate the alveolar cells from the second population of lung cells; and
  d. resuspending the alveolar cells of step (c) in a suitable buffer.
90. A composition comprising an organoid made by the method of any one of paragraphs 75-88 or a population of isolated alveolar cells made by the method of paragraph 89.
91. The composition of paragraph 90, further comprising a pharmaceutically acceptable carrier.
92. The composition of paragraph 90 or 91, wherein the population of isolated alveolar cells is a substantially pure population of isolated alveolar cells.

EXAMPLES

Example 1

Exemplary Protocol for Producing an Alveolar Organoid

Before beginning the protocol, one skilled in the art will need the following:
1) Avertin (1× stock in 4° C.)
2) Forceps, surgical scissors, pins, dissecting platform
3) Cold PBS (make a 50 mls and a 40 mls aliquot and place in on ice before getting the mice)
4) 1×10 mls syringe/experiment, 1×5 mls syringes/genotype or condition, and 3 mL syringes/mouse
5) butterfly needle/genotype or condition, 2×27 needles/mouse
6) 5 mls FBS on ice 7) Dispase (store aliquots in −20° C.; thaw in 50° C. waterbath, remove immediately once thawed and place on ice)
8) Collagenase/dispase (store at −20° C.; if provided as a powder store at −20 C, resuspend in 1 ml of sterile milliQ water)
9) DNAse (store at −20° C.; 1% solution; check unit activity of each lot number)
10) Bucket with ice
11) 100 and 40 μm filters (above bench)
12) FACs tube with strainer (7+ #of samples to be sorted)
13) LMP agarose, 1% (store at RT, at 50° C. until ready for use)

Basic 3D Medium:

| | |
|---|---|
| DMEM/F12 | 50 mL |
| ITS (insulin-transferrin-selenium) supplement | 500 uL |
| 10% FBS | 5 mL |
| 100 I.U./ml Penicillin-100 ug/ml Streptomycin | 250 uL |
| 1 mM HEPES | 50 uL |
| L-glutamine (Glutamax) | 500 uL |

The following steps are to be followed to take cells from lung tissue and prepare a single cell suspension.
1) Thaw dispase aliquot (2 mls/mouse) in the 37° C. water-bath, place on ice immediately after.
2) Place the dispase/collagenase on ice to thaw.
3) Prep the 5 mls syringe with 1 ml of 1× Avertin per mouse.
4) Use grated side of the cage to give the mice something to attach to and pressing hard down, squeeze and hold the mice between the side of the thumb and hand. Firmly hold tail with other finger. (use left hand for the mice and right for the syringe).
5) Anesthetize mouse with 1 mL Avertin 1× per average adult mouse (27.5 G needle on 5 mL syringe, IP injection), test with forceps (toe pinch) to make sure that they are sufficiently anesthetized
6) Affix mouse to dissecting platform with tape or pins and spray down mouse fur with 70% ethanol (wipe off excess with Kimwipes).
7) Open the skin on the stomach to expose the base of the sternum. Hold the base of the sternum with forceps and carefully cut up the ribcage to the neck. Cut skin from center line right and left along diaphragm edge. Fold the two sides of the rib cage open and secure with pins
8) Using a butterfly needle on a 50 mL syringe, perfuse 10-15 mL of PBS (ice cold) through right ventricle (on your left) until lungs cleared of blood. (cut a slit in left ventricle to allow blood to leave—should see lungs turn white and expand)
9) Remove heart to euthanize mouse, then cut up the neck (through collar bone) to the chin of the mouse.
10) Expose trachea, place forceps under trachea to keep exposed
11) Using a 27 G needle on a 3 mL syringe, inject 2 mL dispase (BD, undiluted liquid, aliquots in −20° C.) into trachea (go between the cartilage rings and on top of the top arm of the forceps) just until the lungs inflate into trachea—you should be able to do this with less than 2 mls.
12) Close up with 0.5 mls of LMP agarose.
13) Dissect out trachea and lungs by gently tugging on the trachea while snipping away the connective tissue; leave lungs and trachea intact and place in small Petri dish on ice. Make sure to catch the trachea between the dish and the lid.
14) Trim other tissues off lung, dissect off each lobe and move each lung into a 50 mls conical tube, place sideways on ice.
15) Use scissors to mince lung tissue into small pieces (3-4 mins per tube). For each lung sample, add 3 mL PBS.
16) Add 60 uL collagenase/dispase for every 3 mL of PBS above (from Roche, 100 mg/mL in PBS stock stored in −20° C.; store powder in cold room)
17) Add 7.5 uL DNAse per 3 mL of digest solution (from 1% stock stored in −20° C., which is 10 mg/mL, final DNAse concentration is 0.025 mg/mL).
18) rotate 45 min @37° C. (final collagenase/dispase concentration is ~2 mg/mL)
PF10 (make 40 mL by adding 4 mL FBS (4° C. below bench) to pre-cooled 40 mL PBS)
Place FBS and DMEM in the 37° C. bath in tissue culture (TC) room.
19) Place tube on ice.
20) Invert several times to mix. Leave on ice to cool for no more than 5 minutes.
21) Into a 50 mL tube, filter digested tissue through a 100 um filter, then a 40 um filter using 2 mls of cold PF10 to wash cell through tubes and filters. (try to get every last drop, cleaning the strainers against the top of the tubes)
22) Spin 5 min @1000 rpm in Beckman centrifuge at 4 degrees
23) Discard supernatant The following steps are to be followed for lysing of red blood cells.
1) Resuspend cell pellet from above in 1 mL of lysing solution (0.15 M NH4Cl, 10 mM KHCO3, 0.1 mM EDTA, in 1 L distilled H2O; filtered with 0.45 um filter and stored at RT)
2) Lyse 90 sec at RT (timer start after resuspension)
3) Add 6 mL of pre-warmed DMEM without serum (refrigerator below bench); mix
4) Add 0.5 mL of pre-warmed FBS slowly to bottom of tube by inserting pipet tip all the way through the resuspended cell solution
5) Centrifuge undisturbed layers for 5 min @1000 rpm at 4 C
6) Aspirate the supernatant; resuspend in PF10 for counting or staining (600-700 ul per adult lung/1 ml per 3 pups lungs)
7) Merge the identical sample.

The following steps are to be followed for surface staining.
1) Get stains and keep on ice:
  a. DAPI
  b. Sca-1→APC-Cy7
  c. EpCam→PE-Cy7
  d. CD31→APC
  e. CD45→APC
2) Make ≤1 ml aliquots for the samples. Mix equal amount of all the samples for making 800 ul of cells.
3) Aliquot 100 ul of cells in 7 tubes.
4) For the samples: make a master mix of all the stains needed and after mixing aliquot in the tubes. Vortex and place on ice
5) For the controls: mix 1 ul of the appropriate stains as follows:
  a. NEG4→n/a
  b. DAPI→
  c. CD31/CD45→CD31-APC+CD45-APC
  d. EpCAM→EpCAM-PE-Cy7 e. Sca-1→APC-Cy7
f. FMO (EpCAM)→DAPI+CD31−APC+CD45−APC+Sca-1 APC-Cy7
g. FMO (Sca1)→DAPI+CD31−APC+CD45−APC+EpCAM-PE-Cy7
6) Incubate at room temperature (RT) for 15 minutes in the dark
7) Quick spin till 10K rpm
8) For each tube, aspirate supernatant and resuspend in 1 ml of PF10
9) Quick spin till 10K rpm
10) Aspirate (till leaving 100 ul)

The following steps are to be followed for FACS sorting.
1) Label the proper amount of blue cap tubes with strainer (the blue cap ensures single cells suspension, only use half of the cap so that air can flow in the opposite orientation)
2) Resuspend cell with 300 ul of PF10 for the control and more for the samples
3) Pass each sample through the filter in the blue cap tubes (theoretical optimal concentration $10^6$/ml). The trick is pushing the cells through the pipette tip slowly and perpendicular to the plane of the membrane.
4) Label 2 Epp-tubes A (Sca1−) and B (Sca1+). Add 250 ul of FBS in each one of them and mix.
5) Before going to the FACS core, thaw Matrigel™ on ice (it takes 1.5 hrs)

Gating information used for indicated cell type:
Sca1− Cells (e.g., Alveolar Cell Population):
P1-P3: adjust size and single cell
P4: gate for DAPI−
P5: gate for DsRed+
P6: gate for EpCAM+ CD31−CD45−
P7: gate for EpCAM+ Sca1−
Sca1+ Cells (e.g., Alveolar and Airway Cell Mixture):
P1-P3: adjust size and single cell
P4: gate for DAPI−
P5: gate for DsRed+
P6: gate for EpCAM+ CD31−CD45−
P8: gate for EpCAM+ Sca1+

The following steps are to be followed for plating.
General lay out: Bottom of the wells: 0.5 ml of 3D media. Top of the wells. For each well: (50 ul of 3D media+$5*10^3$ Sca1+ or Sca1−)+(50 ul of MATRIGEL+$5*10^4$ stromal cells)

Sca1+ or Sca1− preparation. On the basis of sorted cells, resuspend Scar at $5*10^3$/50 ul in 3D media and Sca1− cells at $5*10^3$/50 ul in 3D media.

Stromal Cells Preparation and Plating
1) Wash cultured stromal cells (maximum P6) with PBS and trypsinize at 37° C.
2) Resuspend cells in 10 mls media (Advanced DMEM+Endothelial Cell growth supplement, Heparin, 20% FBS, Pen/Strep, Glutamine, HEPES).
3) Count cells by Hemocytometer
4) Resuspend pellet in MATRIGEL™ at $5*10^4$ per 50 ul.
5) Once decided how many wells to plate mix 50*(n+0.5) of Sca1+ or Sca1− cells with 50*(n+0.5) of stromal cells in MATRIGEL™
6) Plate 100 ul per well to the top (24 well plate, 0.4 um transwell) with no media on the bottom, being careful to completely avoid bubbles.
7) Incubate plate(s) at 37 C for 20 mins
8) Add 500 ul of pre-warmed 3D media to the bottom of each well.
9) Incubate for 14-21 days, changing media after 2-4 days and then after every other day.

Transplantation Protocol

Prior to transplanting organoid cells, 8-12 weeks old recipient mice received a single dose of Bleomycin (1.5 U/Kg in PBS) intratracheally. One day after bleomycin-induced injury, lung organoid cells were delivered to recipient mice intratracheally. Briefly, dispase was added to organoid cultures to dissolve the Matrigel™ solution for 1 hour at 37 degrees. Organoids were spun down at 1000 rpm for 5 min and supernatant was removed. The organoids were resuspended in a trypsin solution at 37 degrees to yield a single cell suspension. Trypsin was quenched with a solution of PBS+10% FBS and spun down. Organoid cells were resuspended in a solution of PBS+10% FBS before delivering intratracheally to recipient mice in a 40 uL volume.

Conditions for Mouse Transplant

For mouse epithelial organoid cells, anywhere from 0.1-1 million Sca1− or Sca1+ cells were delivered. Data presented herein indicate that mouse cells engraft when delivered in these cell number ranges. For all cell numbers and conditions, the cells were delivered in 40 microliter volumes in a solution of PF10 (PBS+10% FBS). Supporting cells were delivered along with epithelial organoid cells. The cells were initially plated at 5000 epithelial cells with 50,000 supporting cells. After culturing, and at the time of transplantation, the ratio of epithelial cells to supporting cells was magnitudes higher than when plated. Engraftment of cells were detected as early as 2 weeks following engraftment. Further, cells were found to be retained for at least 17 weeks following engraftment.

Both iPSC-derived alveolar and airway organoids were transplanted without supporting cells. For alveolar cells, 0.1-0.8 million cells were delivered in 40 microliter volume of PF10. These cells can be detected at 7 weeks following engraftment. For airway cells, 0.04-0.1 million cells were delivered in 50 microliter volume of airway media. These cells can be detected at 4 weeks following engraftment.

Primary alveolar organoid cells were transplanted at 0.03-0.1 million cells with supporting human fibroblast cells (MRC5) in 40 microliter volume of PF10. The cells are initially plated at 5000 epithelial cells with 50,000 supporting cells. After culturing and at the time of transplantation, the ratio of epithelial cells to supporting cells was magnitudes higher than when plated. These cells can be detected at 2 weeks following engraftment.

Primary airway organoid cells were transplanted without supporting cells. 0.06 million cells were delivered in 50 microliter volume of PF10. These cells can be detected at 12 weeks following engraftment.

Example 2

Screening Assays

To help facilitate the study of early-stage LUADC, a tumor organoid culture system was established using in vitro induced primary lung epithelial cell. This system was characterized using bulk-RNA-Sequencing, single cell RNA-Sequencing, immunofluorescence stainings, and transplantation assays. These in vitro induced $KRAS^{G12D}$ organoids recapitulate transcriptional changes observed in autochthonous KRAS driven LUADC. Hence, this new organoid system provides an in vitro tool to rapidly and accurately model lung tumor progression. The effect of different genetic alterations, such as EGFR, $KRAS^{G12C}$, or other known oncogenic LUADC drivers or tumor suppressors can be rapidly tested using different cells of origin. Furthermore, the organoid system can be used to screen for drugs that target mechanisms specific for progressing tumor cells. Additionally, this system can be used to study the effect of different cell types used for co-culture and identify secreted factors that promote or inhibit tumor organoid progression.

Mouse Cohorts

Kras$^{LSL-G12D/+}$ (Jackson et al., 2001) and Kras$^{LSL-G12D/+}$; p53$^{fl/fl}$ (Jackson et al., 2005) mice were crossed to Rosa26-eYFP mice to obtain Kras$^{LSL-G12D/+}$; Rosa26$^{LSL-YFP}$ (KY) and Kras$^{LSL-G12D/+}$; p53$^{fl/fl}$; Rosa26$^{LSL-YFP}$ (KPY) mice. Rosa26$^{LSL-YFP}$ (Y) control mice were littermates of the KY mice. Mice were maintained in virus-free conditions. All mouse experiments were approved by the BCH Animal Care and Use Committee, accredited by AAALAC, and were performed in accordance with relevant institutional and national guidelines and regulations.

In Vivo Adenovirus Infection 8 week old mice were infected with 2.5×10$^7$ PFU adenovirus by intratracheal instillation as described previously (DuPage et al., 2009). A 1:1 ratio of male and female mice was used.

Murine Lung Preparation and Fluorescence Activated Cell Sorting (FACS)

Mice were anesthetized with avertin, perfused with 10 ml PBS, followed by intratracheal instillation of 2 ml dispase (Corning). Lungs were iced, minced and incubated in 0.0025% DNAse (Sigma Aldrich) and 100 mg/ml collagenase/dispase (Roche) in PBS for 45 min at 37° C., filtered through 100 μm and 40 μm cell strainers (Fisher Scientific), and centrifuged at 1000 rpm, 5 min at 4° C. Cells were resuspended in red blood cell lysis buffer (0.15 M NH4Cl, 10 mM KHCO3, 0.1 mM EDTA) for 1.5 min, washed with advanced DMEM (Gibco), and resuspended in PBS/10% FBS (PF10) at 1 million/100 μl. Depending on the experiment, cells were incubated for 10 min on ice with DAPI as a viability dye and the following antibodies: anti-CD31 APC, anti-CD45 APC, anti-Ly-6A/E (SCA1) APC/Cy7 (all Thermo Fisher Scientific), anti-CD326 (EP-CAM) PE/Cy7 (Biolegend) (all 1:100). Single stain controls and fluorophore minus one (FMO) controls were included for each experiment. FACS was performed on a FACSAria II and analysis was done with FlowJo.

In Vitro Adenovirus Infection and Organoid Culture

Murine lung CD31$^-$ CD45$^-$ EPCAM$^+$ SCA1$^-$ cells isolated by FACS as described in section "Murine lung preparation and fluorescence activated cell sorting (FACS)" were split into 2 or 3 equal aliquots, or not split, depending on the experiment, pelleted by pulse spin and resuspended in 100 μl MTEC/Plus media (Zhang et al., 2017) containing 6×10$^7$ PFU/ml of Ad5CMV-Cre, Ad5CMV-Empty, or no virus in 100 μl per 100,000 cells. The cells were incubated for 1 h at 37° C., 5% CO$_2$ in 1.5 ml tubes. Cells were then pelleted by pulse spin and resuspended in 1× phosphate-buffered saline (PBS). This step was repeated twice for a total of three washing steps. Cells were resuspended in Dulbecco's Modified Eagle's Medium/F12 (Invitrogen) supplemented with 10% FBS, penicillin/streptomycin, 1 mM HEPES, and insulin/transferrin/selenium (Corning) (3D media) at a concentration of 5,000 live cells (trypan blue negative) per 50 μl. As supporting cells, a mix of neonatal mesenchymal cells was isolated as described elsewhere (Lee et al., 2014). The mesenchymal cells were pelleted and resuspended in growth factor reduced (GFR) Matrigel™ at a concentration of 50,000 cells per 50 μl. Equal volumes of cells in 3D media and supporting cells in GFR Matrigel™ were mixed and 100 μl were pipetted into a Transwell (Corning). Plates were incubated for 20 min at 37° C., 5% CO$_2$ until Matrigel™ solidified. Finally, 500 μl of 3D media was added to the bottom of the well. 3D media was changed every other day.

Stainings and Immunofluorescence (IF) on Organoid Cultures

Organoid cultures were fixed with 10% neutral-buffered formalin overnight at room temperature. After rinsing with 70% ethanol, the organoid cultures containing Matrigel plug was immobilized with Histogel™ (Thermo Scientific) for paraffin embedding. Paraffin blocks were cut into 5 μm sections and adhered to glass slides. For deparaffinization, slides were incubated in xylene and then rehydrated in 100%, 95%, 70% ethanol successively. Slides were then stained with haematoxylin and eosin, or further processed for immunofluorescence (IF) stainings. For IF stainings, antigen was retrieved by incubating the slides in citric acid buffer (pH 6) at 95° C. for 20 min. After washing slides with PBS containing 0.2% Triton-X (PBS-T) and blocking with 10% normal donkey serum for 1 h at room temperature, slides were incubated with antibodies for Ki67 (EBioscience 1:100), YFP (Abcam, 1:400), SPC (Abcam, 1:1,000), Nkx2-1 (Abcam, 1:250) Hmga2 (GeneTex, 1:200), in a humidified chamber at 4° C. overnight. Secondary antibodies were added following three washing steps with PBS-T and included donkey anti-rat Alexa 594, donkey anti-goat Alexa 488/647, donkey anti-rabbit Alexa 488/594, donkey anti-mouse Alexa 647 (all Invitrogen, 1:200). Slides were mounted using Prolong Gold with DAPI (Invitrogen).

Preparing Single Cell Suspensions of Organoid Cultures and Passaging of Organoids At day 7 of organoid culture, 100 μl dispase (Fisher Scientific) was added to the transwells on top of the Matrigel and incubated for 1 h at 37° C., 5% CO$_2$. After digestion of the Matrigel, the wells were washed with PBS and the organoids were pipetted into 15 ml canonical tubes. The tubes were filled with PBS to dilute the remaining Matrigel™ and dispase. After pelleting the organoids at 300 g for 5 min, the organoids were resuspended in 37° C. warm Trypsin EDTA (0.25%, Invitrogen) and incubated for 7-10 min at room temperature to obtain a single cell suspension. Trypsin was quenched by adding PBS+10% FBS (PF10). To passage cells, cells were mixed with fresh mesenchymal cells as described in "In vitro adenovirus infection and organoid culture" and plated into new transwells.

It is specifically contemplated that the incubation period will depend on the organoid species. For example, a mouse organoid is cultured for 21 days, whereas a human organoid is cultured for 7-14 days.

Transplantation Assays

To ensure engraftment, 8-10 weeks old Athymic Nude mice were injured by injecting 1.5 U/kg bleomycin intratracheally one day before transplantation. For transplantation assays, single cell suspensions were obtained from day 14-21 of passage 0 and passage 1 organoid cultures as described in section "Preparing single cell suspensions of organoid cultures and passaging of organoids". To ensure transplantation of equal numbers of Cre-activated cells across samples, YFP$^+$ cells were counted under the fluorescence microscope and 11,000-65,000 YFP$^+$ cells resuspended in 45 μl PBS were administered into the lungs of the injured Athymic Nude intratracheally. For histology evaluation, mice were sacrificed after 4 weeks and lungs were fixed by injecting 10% neutral-buffered formalin into the lungs through the trachea.

FACS to Prepare Organoid Cultures for scRNA-Seq

Single cell suspensions were obtained from day 7 organoid cultures as described in section "Preparing single cell suspensions of organoid cultures". For FACS staining, cells were incubated with EPCAM-PeCy7 (BioLegend) and DAPI (Sigma-Aldrich) for 10 min on ice. A DAPI only control served as the fluorophore minus one (FMO) control for EPCAM. FACS was performed on a FACSAria II and analysis was done with FlowJo.

RNA Extraction, RNA-Sequencing and Bioinformatic Analysis

EPCAM$^+$ cells were obtained from organoid cultures as described in section "FACS to prepare organoid cultures for scRNA-Seq". RNA was extracted using the Absolutely RNA Microprep Kit (Agilent). After RNA extraction, all downstream quality control steps, library preparation, sequencing, and differential gene expression analysis was performed by the Molecular Biology Core Facilities at Dana-Farber Cancer Institute. Complementary DNA (cDNA) was synthesized with Clontech SmartSeq v4 reagents from 2 ng of RNA. Full length cDNA was fragmented to a mean size of 150 bp with a Covaris M220 ultrasonicator and Illumina libraries were prepared from 2 ng of sheared cDNA using Takara Thruplex DNAseq reagents according to manufacturer's protocol. The finished double strand DNA libraries were quantified by Qubit fluorometer, Agilent Tape Station 2200, and RT-qPCR using the Kapa Biosystems library quantification kit. Uniquely indexed libraries were pooled in equimolar ratios and sequenced on an Illumina NextSeq500 run with single-end 75 bp reads at the Dana-Farber Cancer Institute Molecular Biology Core Facilities. Sequenced reads were aligned to the UCSC hg19 reference genome assembly and gene counts were quantified using STAR (v2.5.1b) (Dobin et al., 2013). Differential gene expression testing was performed by DESeq2 (v1.10.1) (Love et al., 2014) and normalized read counts (FPKM) were calculated using cufflinks (v2.2.1) (Trapnell et al., 2010). RNAseq analysis was performed using the VIPER snakemake pipeline (Cornwell et al., 2018).

Statistics

Statistical testing was performed using GraphPad Prism. The tests used to determine statistical significance are quoted in the appropriate figure legends. P-values are indicated in the figures, and P-values <0.05 were considered significant.

Single Cell RNA-Seq

Single cell RNA-Seq was performed using the 10× Genomics platform (10× Genomics, Pleasanton, CA). FACS sorted cells from either mice or organoid cultures were encapsulated with a 10× Genomics Chromium Controller Instrument using the Chromium™ Single Cell A Chip Kit. Encapsulation, reverse transcription, cDNA amplification, and library preparation reagents are from the Chrormium™ Single Cell 3' Library & Gel Bead Kit v3. Briefly, single cells were resuspended in PHO at a concentration of 1000 cells $\mu l^{-1}$. Protocol was performed as per 10× Genomics protocols without modification (https://support.10xgenomics.com/single-cell-gene-expression/library-prep/doc/user-guide-chromium-single-cell-3-reagent-kits-user-guide-v2-chemistry). Libraries were sequenced using an Illumina NextSeq500 using paired-end sequencing with single indexing (Read 1=26 cycles, index (i7)=8 cycles, and Read 2=98 cycles). Reads were aligned to the mm10 reference genome and count matrices were generated using CellRanger3.0.0 (10× Genomics). Total cDNA and cDNA quality following amplification and clean-up was determined using a Qubit™ dsDNA HS assay kit and the Agilent TapeStation High Sensitivity D5000 ScreenTape System. Library quality pre-sequencing was determined using Agilent TapeStation and QPCR prior to sequencing. TapeStation analysis and library QPCR was performed by the Biopolymers Facility at Harvard Medical School.

Computational Analysis

Count matrices generated by CellRanger3.0.0 were read into the Python single cell analysis environment Scanpy (Wolf et al., 2018). In brief, cells with >10% mitochondrial content, which correlated with low read count, were removed. The data was normalized, logarithmized, and Markov Affinity-based Graph Imputation applied with the following settings (Gene to return=all, k=5, t=15, n_pca=20) (Van Dijk et al., 2018). Annotated Jupyter notebooks containing the computational analysis to reproduce the in vivo and organoid single cell RNA-Seq data, including RNA velocity analysis, can be found on GitHub (https://github.com/alm8517/Kras_invivo_organoid). Gene Ontology enrichment analysis was performed with Enrichr (Kuleshov et al., 2016) using the GSEAPY python wrapper. A reference list of murine transcription factors and transcription cofactors is from the Animal Transcription Factor Database (Hu et al., 2019). Lists of genes activated by specific transcription factors were from the TRRUST database (Han et al., 2018). KRAS activation signature was previously described (Barbie et al., 2009; Bild et al., 2006). Murine AT2 marker genes are from PanglaoDB (Franzén et al., 2019). Data was visualized using either in-built Scanpy plotting functions or Seaborn (https://seaborn.pvdata.org/). Mann-Whitney U tests were performed using Scipy 1.3.0 statistical functions (scipy.stats).

REFERENCES

Barbie, D. A., Tamayo, P., Boehm, J. S., Kim, S. Y., Moody, S. E., Dunn, I. F., Schinzel, A. C., Sandy, P., Meylan, E., Scholl, C., et al. (2009). Systematic RNA interference reveals that oncogenic KRAS-driven cancers require TBK1. Nature 462, 108-112.

Bild, A. H., Yao, G., Chang, J. T., Wang, Q., Potti, A., Chasse, D., Joshi, M. B., Harpole, D., Lancaster, J. M., Berchuck, A., et al. (2006). Oncogenic pathway signatures in human cancers as a guide to targeted therapies. Nature 439, 353-357.

Cornwell, M. I., Vangala, M., Taing, L., Herbert, Z., Köster, J., Li, B., Sun, H., Li, T., Zhang, J., Qiu, X., et al. (2018). VIPER: Visualization Pipeline for RNA-seq, a Snakemake workflow for efficient and complete RNA-seq analysis. BMC Bioinformatics 19.

Van Dijk, D., Sharma, R., Nainys, J., Wolf, G., Krishnaswamy, S., Pe'er Correspondence, D., and Gene, G. A. (2018). Recovering Gene Interactions from Single-Cell Data Using Data Diffusion In Brief Population Analysis Archetypal Analysis Gene Interactions.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

DuPage, M., Dooley, A. L., and Jacks, T. (2009). Conditional mouse lung cancer models using adenoviral or lentiviral delivery of Cre recombinase. Nat. Protoc. 4, 1064-1072.

Franzén, O., Gan, L.-M., and Björkegren, J. L. M. (2019). PanglaoDB: a web server for exploration of mouse and human single-cell RNA sequencing data. Database 2019.

Han, H., Cho, J. W., Lee, S., Yun, A., Kim, H., Bae, D., Yang, S., Kim, C. Y., Lee, M., Kim, E., et al. (2018).

TRRUST v2: An expanded reference database of human and mouse transcriptional regulatory interactions. Nucleic Acids Res. 46, D380-D386.

Hu, H., Miao, Y.-R., Jia, L.-H., Yu, Q.-Y., Zhang, Q., and Guo, A.-Y. (2019). AnimalTFDB 3.0: a comprehensive resource for annotation and prediction of animal transcription factors. Nucleic Acids Res. 47, D33-D38.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes Dev. 15, 3243-3248.

Jackson, E. L., Olive, K. P., Tuveson, D. A., Bronson, R., Crowley, D., Brown, M., and Jacks, T. (2005). The differential effects of mutant p53 alleles on advanced murine lung cancer. Cancer Res. 65, 10280-10288.

Kuleshov, M. V., Jones, M. R., Rouillard, A. D., Fernandez, N. F., Duan, Q., Wang, Z., Koplev, S., Jenkins, S. L., Jagodnik, K. M., Lachmann, A., et al. (2016). Enrichr: a comprehensive gene set enrichment analysis web server 2016 update. Nucleic Acids Res. 44, W90-W97.

Lee, J.-H., Bhang, D. H., Beede, A., Huang, T. L., Stripp, B. R. R., Bloch, K. D. D., Wagers, A. J. J., Tseng, Y.-H., Ryeom, S., Kim, C. F. F., et al. (2014). Lung Stem Cell Differentiation in Mice Directed by Endothelial Cells via a BMP4-NFATc1-Thrombospondin-1 Axis. Cell 156, 440-455.

Love, M. I., Huber, W., and Anders, S. (2014). Moderated estimation of fold change and dispersion for RNA-seq data with DESeq2. Genome Biol. 15, 550.

Trapnell, C., Williams, B. A., Pertea, G., Mortazavi, A., Kwan, G., Van Baren, M. J., Salzberg, S. L., Wold, B. J., and Pachter, L. (2010). Transcript assembly and quantification by RNA-Seq reveals unannotated transcripts and isoform switching during cell differentiation. Nat. Biotechnol. 28, 511-515.

Wolf, F. A., Angerer, P., and Theis, F. J. (2018). SCANPY: large-scale single-cell gene expression data analysis. Genome Biol. 19, 15.

Zhang, H., Brainson, C. F., Koyama, S., Redig, A. J., Chen, T., Li, S., Gupta, M., Garcia-de-alba, C., Paschini, M., Herter-sprie, G. S., et al. (2017). Lkb1 inactivation drives lung cancer lineage switching governed by Polycomb Repressive Complex 2. Nat. Commun. 8, 1-14.

The invention claimed is:

1. A method for treating a lung disease or disorder, or a lung injury, in a subject in need thereof, the method comprising administering to a subject, intratracheally, a therapeutically effective amount of a composition comprising an alveolar organoid or an isolated cell thereof,
   wherein the alveolar organoid is provided or produced in vitro or ex vivo from a lung cell by culturing the lung cell in a 3-dimensional culture for a time and under conditions sufficient to produce the alveolar organoid, wherein administering is transplanting, and
   wherein the alveolar organoid or cell thereof functionally engrafts into the lung after transplanting thereby treating the lung disease or disorder or lung injury in the subject.

2. The method of claim 1, wherein the alveolar organoid or cell thereof is CD31/CD45−, Epcam+ and Sca1− in murine cells, or CD31−/CD45−, Epcam+, and HTII-280+ in human cells.

3. The method of claim 1, wherein the alveolar organoid or cell thereof are autologous to the subject to be treated; or wherein the alveolar organoid or cell thereof are heterologous to the subject to be treated.

4. The method of claim 1, wherein the alveolar organoid further comprises a lung epithelial cell, or a stromal cell.

5. The method of claim 1, wherein the lung cell is isolated from a donor or is derived in vitro from a stem cell.

6. The method of claim 5, wherein the stem cell is an induced pluripotent stem cell (iPSC), an embryonic stem cell, or a lung progenitor cell.

7. The method of claim 1, wherein the alveolar organoid is a human primary alveolar (hPAL) cell-derived organoid, a human iPSC-derived organoid or a human primary airway (hPAR) cell-derived organoid.

8. The method of claim 1, wherein the lung cell is CD31/CD45− and Epcam+.

9. The method of claim 8, wherein the lung cell is Sca1+; or wherein the lung cell is Sca1−.

10. The method of claim 1, wherein the Sca1+organoids engraft and populate in the alveolar space.

11. The method of claim 1, wherein the Sca1−organoids engraft into regions of the lung having damaged alveolar cells.

12. The method of claim 10, wherein the engrafted cells are Keratin 8+ and/or Keratin 17+.

13. The method of claim 1, wherein the transplanted or engrafted cells retain progenitor function as assessed by (i) their ability to give rise to organoids when returned to in vitro culture and/or (ii) their ability to respond to a second lung injury.

14. The method of claim 1, further comprising, prior to transplanting, the step of diagnosing a subject as having a lung disease or disorder, and/or being immunocompromised.

15. The method of claim 1, further comprising, prior to transplanting, receiving the results of an assay that diagnoses a subject as having a lung disease or disorder, and/or being immunocompromised.

16. The method of claim 1, further comprising the step of genetically modifying the lung cell, and/or the alveolar cell.

17. The method of claim 1, further comprising administering an immunosuppressive agent prior to, or substantially at the same time as the transplantation.

* * * * *